(12) United States Patent
Ghaffari

(10) Patent No.: US 11,817,660 B1
(45) Date of Patent: Nov. 14, 2023

(54) CONNECTOR DEVICE FOR A CABLE APPARATUS

(71) Applicant: Dariush Ghaffari, Omaha, NE (US)

(72) Inventor: Dariush Ghaffari, Omaha, NE (US)

( * ) Notice: Subject to any disclaimer, the term of this patent is extended or adjusted under 35 U.S.C. 154(b) by 107 days.

(21) Appl. No.: 17/013,197

(22) Filed: Sep. 4, 2020

Related U.S. Application Data

(60) Provisional application No. 62/895,841, filed on Sep. 4, 2019.

(51) Int. Cl.
| | |
|---|---|
| *H01R 31/00* | (2006.01) |
| *H01R 13/627* | (2006.01) |
| *H01R 11/24* | (2006.01) |
| *A61B 5/318* | (2021.01) |

(52) U.S. Cl.
CPC .......... *H01R 31/005* (2013.01); *A61B 5/318* (2021.01); *H01R 11/24* (2013.01); *H01R 13/6277* (2013.01); *A61B 2562/222* (2013.01); *A61B 2562/227* (2013.01); *H01R 2201/12* (2013.01)

(58) Field of Classification Search
CPC ........ H01R 31/06; H01R 24/28; H01R 24/20; H01R 31/005; H01R 11/24; H01R 13/6277; A61B 2562/222; A61B 2562/227; A61B 5/318; Y10S 439/909
See application file for complete search history.

(56) References Cited

U.S. PATENT DOCUMENTS

| | | | |
|---|---|---|---|
| 5,944,562 A | 8/1999 | Christensson | |
| 7,255,609 B1* | 8/2007 | Epstein | H01R 31/06 439/857 |
| 7,277,743 B2 | 10/2007 | Brodnick | |
| 7,445,522 B2 | 11/2008 | Burnes et al. | |
| 9,226,678 B1* | 1/2016 | Ghaffari | A61B 5/303 |
| 2005/0113661 A1 | 5/2005 | Nazeri et al. | |
| 2008/0249390 A1 | 10/2008 | McIntire et al. | |

* cited by examiner

*Primary Examiner* — Oscar C Jimenez
*Assistant Examiner* — Paul D Baillargeon
(74) *Attorney, Agent, or Firm* — Suiter Swantz pc llo

(57) ABSTRACT

The present disclosure is directed to an apparatus for measuring a health condition and connectable to existing medical devices. In one embodiment, apparatus may include a cable apparatus. The cable apparatus may include a plurality of conductors enclosed within an exterior covering and may include a plurality of mating devices; the plurality of mating devices located along a length of the cable. Each mating device may be coupled to a conductor of the cable. Cable apparatus may further include a connector device, the connector device coupled to an end of the cable and configured to couple the cable apparatus with a recording/monitoring device by coupling with an existing set of leads associated with the recording/monitoring device. Connector device may allow quick attachment and detachment of the cable apparatus.

14 Claims, 50 Drawing Sheets

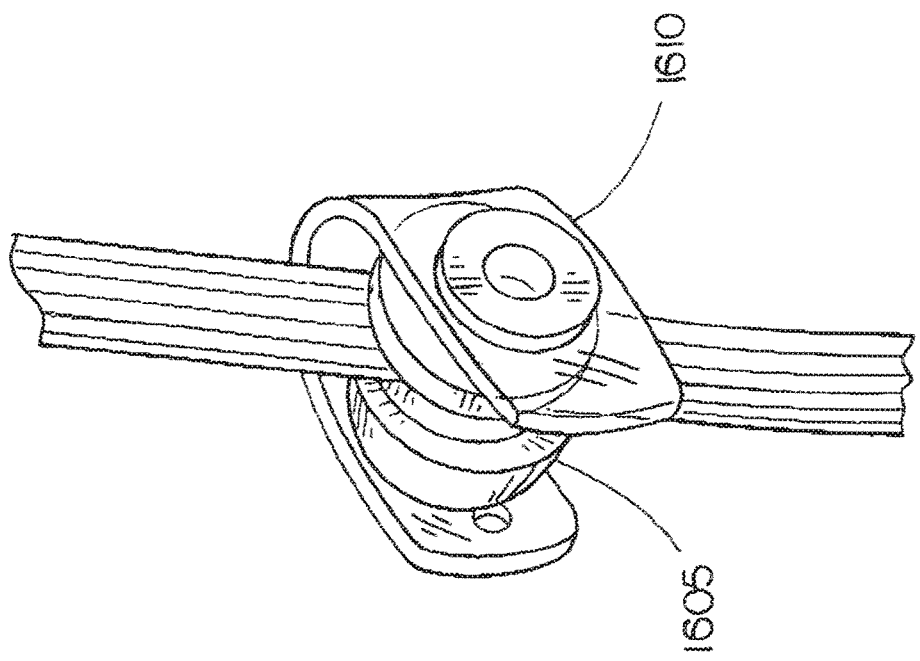
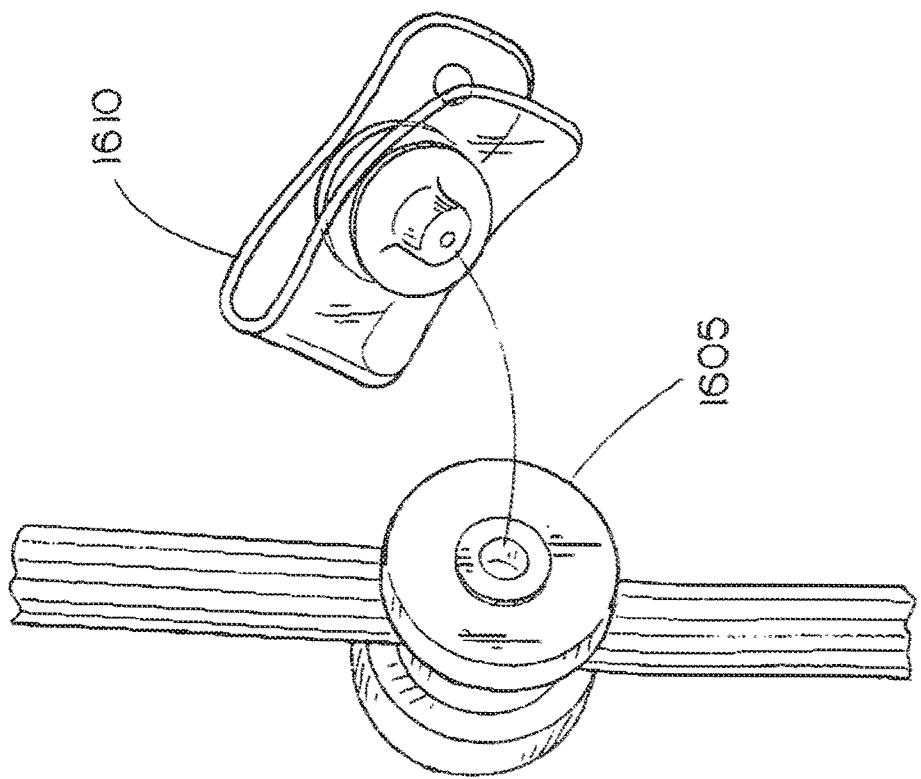

US 11,817,660 B1

CONNECTOR DEVICE FOR A CABLE APPARATUS

CROSS REFERENCE TO RELATED APPLICATIONS

The present application claims priority under 35 U.S.C. § 119 to U.S. Provisional Application Ser. No. 62/895,841, filed Sep. 4, 2019. Said U.S. Provisional Application Ser. No. 62/895,841, filed Sep. 4, 2019, is hereby incorporated by reference in its entirety.

TECHNICAL FIELD

The present disclosure generally relates to the field of medical health applications and more particularly to a connector device for a cable apparatus connectable to medical devices.

BACKGROUND

Medical health monitoring is employed in order to evaluate and determine a health condition. One form of medical health monitoring is electrocardiography. Electrocardiography refers to a method of recording electrical impulses from a heart. A device which performs electrocardiography is an electrocardiograph, also known as an ECG, EKG, ECG device, EKG machine and the like (hereinafter referred as EKG). An EKG may receive the electrical signals representative of electrical impulses from a heart through a set of leads connected to a plurality of electrode pads that may be placed upon skin in various locations on a body of a patient. Electrocardiography may be employed to measure and diagnose abnormal rhythms of the heart and potential damage to conductive tissue of the heart which carries electrical signals.

BRIEF DESCRIPTION OF THE DRAWINGS

The numerous advantages of the disclosure may be better understood by those skilled in the art by reference to the accompanying figures in which:

FIGS. 16A, 16B and 16C depict exploded views of mating devices associated with a cable in accordance with an embodiment of the present disclosure;

DETAILED DESCRIPTION

Reference will now be made in detail to the subject matter disclosed, which is illustrated in the accompanying figures.

Figure 1:
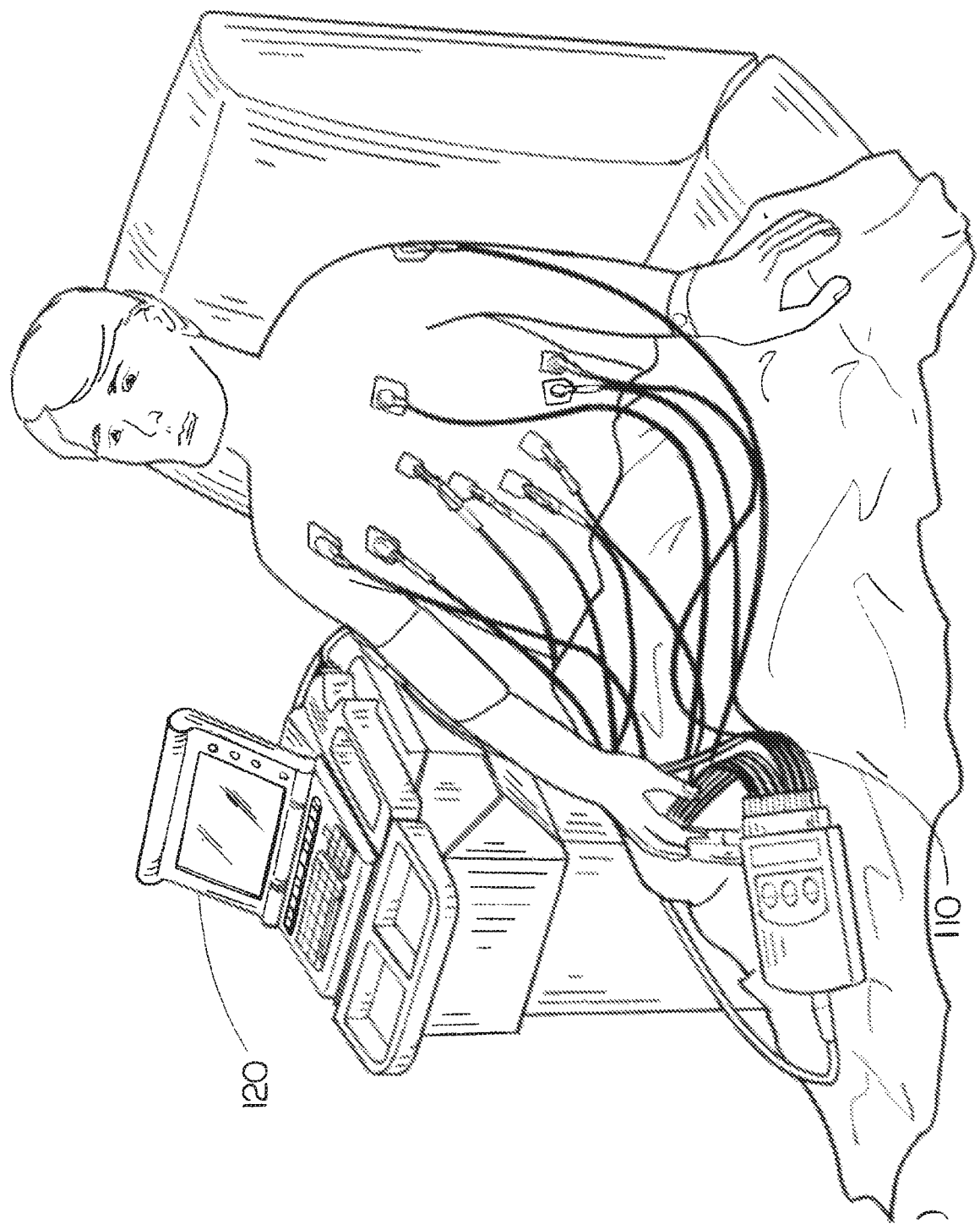
FIG. 1 depicts a conventional set of leads coupled to an EKG machine.

Referring to FIG. 1, a conventional set of leads 110 coupled to an EKG machine 120 is shown. Set of leads 110 are coupled to electrode pads which are adhesively connected to skin of a patient. The use of set of leads 110 is accompanied by a number of problems. Set of leads 110 are placed upon the body of the patient and may come into contact with a patient's fluids. Consequently, there is a risk of spread of infection and disease through re-use of set of leads 110 with another patient. Another set of leads 130 may also be utilized to connect to a monitor device 140. Disinfection techniques for the set of leads 110, 130 are limited in their effectiveness and are costly.

Set of leads 110 includes a number of wires, for example from five to twelve wires. When set of leads 110 is stored, it is common that the wires may become tangled. When set of leads 110 is needed for an EKG test, the wires must be detangled to allow connection with electrode pads and execution of the EKG test. Electrode pads (also known as electrodes) may produce an electrical contact with a non-metallic part of a circuit, such as skin of a patient. Operating personnel may appear awkward and incompetent trying to find the corresponding wires to detangle and connect to electrode pads on a patient's torso and extremities, creating unnecessary patient apprehension and loss of time in an emergency situation.

Additionally, set of leads 110 may be heavy. When patients move while set of leads 110 is connected to electrode pads on their bodies, tension and torque is placed on electrode pads. This can result in displacement of the pads from the patient which may be adhesively fixed to skin of the patient, but may lose contact with the patient if a force is applied to the electrode pad from movement by set of leads 110. This results in a loss of signal requiring repeated adjustments and application of new adhesive electrode pads.

Cable Apparatus

Figure 2:
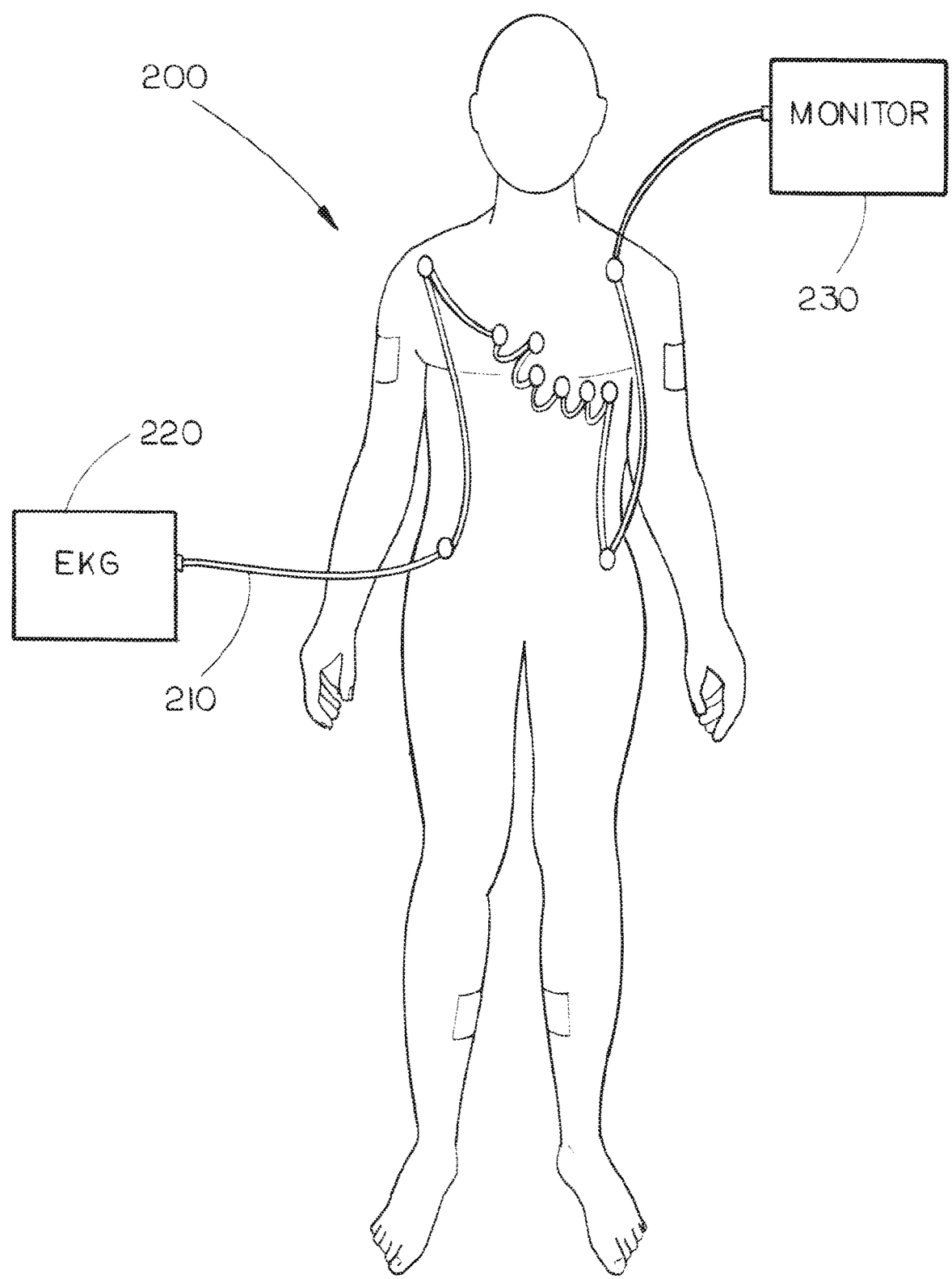
FIG. 2 depicts a cable apparatus in accordance with an embodiment of the present disclosure.

Referring to FIG. 2, a cable apparatus 200 in accordance with an embodiment of the present disclosure is shown. Cable apparatus 200 may include a cable 210. Cable 210 may include a plurality of conductors, the conductors being isolated and insulated from each other. Cable 210 may include an exterior covering which enclose the plurality of conductors. Exterior covering may include a non-conductive coating as applied within a printed circuit. Exterior covering may be a fabric, rubber, plastic and other similar non-conductive materials. Advantageously, cable 210 may be produced with soft, flexible materials which may not become tangled as occurs with a conventional set of leads. Also, cable 210 may be lighter than conventional set of leads and thus more comfortable for a patient.

Cable 210 may include a plurality of mating devices. The plurality of mating devices may be located along a length of cable 210 to correspond to various locations on a body. It is contemplated that a distance between each mating device is based upon typical attachment to various locations on a torso of a patient. However, a cable 210 may be produced suitable for a child whereby the distance between each mating device may be reduced to a distance between each mating device for a cable suitable for an adult. Each mating device of the plurality of mating devices may be coupled to a conductor of the cable 210 via a physical electrical connection via various types of conducting devices. Each mating device may be configured to couple with an electrode pad causing an electrical connection between a conductor and the electrode pad. In an embodiment, each mating device may include an identifier, such as a particular icon or color, to identify its proper location on a body. For example, a red mating device may be placed on a right shoulder area of a patient while a blue mating device may be placed on a left shoulder area of a patient. In one embodiment, mating devices may be color coded in accordance with AHA and IHA standards.

Cable 210, through mating devices coupled to electrode pads, may be attached to the body in a number of locations, such as from a left shoulder and travels down to the left hip (Lower Abdomen), travels to the left side of chest, across the chest and travels up to the right side of the sternum, attaches to the right shoulder and travels down and finally attaches to the right hip (lower abdomen). Cable 210 may be attached to an EKG machine 220 in a safe distance away from the patient. Cable 210 may also be attached to a monitor device 230. Monitor device 230 may be any type of health monitoring device, including real time monitor device. Monitor device 230 may be a heart rate monitor, scope, blood pressure monitor and the like. Advantageously, cable 210 and its associated connections may be employed for use with EKG machine 220 and monitor device 230 without requiring multiple cables and multiple electrode pads connected to a patient. Cable 210 may be operable for variety of types of EKG machines, including 3-12 lead EKG machines. Additionally, cable 210 may include a connector device at each end to allow coupling to EKG machine 220 or monitor 230 without requiring replacement of the electrode pads, with both the EKG machine 220 and the monitor 230 being operable simultaneously via the same single cable 210. As cable 210 may be formed of flexible material, there is minimal torque placed on the electrode pads and thus replacement of electrode pads is reduced in comparison with use of a conventional set of leads as shown in FIG. 1.

Figure 3:
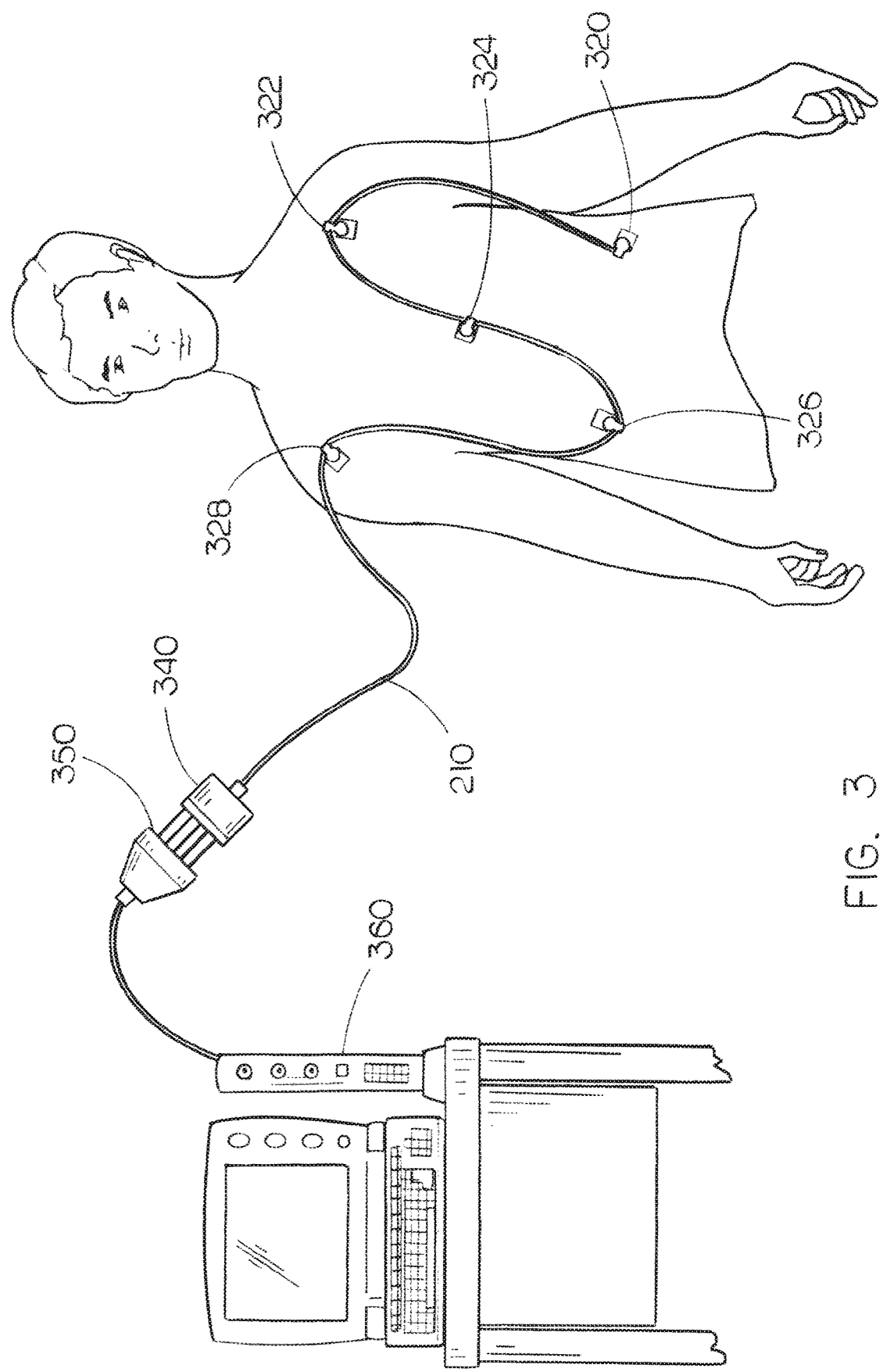
FIG. 3 depicts a cable apparatus coupled with a set of leads of an EKG machine in accordance with an embodiment of the present disclosure.

Referring to FIG. 3, cable apparatus 300 coupled with set of leads 350 of an EKG machine 360 in accordance with an embodiment of the present disclosure is shown. Cable apparatus 300 may include a cable 210 which includes a plurality of mating devices 320-328 located along a plurality of positions along the length of cable 210 from a first end of the cable to a second end of the cable, in various spacing between the mating devices, which can correspond to various positions of a chest of a user. For example, mating devices configured to be coupling with an area around the heart may be closely spaced together while there is more space between the mating devices between the lower abdomen and shoulder areas. Cable apparatus 300 may further include at least one connector device 340. Connector device 340 may be coupled to an end of cable 210, or both ends of a cable 210, and may connect cable 210 with a set of leads 350 from an EKG machine 360. As shown in FIG. 3, cable 210 may include five mating devices which may be suitable for a five lead EKG machine 360. While cable 210 includes five mating devices, it is contemplated that any number of mating devices may be included with cable 210 without departing from the scope and intent of the present disclosure.

Connector device 340 may be any type of universal connector device, or adapter for coupling cable 210 and its associated conductors with set of leads 350 or any type of set of leads coupled to a monitor 230 as shown in FIG. 2. Set of leads 350 may include alligator clips, male plugs, and may include female receptacles of snap connectors along with various additional connectors. Connector device 340 may couple to the alligator clips or female receptacles of the snap connectors associated with a set of leads 350 attached to an electrocardiograph 360. This may form a cable extension coupled from the set of leads 350 which may be utilized to connect to the patient. This may be advantageous as set of leads 350 may not be in proximity with the patient. As cable 210 may be manufactured in a cost-efficient manner, it is contemplated that cable 210 may be utilized for a single patient then disposed, preventing the risk of transmission of disease or infection.

In one embodiment, connector device 340 may include a cable connector, such as a telephone jack. Cable connector of connector device 340 may be configured to couple with a corresponding cable connector. Cable connector may be a telephone jack whereby a corresponding cable connector may include a telephone plug. While connector device 340 may include a telephone jack, it is contemplated that connector device 340 may be any type of device or devices for connecting a set of leads 350 from an electrocardiograph or monitor and the plurality of conductors of a cable 210.

Connector device 340 may be further configured to couple with set of leads 350 from the electrocardiograph 360 or set of leads from a monitor device. For example, connector device 340 may include a plate with a plurality of male groove portions of snap connector. Female receptacles of snap connectors of set of leads 350 may couple with male groove portions of snap connector. Connector device 340 may be operable with any type of set of leads from any type of EKG machine or medical monitoring device allowing cable 210 to be operable with any type of medical equipment and is not dependent upon the manufacturer and model type. Connector device 340, and various alternative embodiments of connector device 340, are shown and further described in FIGS. 18-28.

Figure 4:
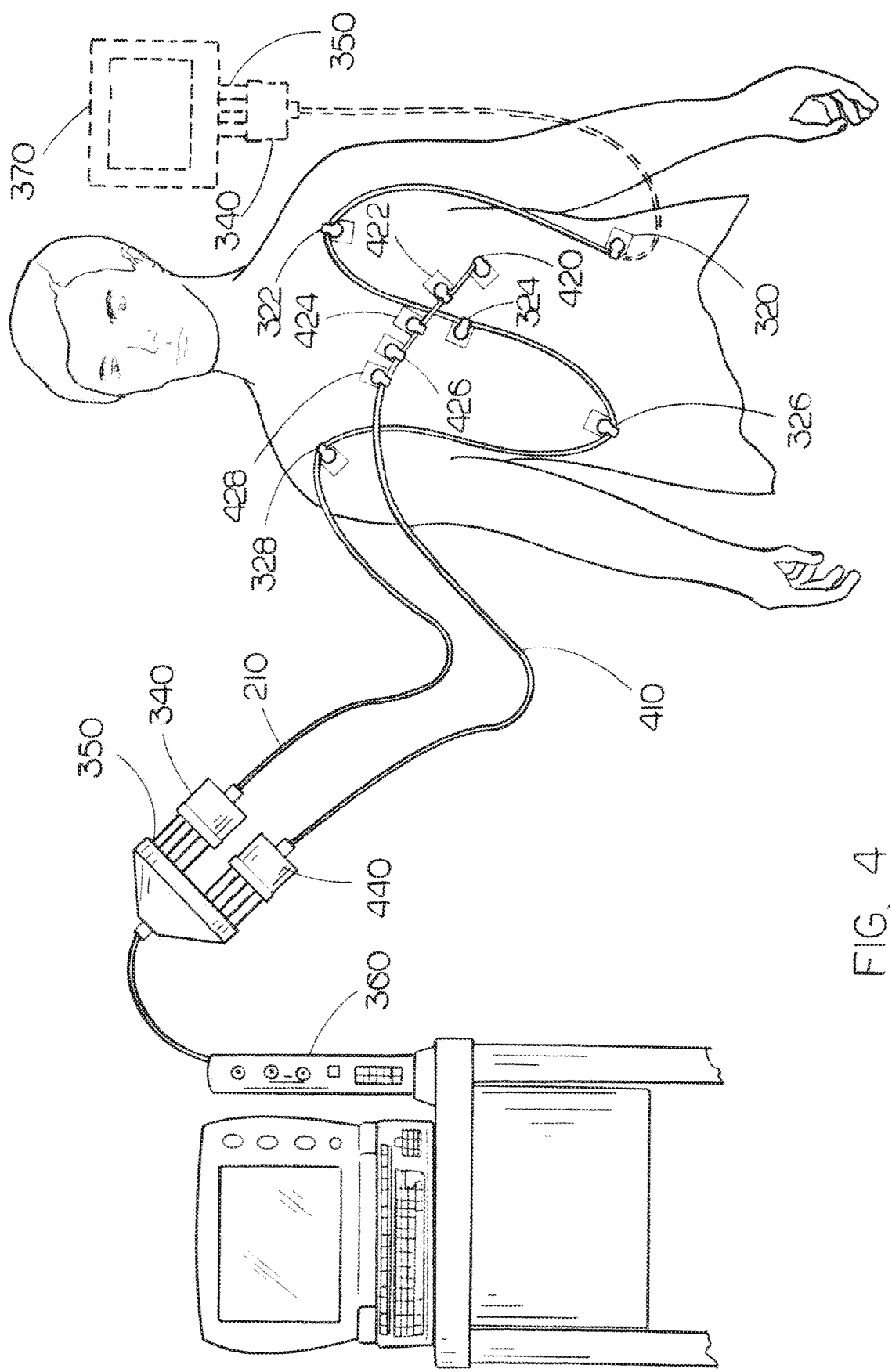
FIG. 4 depicts multiple cables coupled with a set of leads of an EKG machine in accordance with an embodiment of the present disclosure.

Referring to FIG. 4, multiple EKG cables coupled with a set of leads 350 of an EKG machine 360 in accordance with an embodiment of the present disclosure are shown. Similar to cable apparatus 300 as shown in FIG. 3, cable 210 may be coupled with set of leads 350 of an EKG machine 360. In one embodiment, cable 210 may include another connector device 340 which couples to set of leads 350 from a monitor 370. It is contemplated that cable 210 including mating devices 320-328 may be utilized in combination with a cable 410 including mating devices 420-428. Cable 410 may be coupled to set of leads 350 from an EKG machine 360 via a connector device 440. It is contemplated that cable 410, mating devices 420-428 and connector device 440 may be similar in design and operation as cable 210, mating devices 320-328 and connector device 340. The use of cables 210, 410 may be combined to connect with electrode pads and allow use of a ten lead EKG machine. The use of two cables may be advantageous as cable 210 may be utilized by emergency personnel from an ambulance which may utilize a five lead EKG machine and may leave the cable 210 attached to the patient whereby an hospital EKG machine could add cable 410 to provide a ten lead EKG test. Additionally, cable 210 may be coupled to a monitor 370 which allows monitoring of health information, including heart characteristics such as heart rate, blood pressure and the like. It is contemplated that electrode pads may require slight movement on the body of a patient while be utilized for a EKG test and health monitoring but may be accomplished without use of multiple cables from each of the EKG machine 360 and monitor 370.

Figure 5:
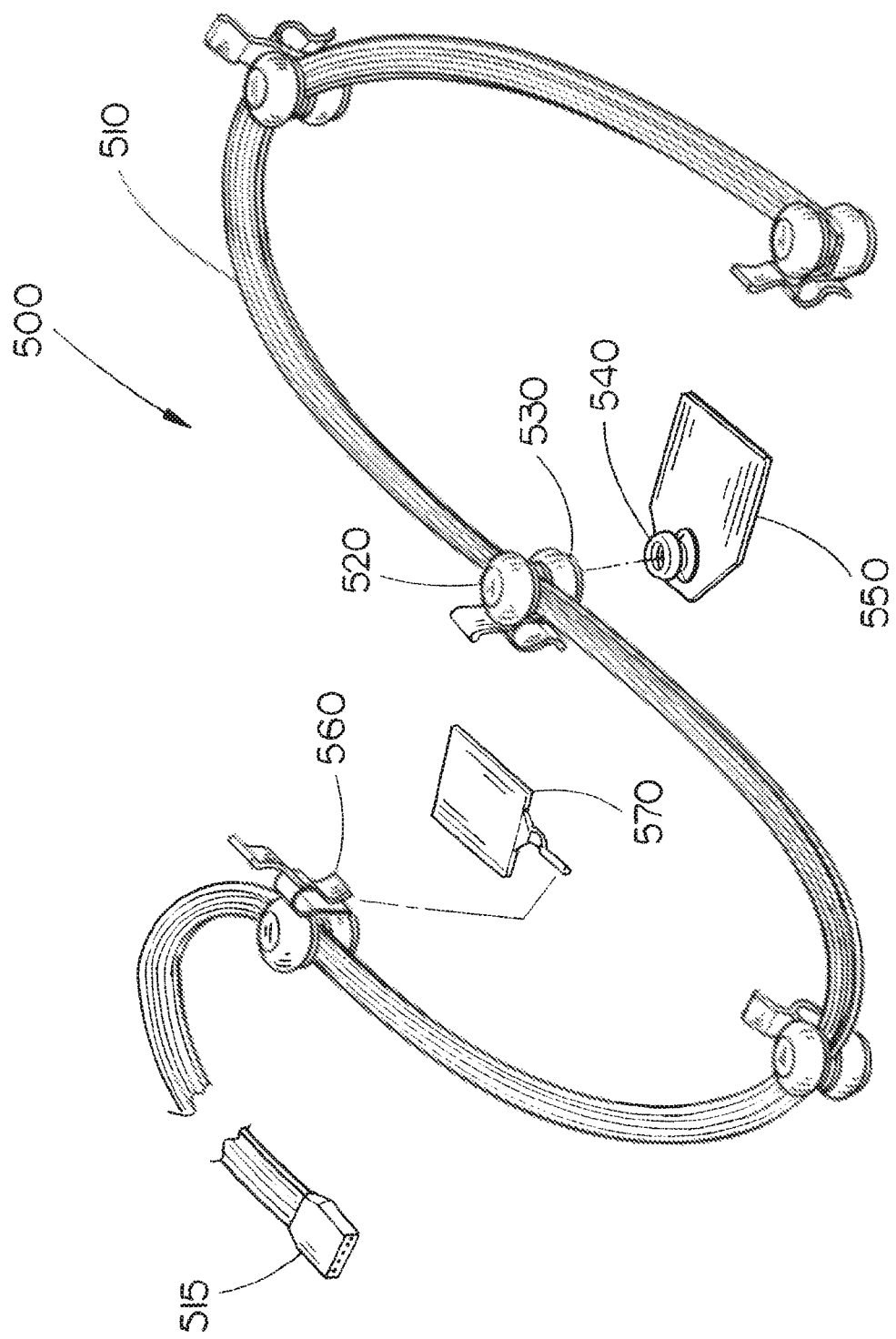
FIG. 5 depicts a detailed view of a cable apparatus in accordance with an embodiment of the present disclosure.

Referring to FIG. 5, a detailed view of a cable apparatus 500 in accordance with an embodiment of the present disclosure is shown. Cable apparatus 500 may include a cable 510 with a plurality of conductors enclosed within an exterior covering. Cable 510 may include six conductors whereby five conductors may be employed for a five lead EKG machine; however, three conductors or more may also be employed for monitoring. Cable 510 may be any type of cable with a plurality of conductors within the cable, such as a telephone cable, ethernet cable and the like. Cable 510 may include a connector device 515. Connector device 515 may couple cable 510 and each of its plurality of conductors with a set of leads from an electrocardiograph. In one embodiment, connector device 515 may be any type of connector device, and may be a telephone plug or ethernet plug. For example, connector device may be a plug-in compliance with registered jack 25, also known as RJ25. While cable 510 includes a single connector device 515, it is contemplated that an additional connector device 515 may be included on another end of cable 510 without departing from the scope and intent of the present disclosure.

Cable 510 may include a plurality of mating devices. Each mating device 520 may include a female receptacle 530 of a snap connector with a zero insertion force mechanism to enhance patient comfort when applying the mating devices. Female receptacle 530 may be configured to connect with a corresponding male groove 540 coupled with an electrode pad 550. It is contemplated that size of female receptacle may be similar as a size of female receptacles for an existing set of leads for an electrocardiograph whereby it will be operable with existing male groove portions of snap connector coupled to an electrode pad. Mating devices of cable 510 may further include an alligator clip 560, which also has a zero insertion force mechanism, suitable for coupling with an electrode pad 570. An alligator clip, also known as a spring clip or crocodile clip, may refer to an electrical connector. An alligator clip may include two jaws which may be mechanically forced together, when not separated by an opposing force, causing an electrical connection with an object coupled between the two jaws. Alligator clip may include binding clips, clamps and the like.

Figure 6:
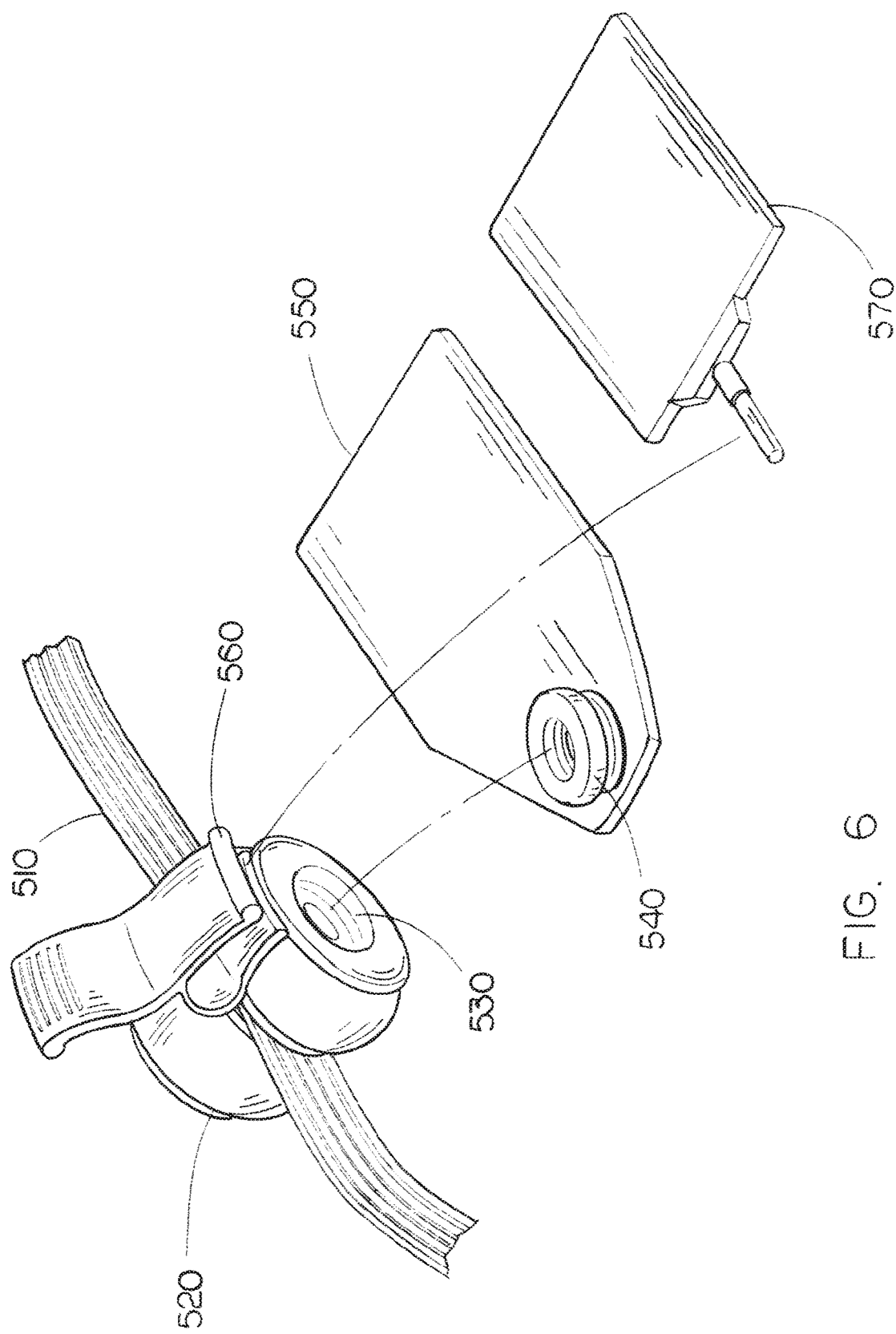
FIG. 6 depicts a detailed view of a mating device configured for coupling to multiple types of electrode pads in accordance with an embodiment of the present disclosure.

FIG. 6 depicts a detailed view of a mating device 520 configured for coupling to multiple types of electrodes in accordance with an embodiment of the present disclosure. It is contemplated that cable 510 as shown in FIG. 5 may be employed with a variety of EKG machines and may also be employed with other applications. Mating device 520 including a female receptacle 530 of a snap connector may be operable with electrode pad 550 with male groove portion of a snap connector 540. Additionally, mating device 520 may also be operable with electrode pad 570 which are configured to receive a connection via an alligator clip 560. By providing additional flexibility, cable 510 may be operable in a variety of applications and uses, including EKG monitoring, heart rate testing, blood pressure testing and the like. While the alligator clip 560 is placed along a parallel axis as the female receptacle 530, it is contemplated that alligator clip 560 may be oriented in other directions and placed in other locations on the mating device 520 without departing from the scope and intent of the present disclosure.

Figure 7:
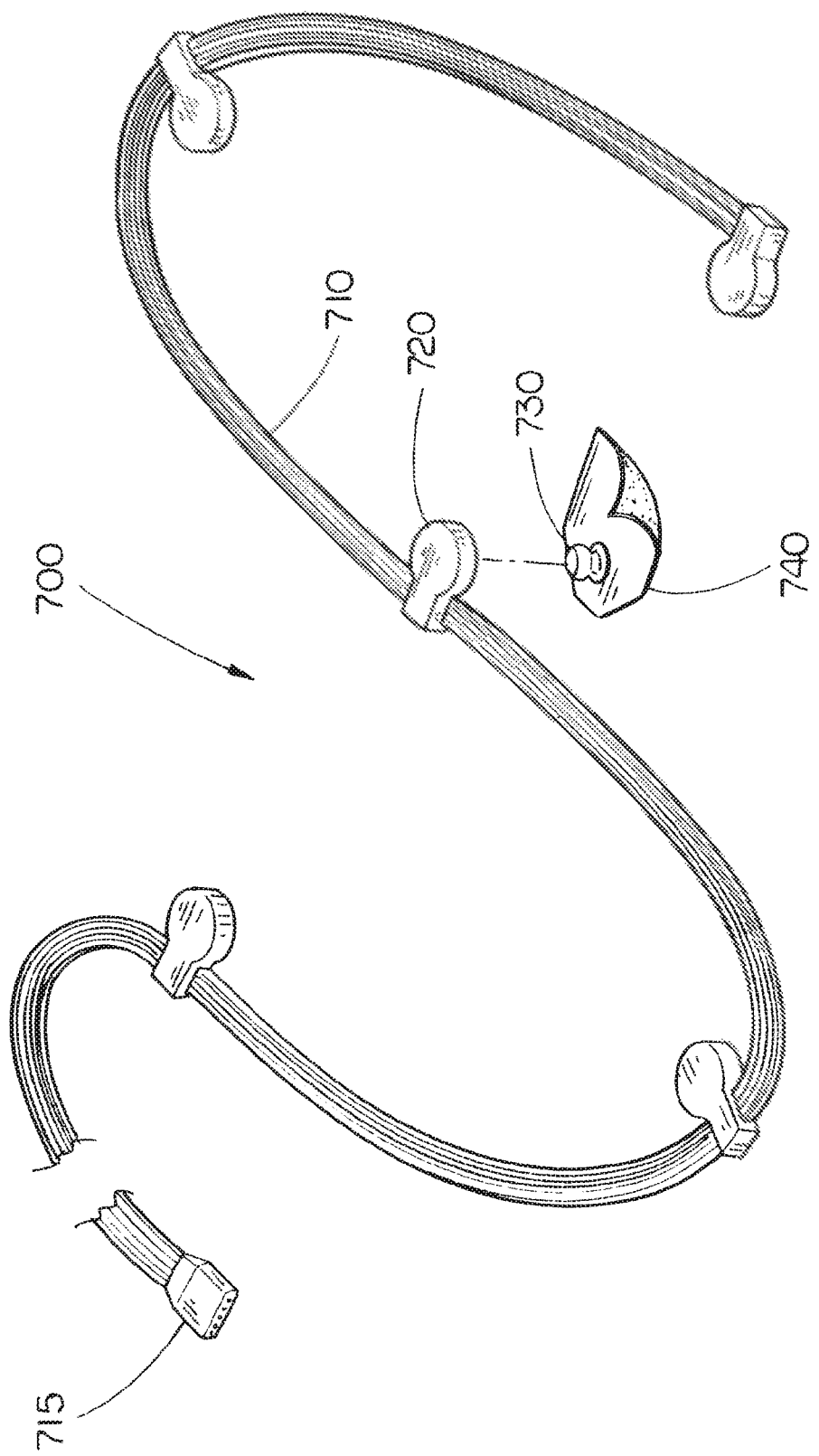
FIG. 7 depicts a detailed view of a cable apparatus in accordance with an alternative embodiment of the present disclosure.
Figure 8:
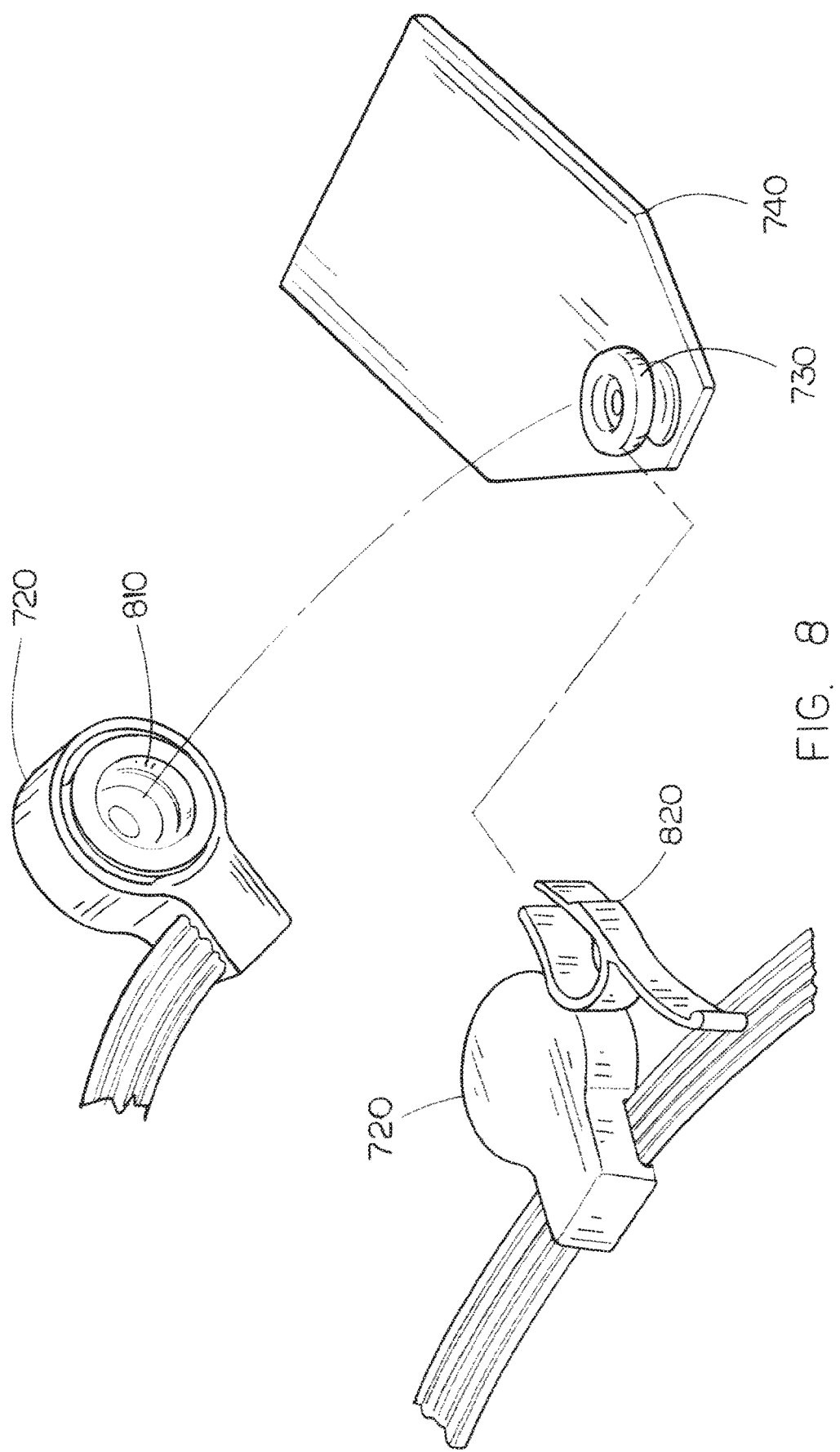
FIG. 8 depicts a detailed view of a mating device in accordance with an alternative embodiment of the present disclosure.
Figure 9:
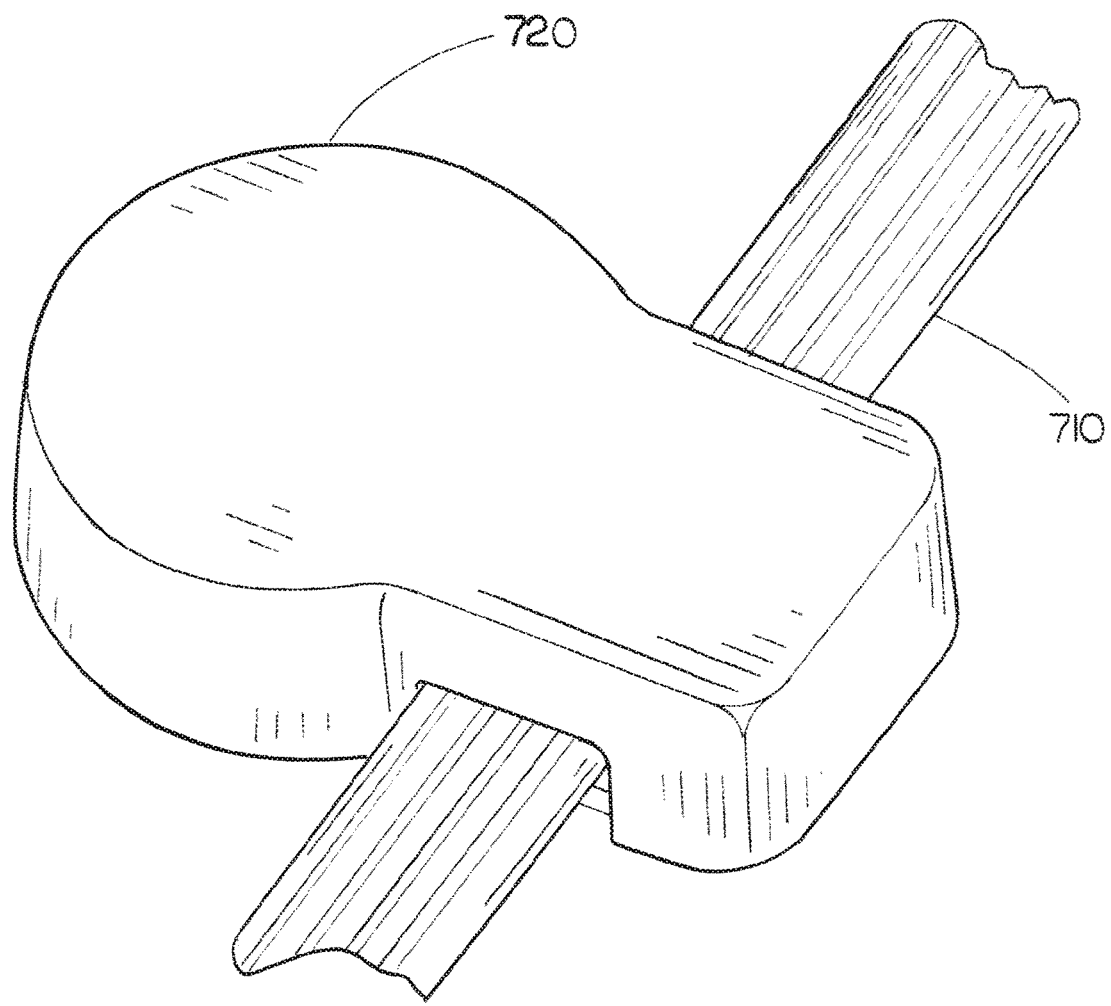
FIG. 9 depicts another detailed view of a mating device in accordance with an alternative embodiment of the present disclosure.

Referring to FIG. 7, a detailed view of a cable apparatus 700 in accordance with an alternative embodiment of the present disclosure is shown. Cable apparatus 700 may include a cable 710 with a plurality of conductors enclosed within an exterior covering. Cable 710 may include a plurality of conductors, such as five conductors which may be employed for a five lead EKG machine. Cable 710 may be telephone cable, ethernet cable and the like. Cable 710 may include a connector device 715. Connector device 715 may couple cable 710 and each of its plurality of conductors with a set of leads from an electrocardiograph. In one embodiment, connector device 715 may include a cable connector, the cable connector may be a telephone plug or ethernet plug. For example, connector device 715 may be a plug-in compliance with registered jack 25, also known as RJ25. While cable 710 includes a single connector device 715, it is contemplated that an additional connector device 715 may be included on another end of cable 710 without departing from the scope and intent of the present disclosure. Cable 710 may include a plurality of mating devices. Each mating device 720 may include a female receptacle of a snap connector suitable for coupling with a male groove portion of a snap connector 730 connected to an electrode pad 740.

Referring to FIGS. 8-11, a detailed view of a mating device 720 in accordance with an alternative embodiment of the present disclosure is shown. Mating device 720 may include a female receptacle 810 of a snap connector. Female receptacle 810 of a snap connector may be configured to connect with male groove portion of snap connector 730, the male groove portion of snap connector 730 being coupled to electrode pad 740.

Additionally, mating device 720 may include an alligator clip 820. Alligator clip 820 may allow connection with electrode pads which do not include a male groove portion of a snap connector or include a male groove portion of a snap connector of a different size than the size of female receptacle 810. While the alligator clip 820 is placed along a side of mating device 720, it is contemplated that alligator clip 820 may be oriented in other directions and placed in other locations on the mating device 720, such as on a top side of mating device 720, without departing from the scope and intent of the present disclosure.

Figure 10:
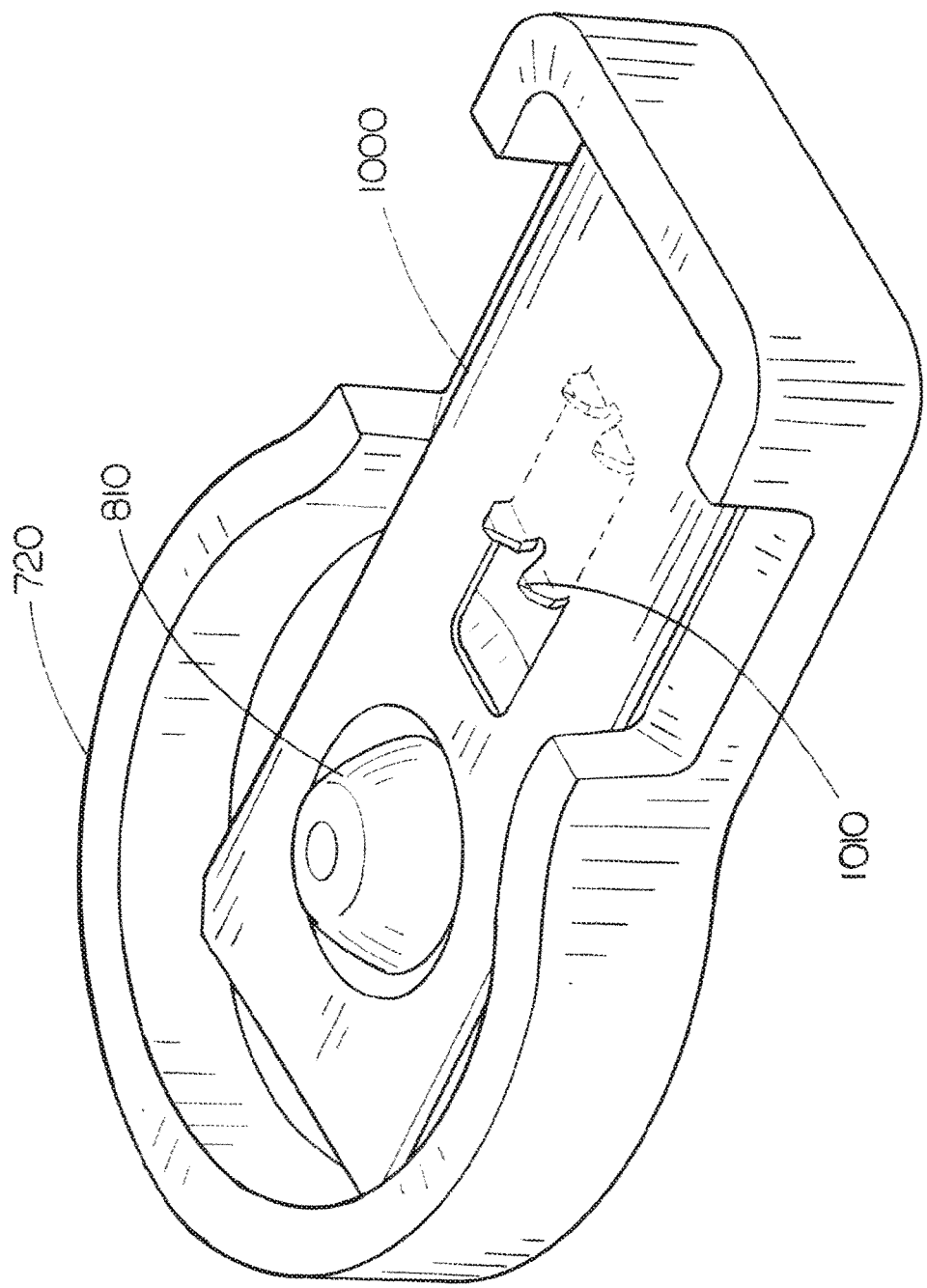
FIG. 10 depicts an interior view of a mating device in accordance with an embodiment of the present disclosure.
Figure 11:
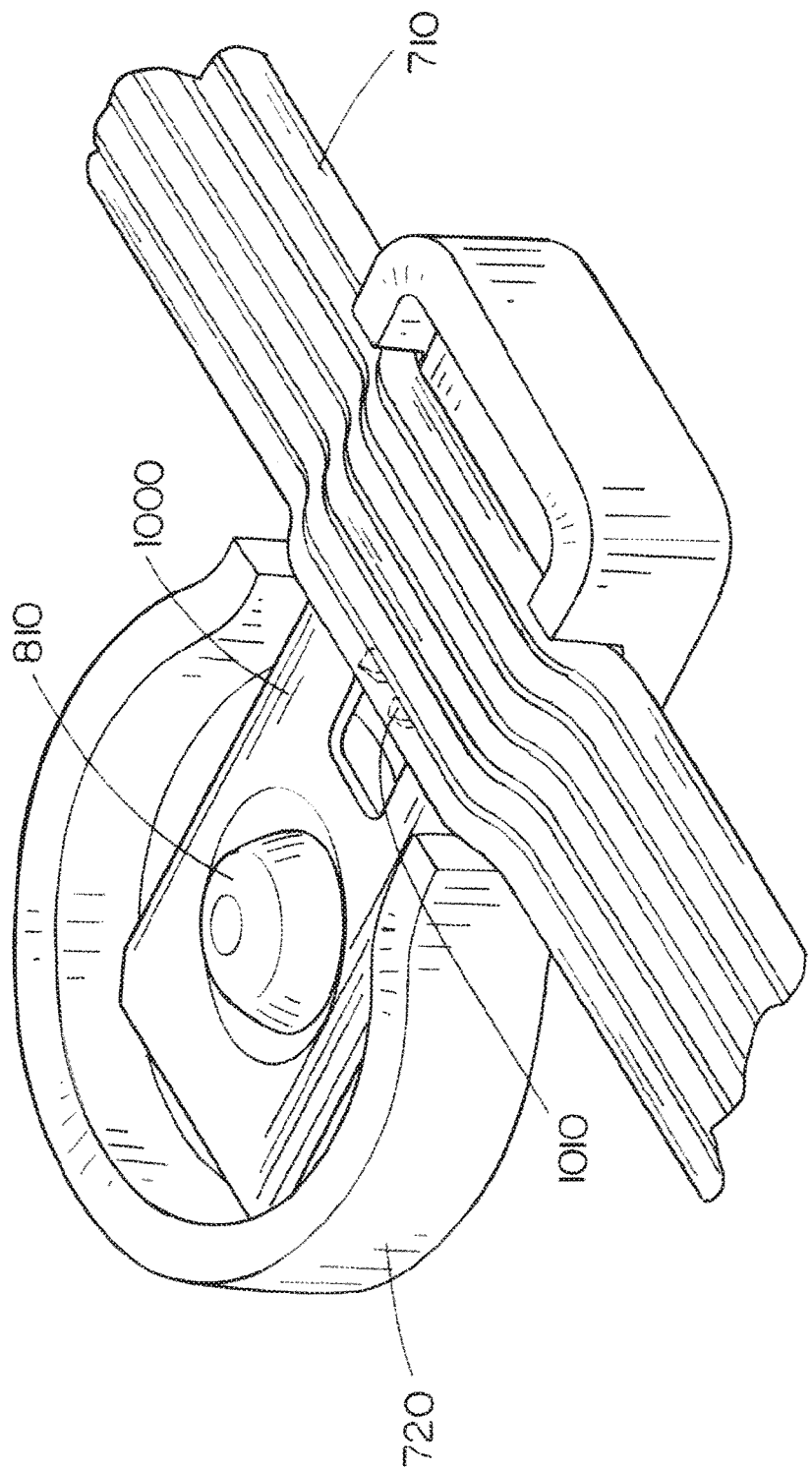
FIG. 11 depicts an interior view of a mating device with a cable in accordance with an embodiment of the present disclosure.
Figure 12A:
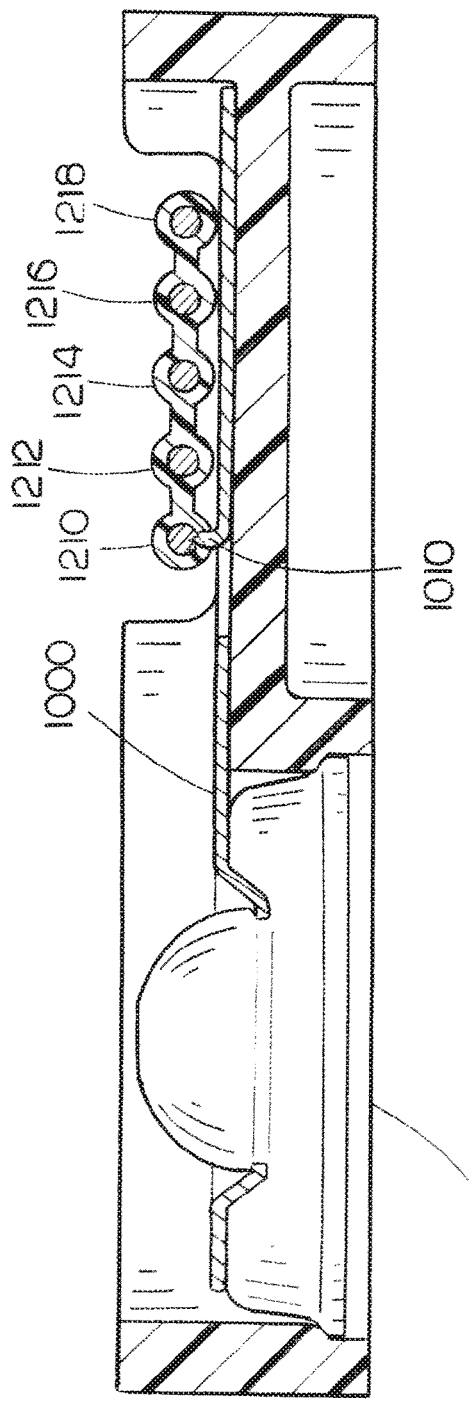
FIGS. 12A and 12B depicts an interior view of a mating device with notches for coupling with particular conductors of a cable in accordance with an embodiment of the present disclosure.
Figure 12B:
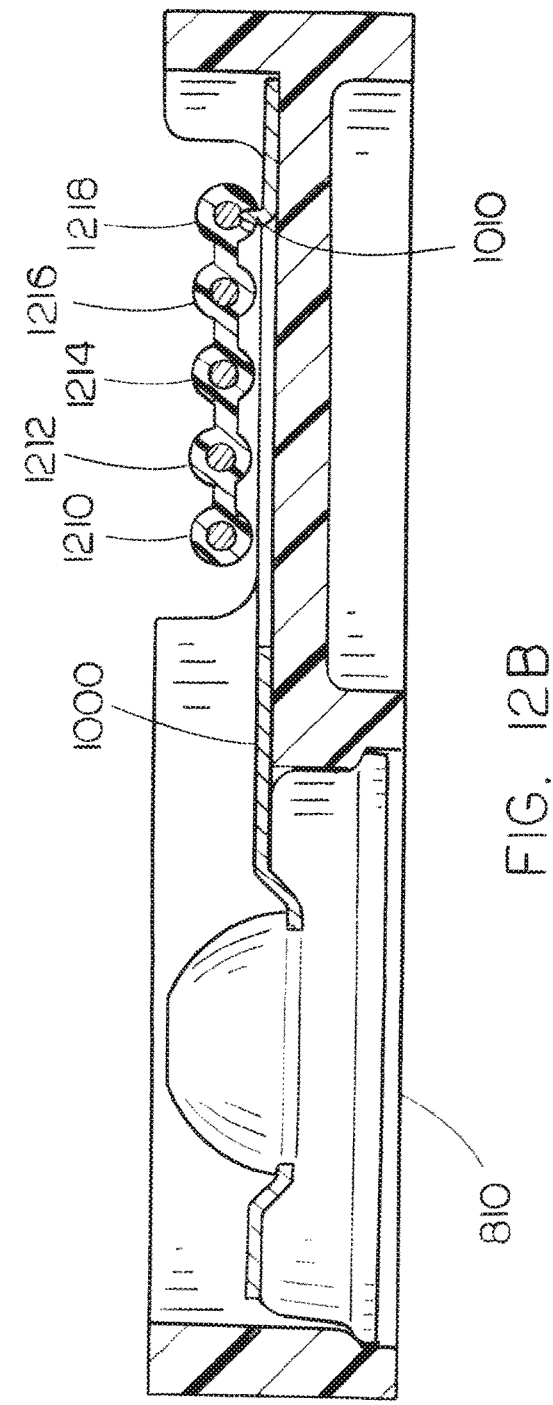

Referring to FIGS. 10-11, an interior view of a mating device 720 in accordance with an embodiment of the present disclosure is shown. Plate 1000 may be coupled with female receptacle 810. One or more notches 1010 may be coupled with plate 1000. One or more notches may be configured to be coupled with a conductor of cable 710. In one embodiment, plate 1000 and one or more notches 1010 may be formed as an integrated assembly. Through plate 1000, an electrical connection may be provided from an electrode pad, to the female receptacle 810 of mating device 720, to plate 1000, to one or more notches 1010 and to a conductor of cable 710. One or more notches 1010 may include a tapered edge which may be configured for piercing an exterior covering of a cable 710 to contact a conductor and ensure an electrical connection between a conductor and one or more notches 1010. Referring to FIGS. 12A and 12B, an interior side view of a mating device 720 with one or more notches 1010 for coupling with particular conductors of a cable 710 in accordance with an embodiment of the present disclosure is shown. It is contemplated that the location of one or more notches 1010 on plate 1000 may be adjusted to connect with a corresponding conductor of cable 710. For example, cable 710 may include conductors 1210, 1212, 1214, 1216 and 1218. As shown in FIG. 12A, one or more notches 1010 may be placed in a location suitable for connecting with conductor 1210. In FIG. 12B, one or more notches 1010 may be placed in a location suitable for connecting with conductor 1218. It is contemplated that plate 1000 with integrated one or more notches 1010 may be identified whereby the identification may indicate the particular conductor in which the mating device is designated to connect. As previously described, mating devices may include a visible identification for proper placement upon a patient. For example, a red mating device may be designated for placement upon a right shoulder area of a patient. A red plate may be utilized with a red mating device suitable for the right shoulder area of a patient.

Figure 13:
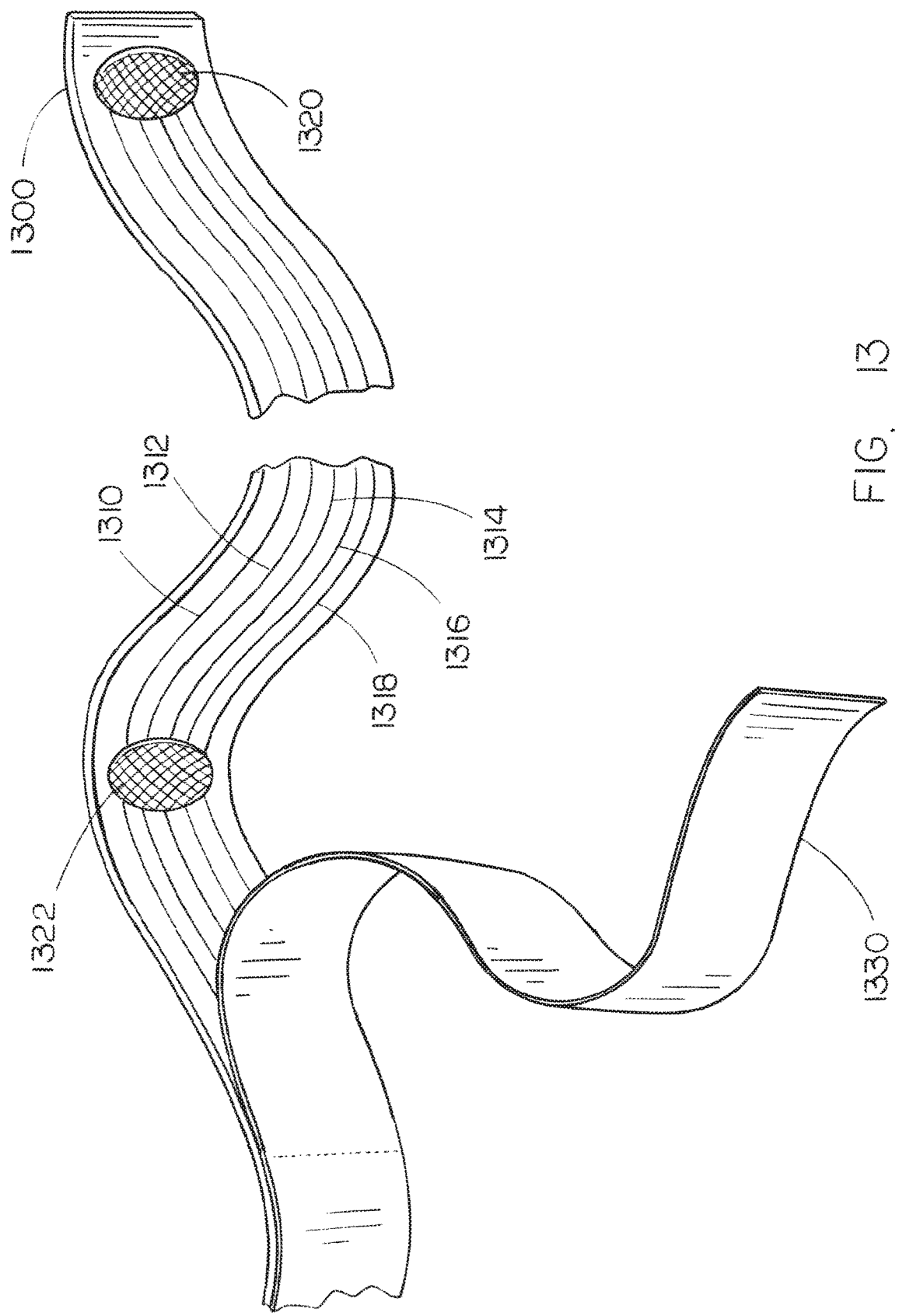
FIG. 13 depicts a detailed view of a cable in accordance with an additional embodiment of the present disclosure.

Referring to FIG. 13, a detailed view of cable 1300 in accordance with an additional embodiment of the present disclosure is shown. Cable 1300 may include a plurality of conductors 1310-1318 enclosed within an exterior covering. Cable 1300 may include mating device 1320, 1322. Mating device 1320, 1322 couple a conductor to an electrode pad which is coupled to skin of a patient. Mating device 1320, 1322 may include electrode pads which may be connected to the exterior covering of cable 1300. Electrode pads 1320, 1322 may include conductive gel and may include an adhesive for attaching to skin of a patient. It is contemplated that cable 1300 may be ribbon cable whereby the exterior cover is composed of rubber, a flexible plastic and the like. It is contemplated that exterior cover of cable 1300 may be composed of plastic, paper, paper products and the like. A removable cover 1330 may be employed with cable 1300. This may be advantageous to ensure the electrode pads connected to the exterior covering may adhere to skin of a patient. In one embodiment, removable cover 1330 may only be placed to cover each electrode pad prior to use. Use of cable 1300 by healthcare personnel may be advantageous as cable 1300 may be dispensed and attached to a patient in a quick and efficient manner. Cable 1300 may be extremely flexible and thin with the exterior covering composed of a nonconductive material that contains conductors along its length. Cable 1300 may be radiolucent.

A terminal portion of cable 1300 may be coupled to an EKG machine, monitoring device, and similar devices for processing of signals, such as viewing on a monitor or on a printout of electrocardiogram signals. Cable 1300 may include connector devices (not shown in FIG. 13) for coupling cable 1300 and its associated conductors with set of leads from an EKG machine and monitor. Cable 1300 may be employed in nerve conduction studies or Electromyogram (EMG). It can also be manufactured for muscle/nerve stimulation. It is contemplated that cable 1300 may be utilized whenever there is a need to either capture electrical impulses from the body or deliver electrical impulses to the body via the skin electrode pads.

Figure 14:
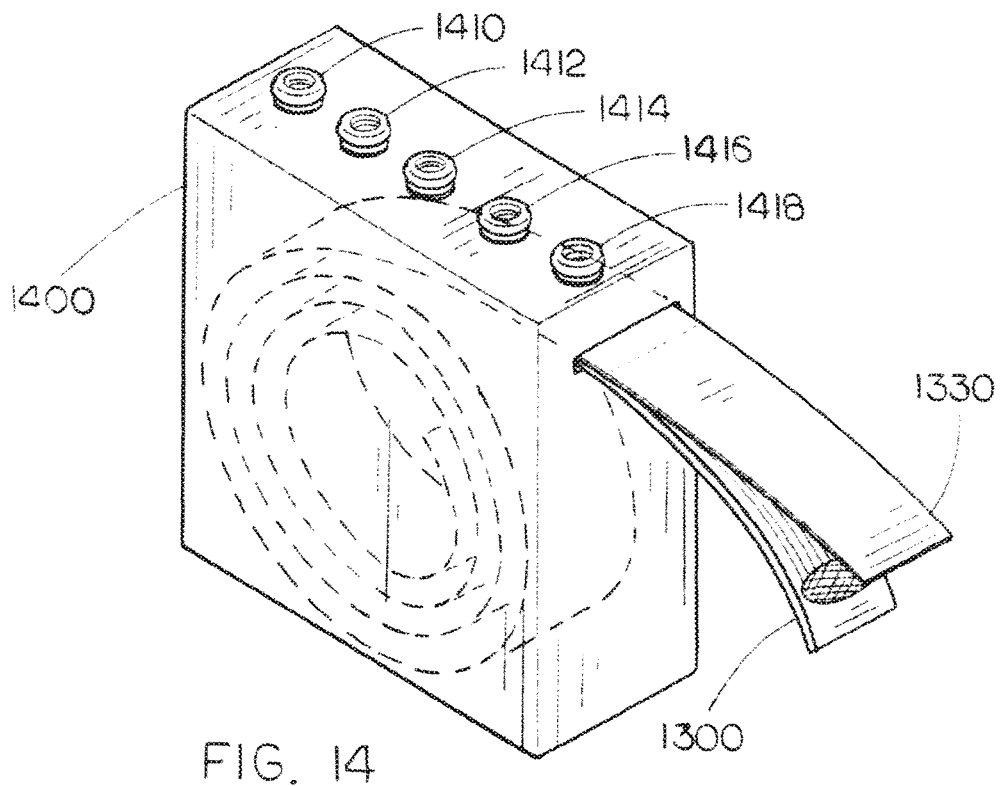
FIG. 14 depicts a dispenser for storage of a cable in accordance with an additional embodiment of the present disclosure.

Referring to FIG. 14, a dispenser 1400 for storage of cable 1300 in accordance with an additional embodiment of the present disclosure is shown. As cable 1300 may be flexible and substantially flat, it is contemplated that cable 1300 may be rolled and stored within an interior portion of dispenser 1400. It is contemplated that a plurality of cables may be stored within dispenser 1400. This may be advantageous as it may allow storage and an organized way to apply a flexible cable 1300. At the location between adjacent cables, a perforated edge may allow removal of a cable 1300 from dispenser 1400.

In one embodiment, dispenser 1400 may include male groove portions of snap connectors 1410-1418. Male groove portions of snap connectors 1410-1418 may be coupled to individual conductors of cable 1300. Male groove portions of snap connectors 1410-1418 may be configured to connect to female receptacles of snap connectors of an existing set of leads for an electrocardiograph or monitor.

Figure 15A:
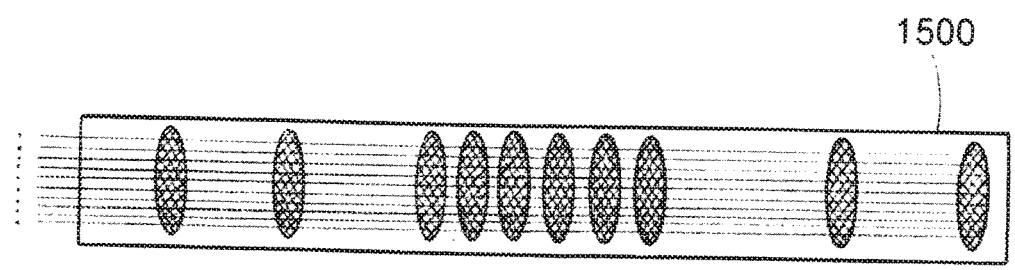
FIGS. 15A and 15B depict exploded views of a cable with mating devices in accordance with another additional embodiment of the present disclosure.
Figure 15B:
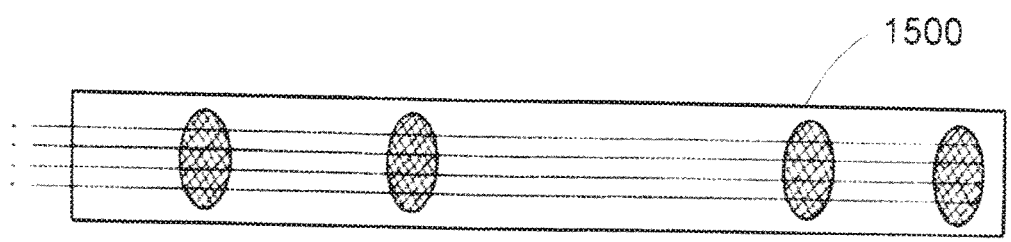

Referring to FIGS. 15A and 15B, exploded views of cable 1500 with mating devices in accordance with another additional embodiment of the present disclosure is shown. Cable 1500 may include a plurality of conductors which are formed through printed conductive traces on a flexible and non conductive substrate, such as paper, plastic, foam, rubber and the like. Cable 1500 may employ flexible circuit technology which allows deposition of conductors on a substrate similar to a printed circuit board whereby the substrate may be a thin, flexible material, such as plastic, paper, rubber, foam and the like. Cable 1500 may include an exterior covering which is a non conductive coating but may also include other types of exterior coverings. In one embodiment, mating device for cable 1500 may include a conductive base which may be configured to operate with a double-sided electrode pad whereby the cable 1500 and its mating device would couple to the double-sided electrode pad. Double-sided electrode pad may include a first pad, a second pad and a conductive plate between the first pad and second pad. The first pad and the second pad may include adhesive and conductive gel. A double-sided electrode pad may adhere to skin of a patient and a mating device of cable 1500. This may be advantageous a defective or non-sticking double-sided electrode pads may be easily replaced and cable 1500 may still be operable. Connector devices for connecting conductors of cable 1500 (not shown) may be configured to connect directly to an EKG machine, monitor, or may be configured to connect to a set of leads of an EKG machine or health monitoring device.

While cables have been described as telephone cable, ethernet cable and ribbon cable, it is contemplated that any type of cable utilizing any number of conductors may be employed without departing from the scope and intent of the present disclosure. It is contemplated that cable may include shielding, isolation and insulation for each conductor within a nonconductive exterior covering, including an exterior coating, of the cable. Cable may include one or more clips to allow attachment to a gurney, bed or the patient's clothing. Cable may further include an exterior coating which is light reflective and may glow in the dark to allow viewing my medical personnel in low light conditions. While cable may be formed of a flexible material, it is contemplated that cable may be latex free to prevent any undesirable reactions by those patients who may be allergic to latex products. Cable may be radiolucent. As a result, a cable may remain on when a patient is receiving an x-ray or similar image whereby presence of the cable may not distort the image.

While various types of connector devices, mating devices and cables have been shown in various examples of cable apparatus, it is contemplated that each example of connector devices, mating devices, and cables may be employed with other types and combinations of other connector devices, mating devices and cables. For example, a cable may include mating device 520 with other mating devices similar to mating device 720. Additionally, connector device 515 may be one type of connector device and cable 510 may include another type of connector device suitable for connecting with a set of leads for a monitor. Additionally, a mating device 520, 720 may be employed with cable 1300 which may include at least ten conductors. It should be understood also that various types of male/female connecting devices may be correspondingly swapped without departing from the scope and intent of the present disclosure. The various combination and sub-combination of elements may be combined, sub-combined and separated as desired for each application. Furthermore, cable may be employed for coupling directly with an EKG machine, another type of health monitoring device, or with a set of leads connected to an EKG machine and health monitoring device; cables may also be employed with other types of devices. Furthermore, it is contemplated the connector devices may be integrated within the cable itself and not necessarily require a separate device. Advantageously, cable may be produced in an efficient and low cost fashion which may allow disposal of the cable after a single use and may prevent the transmission of disease and infection as possible with re-use of a conventional set of leads of an EKG machine. In an alternative embodiment, cable may be produced for multiple uses and may be gas sterilizable.

Figure 16C:
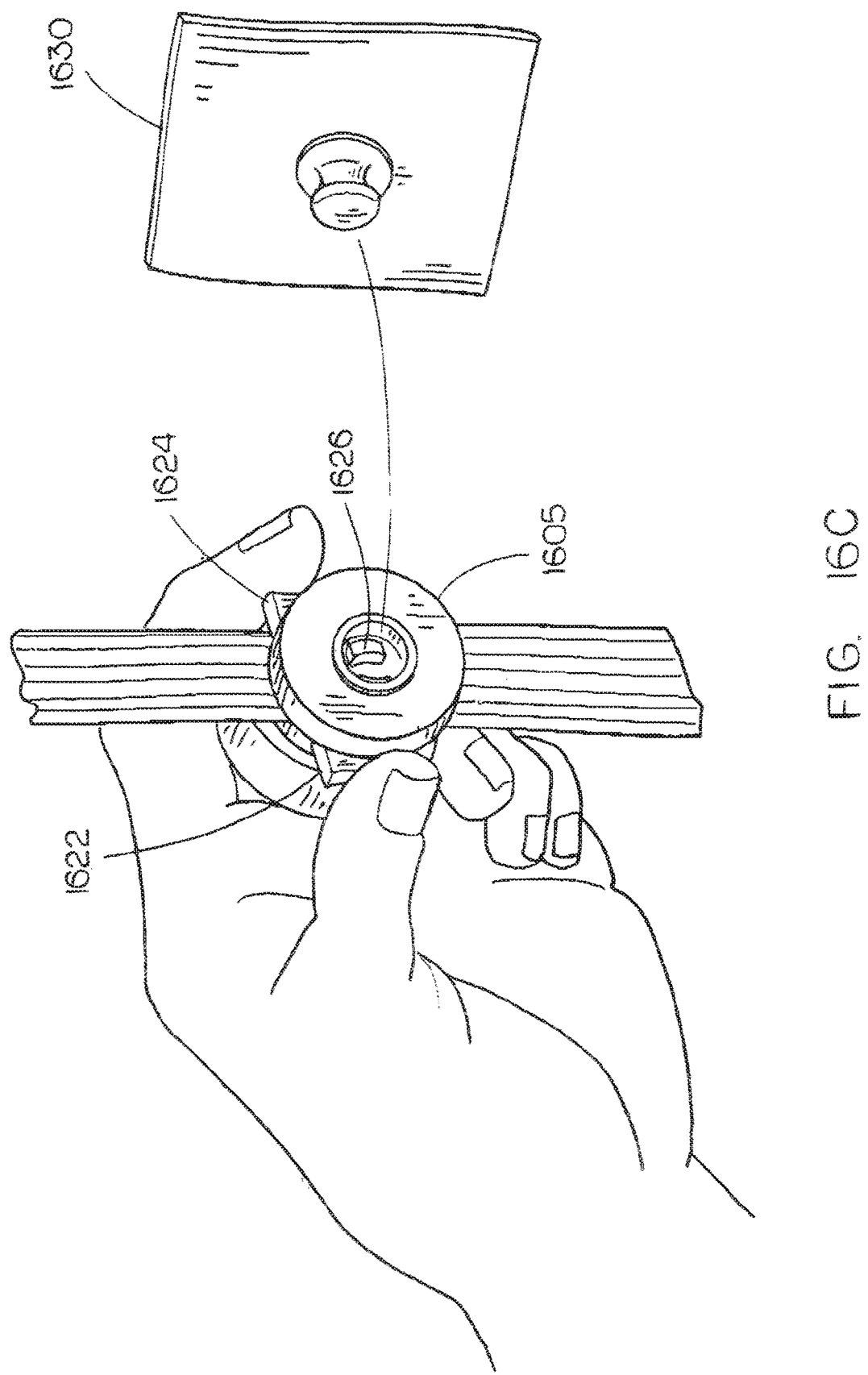

Referring to FIGS. 16A, 16B and 16C, exploded views of mating devices associated with a cable in accordance with an embodiment of the present disclosure are shown. In FIGS. 16A and 16 B, mating device 1605 may include a removable cover 1610. When mating device 1605 is in use, removable cover 1610 may be placed in a stored position and mating device 1605 may be coupled with an electrode pad. However, when mating device 1605 is not is use, removable cover 1610 may be placed on a connecting portion of the mating device, such as on the female receptacle of the snap connector. Advantageously, this may prevent interference and may protect mating device 1605. This may be particularly useful in situations where there may be a ten-conductor cable and only five conductors are currently in use, thus the mating devices associated with the non-used mating devices may include removable covers in the covered position. It is contemplated that the removable cover 1610 may be formed of silicone and other non-conducting materials. Other types of removable covers may also be utilized with the mating devices without departing from the scope and intent of the present disclosure.

Referring to FIG. 16C, mating device 1605 may include a clasp mechanism 1620 to provide a zero insertion force mechanism with the snap connector. Clasp mechanism may be a mechanical clasp which, for example, its tabs 1622, 1624 are pressed inward towards mating device 1605, causes an internal pin 1626 to retract from the female receptacle. When the mating device is placed on a male plug of electrode pad 1630 and released, internal pin may be extended and may secure the mating device 1605 to the electrode pad 1630. In such a fashion, mating device 1605 may be connected with an electrode pad 1630 without providing any force upon the electrode pad 1630. This may be particularly useful in situations where a patient may have a blunt force injury to the torso causing pain to the patient. By allowing the mating device to be connected to the electrode pad without any force applied to the electrode pad, a patient may be spared from additional pain. While FIG. 16C discloses one type of clasp mechanism for providing a zero insertion force snap connector, various types of zero insertion force mechanisms may be utilized without departing from the scope and intent of the present disclosure.

Connector Device

Figure 17:
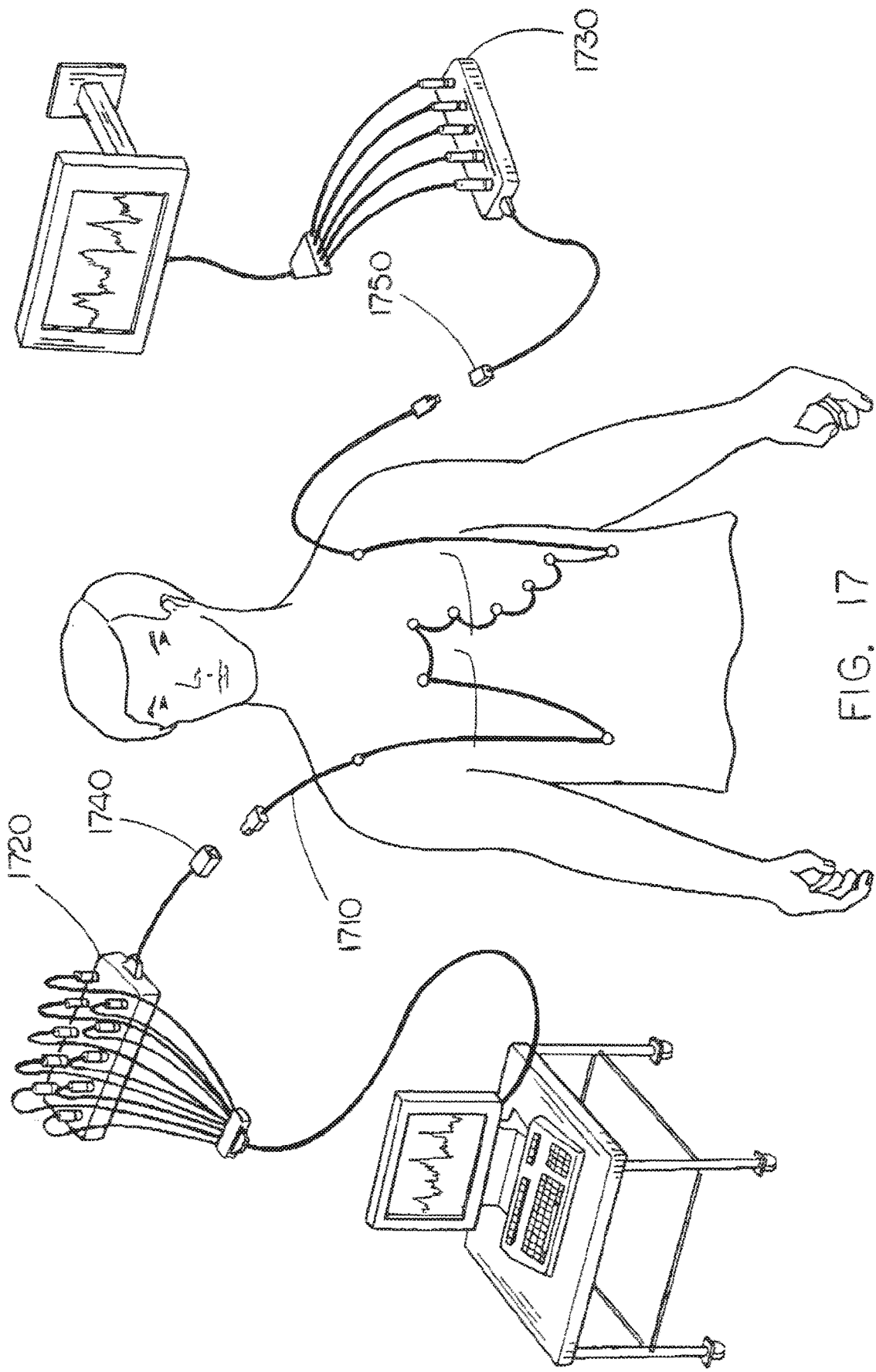
FIG. 17 depicts a cable apparatus and connector devices for coupling with various medical devices in accordance with an embodiment of the present disclosure.

Referring to FIG. 17, a cable apparatus and connector devices for coupling with various medical devices in accordance with an embodiment of the present disclosure are shown. For example, cable 1710 including a plurality of mating devices may be placed on an individual. Connector devices 1720, 1730 may allow connection of the cable 1710 to an EKG machine or monitor, respectively. Connector devices 1720, 1730 may connect with a plurality of male plugs from a set of leads by a plurality of jacks or other suitable devices for receiving plugs. Connector devices may further include connectors 1740, 1750 which allow quick attachment with a corresponding connector connected at each end of cable 1710. Advantageously, connector devices 1720, 1730 may allow quick attachment and detachment to various medical devices without a requirement of replacement of cable 1710.

Figure 18:
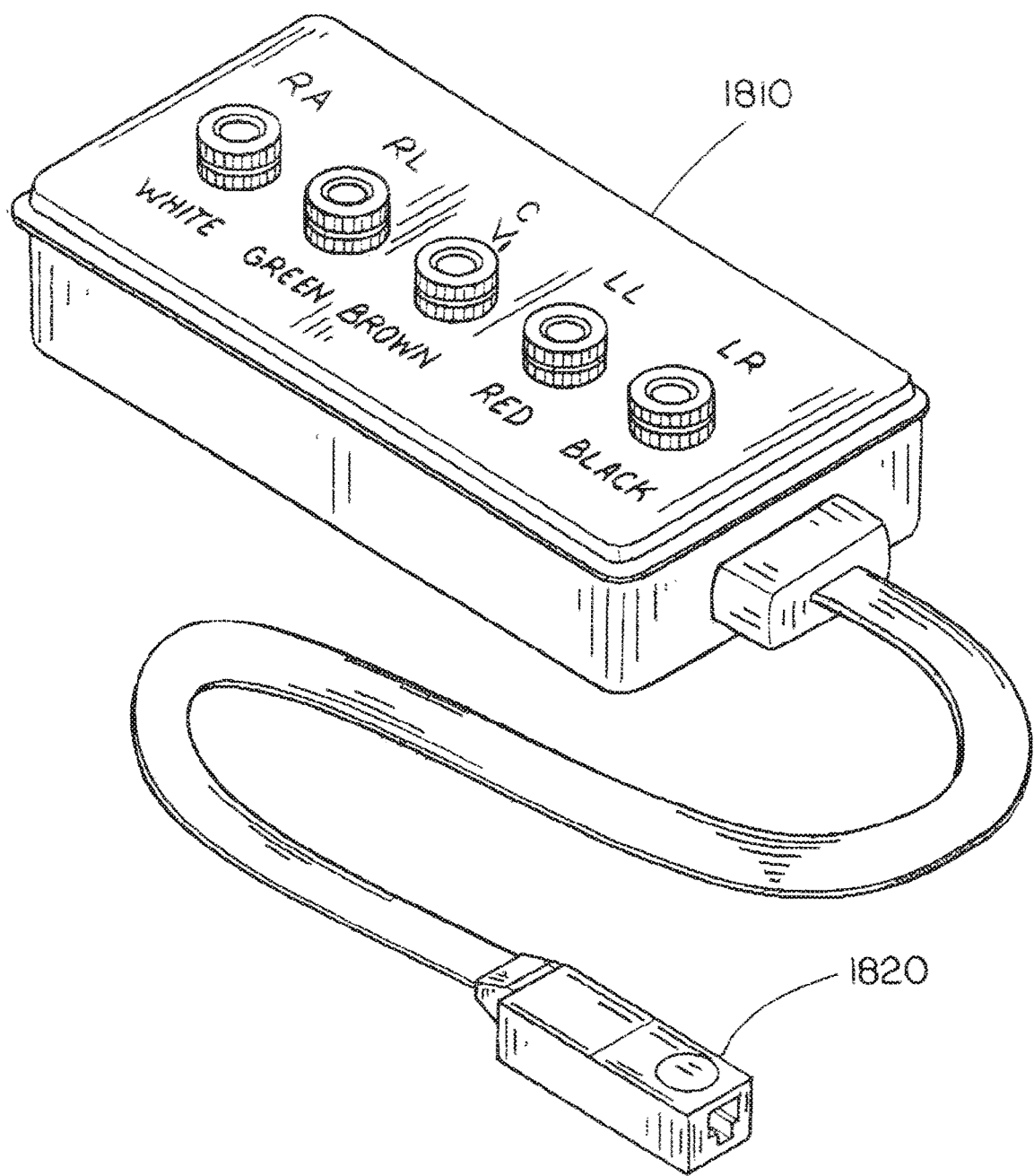
FIG. 18 depicts an exploded view of a connector device in accordance with an embodiment of the present disclosure.

Referring to FIG. 18, an exploded view of a connector device 1810 in accordance with an embodiment of the present disclosure is shown. Connector device 1810 may be representative of connector devices 1720, 1730 as shown in FIG. 17. Connector device 1810 may include a plurality of jacks for receiving plugs associated with a set of leads from an EKG machine or medical monitoring device. Connector device 1810 may further include labels and color codes associated with each jack to ensure each lead of a set of leads is properly connected with connector device 1810. Connector device 1810 may further include a connector 1820. Connector 1820 may be a telephone jack, Ethernet jack, or other types of jacks for receiving a corresponding plug which may be coupled with an end of a cable. While connector device 1810 includes a plurality of jacks, it could also include a plurality of male plugs for receiving female receptacles of snap connectors. Connector device 1810 may also include a plurality of posts suitable for connecting with alligator clips connected with a set of leads. It is contemplated that other types of connections could also be employed for coupling with a cable including a plurality of mating devices without departing from the scope and intent of the present disclosure.

Figure 19:
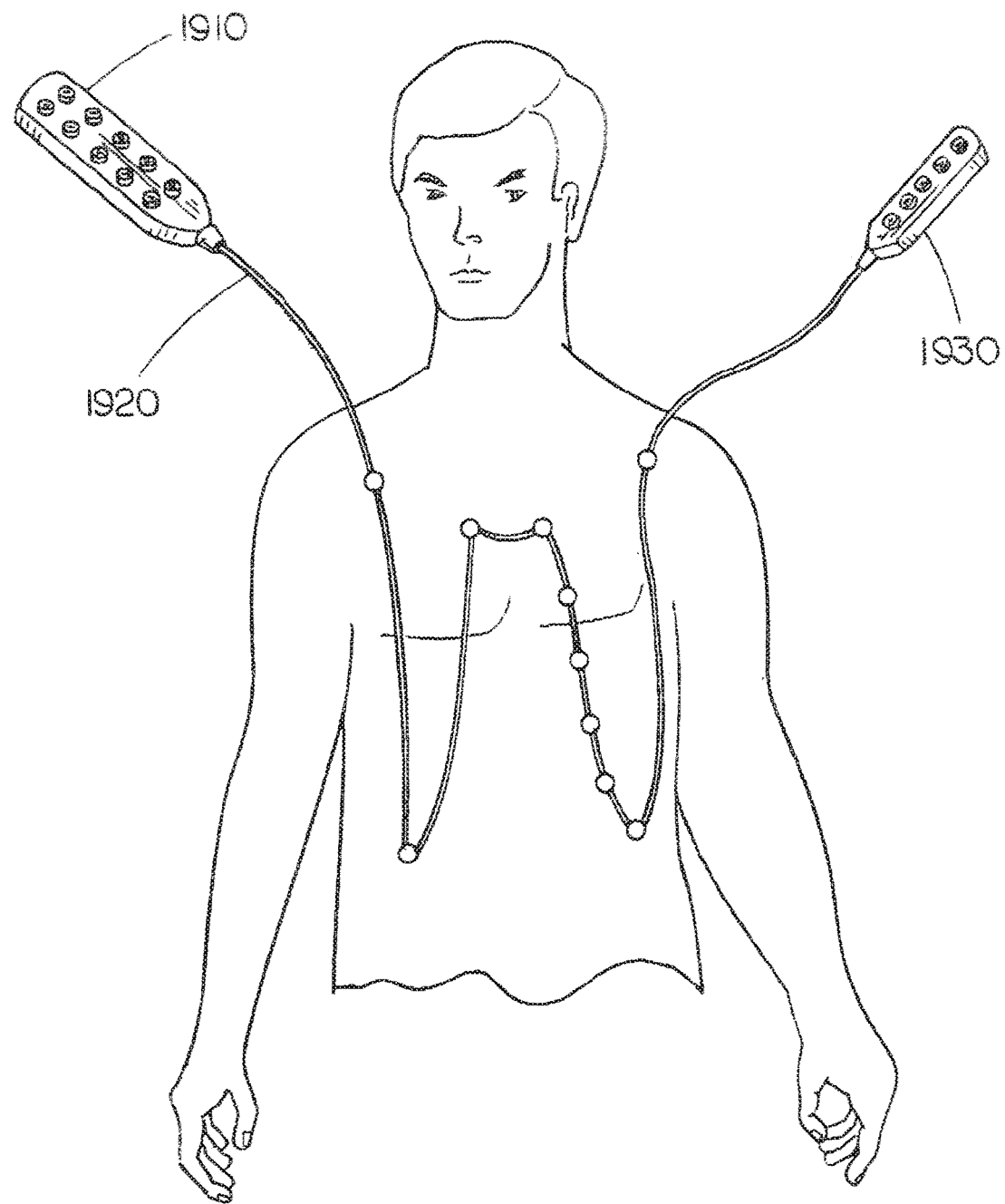
FIG. 19 depicts an integrated cable apparatus and connector devices for coupling with various medical devices in accordance with an alternative embodiment of the present disclosure.
Figure 20:
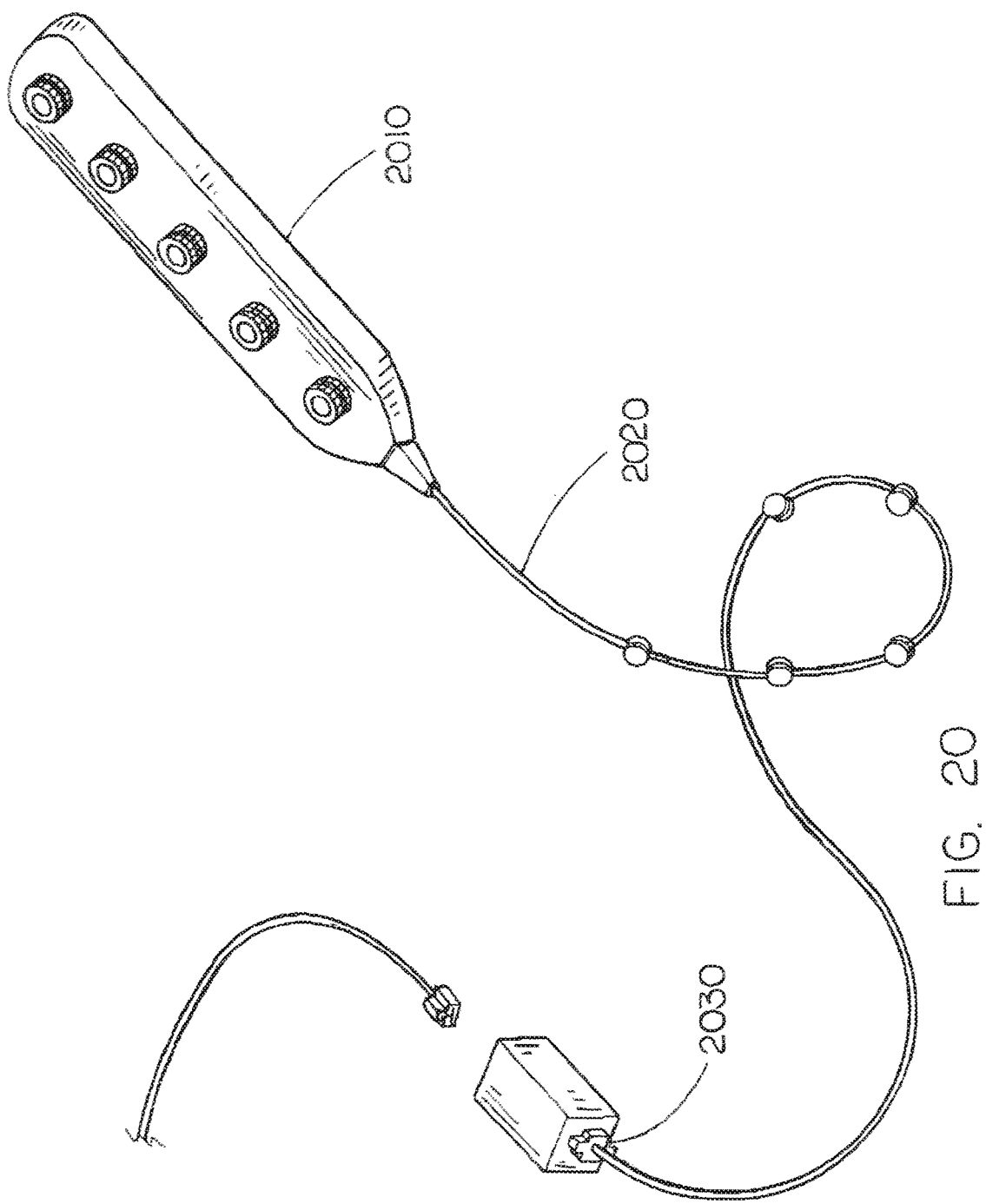
FIG. 20 depicts an exploded view of a cable apparatus and connector device in accordance with an another embodiment of the present disclosure.

Referring to FIG. 19, an integrated cable apparatus and connector devices for coupling with various medical devices in accordance with an alternative embodiment of the present disclosure is shown. In one embodiment, a first connector device 1910, a cable 1920 with a plurality of mating devices and a second connector device 1930 may be formed as a single integrated unit. As such, first connector device 1910 or second connector device 1930 may directly couple to a set of leads associated with an EKG machine or other type of medical monitoring device. In FIG. 20, an integrated cable apparatus and a single connector device for coupling with various medical devices in accordance with an alternative embodiment of the present disclosure is shown. Connector device 2010 may be fixedly coupled with cable 2020. On another end of cable 2020, a connector 2030 may be coupled with cable 2020 to allow attachment to another connector device (not shown) and then ultimately coupled to another medical device if desired.

Figure 21A:
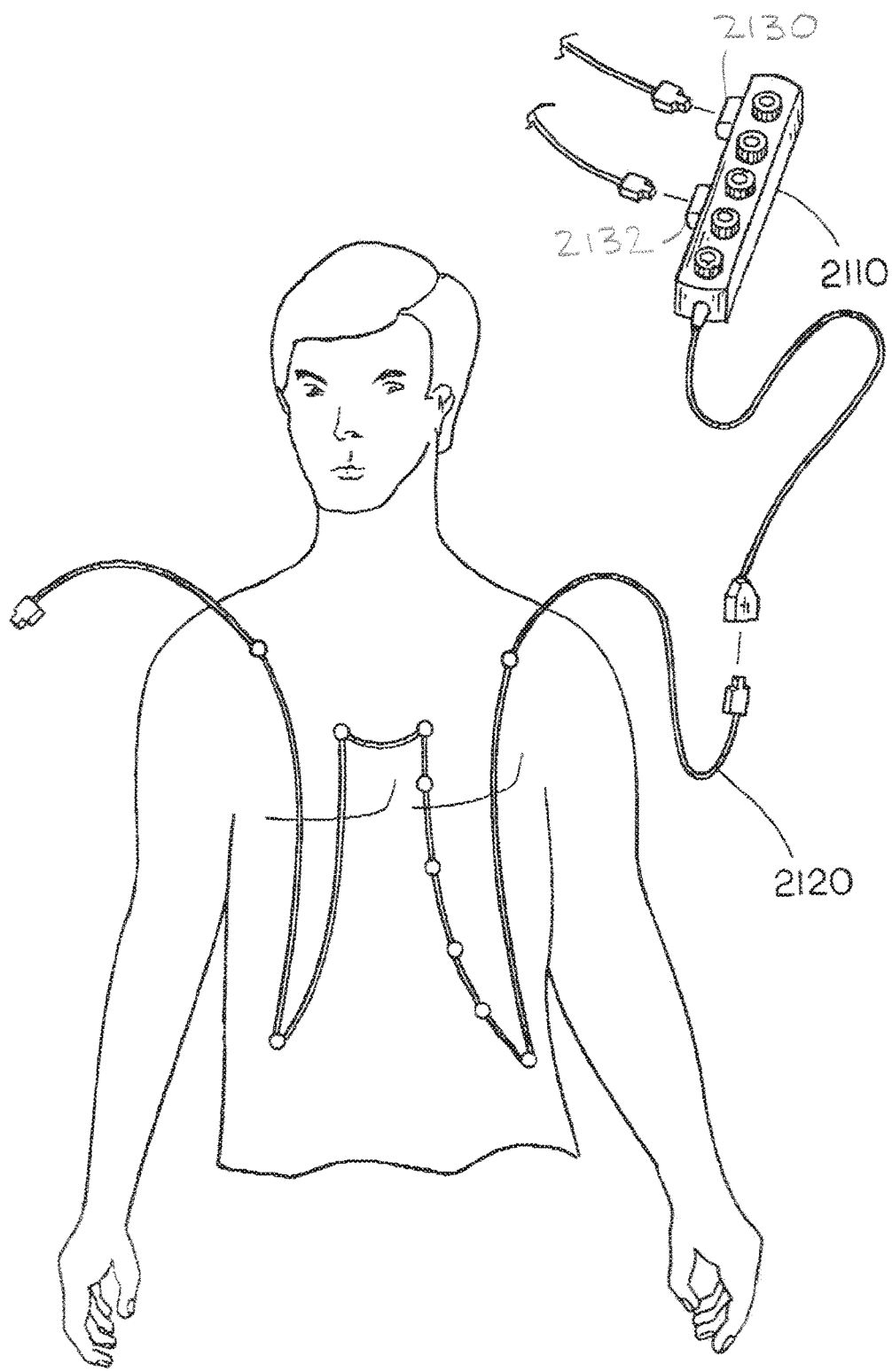
FIGS. 21A and 21B depict views of a cable apparatus and connector device in accordance with various embodiments of the present disclosure.
Figure 21B:
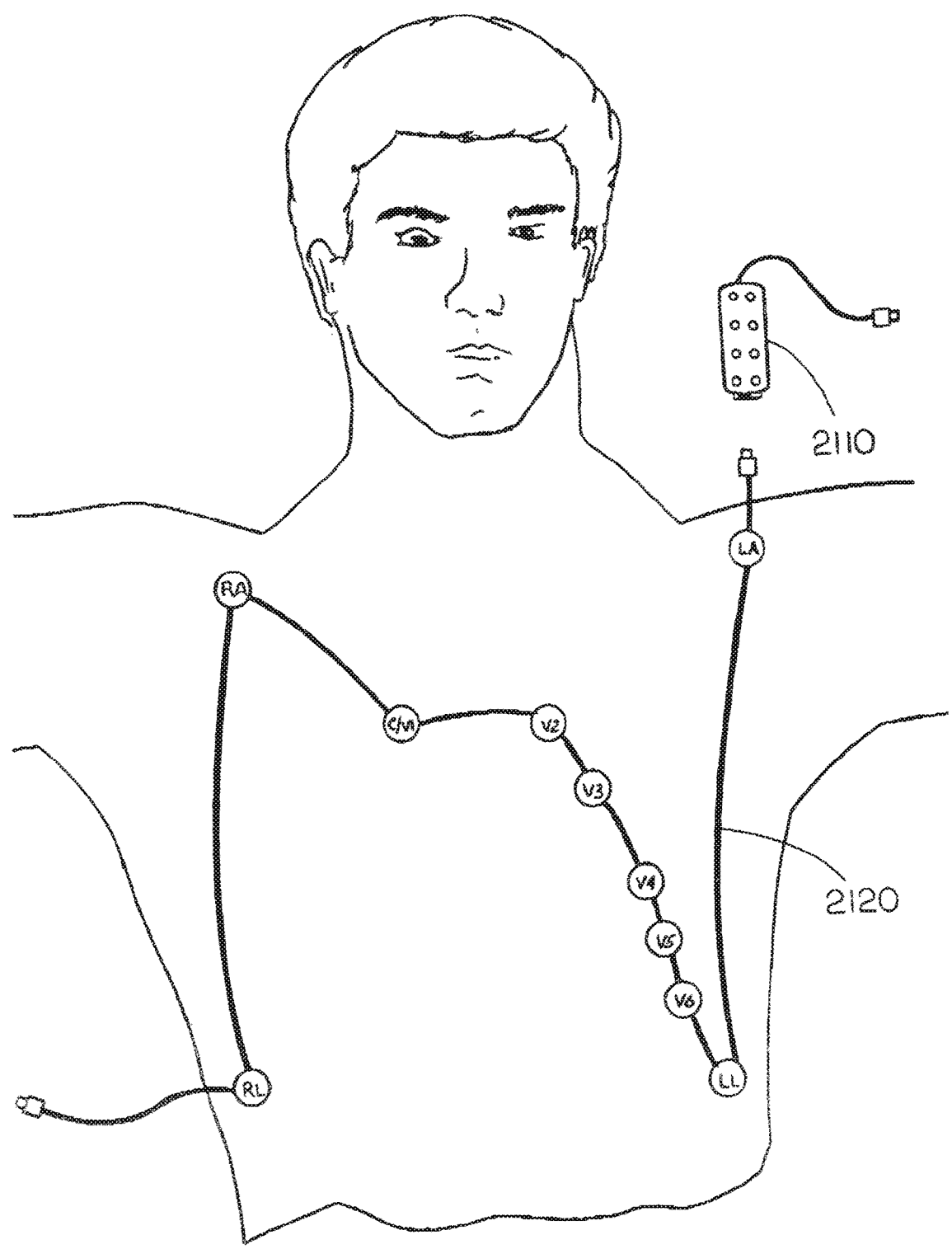

FIGS. 21A and 21B depict views of a cable apparatus and connector device in accordance with various embodiments of the present disclosure. In FIG. 21A, connector device 2110 may be configured to be coupled with cable 2120. Connector device 2110 may include additional ports 2130, 2132. Additional ports may allow attachment to various other medical devices, other cables and the like. Cable 2120 may be a length and configured for placement upon a patient to allow ending of the cable in proximity to the top right shoulder area of the patient. In FIG. 21B, connector device 210 may be connected with cable 2120. Cable 2120 may be configured to be a shortest length as possible. Cable 2120 may be configured for a "N" style placement and an end of cable 2120 be lower right abdomen area.

Figure 22:
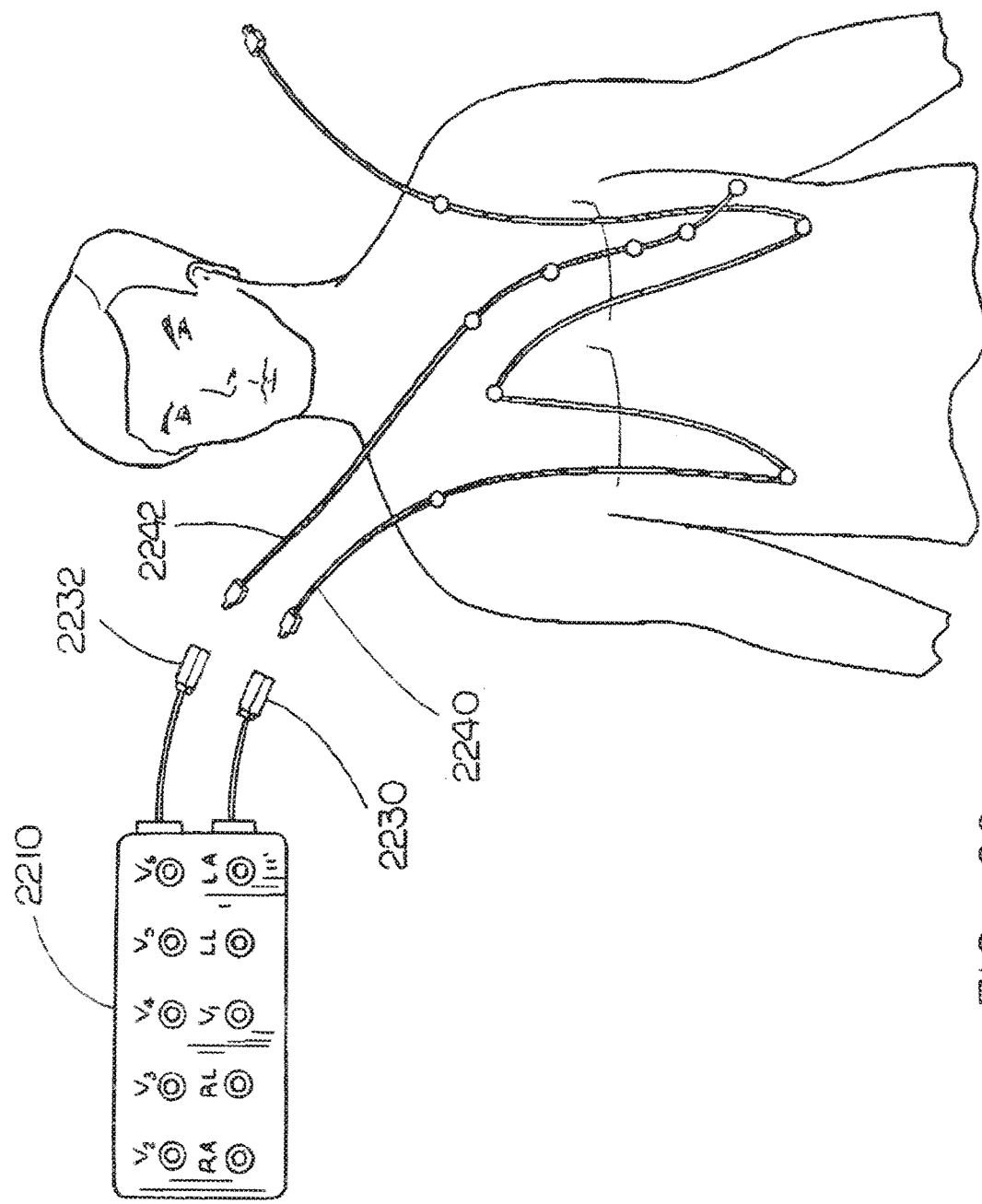
FIG. 22 depicts a view of a connector device and multiple cables in accordance with an embodiment of the present disclosure.
Figure 23:
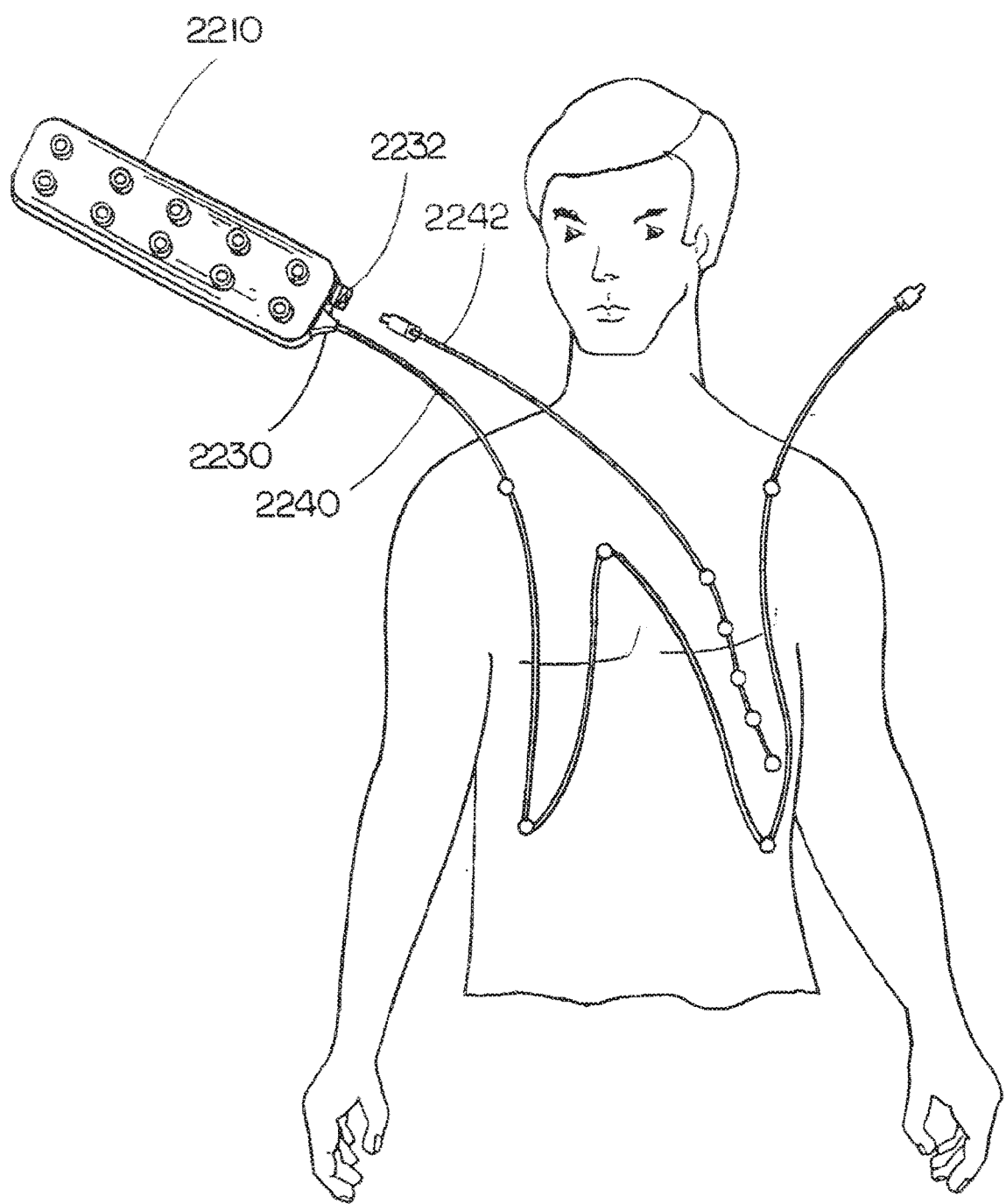
FIG. 23 depicts a view of a connector device and multiple cables in accordance with another embodiment of the present disclosure.

Referring to FIGS. 22 and 23, a view of a connector device and multiple cables in accordance with an embodiment of the present disclosure is shown. Connector device 2210 may include two sets of five jacks for receiving a set of leads from one or multiple medical monitoring devices. Connector device 2210 may also include two connectors or output ports which are configured to be connected with cables. For example, connectors or output ports 2230, 2232 may be configured to be coupled with cable 2240, 2242 respectively. It is contemplated that connector device 2210 may be operable for a five-lead cable and may be suitable for a monitoring operation. However, an additional cable may be added to provide ten total points of observation on a patient suitable for an EKG test.

Figure 24:
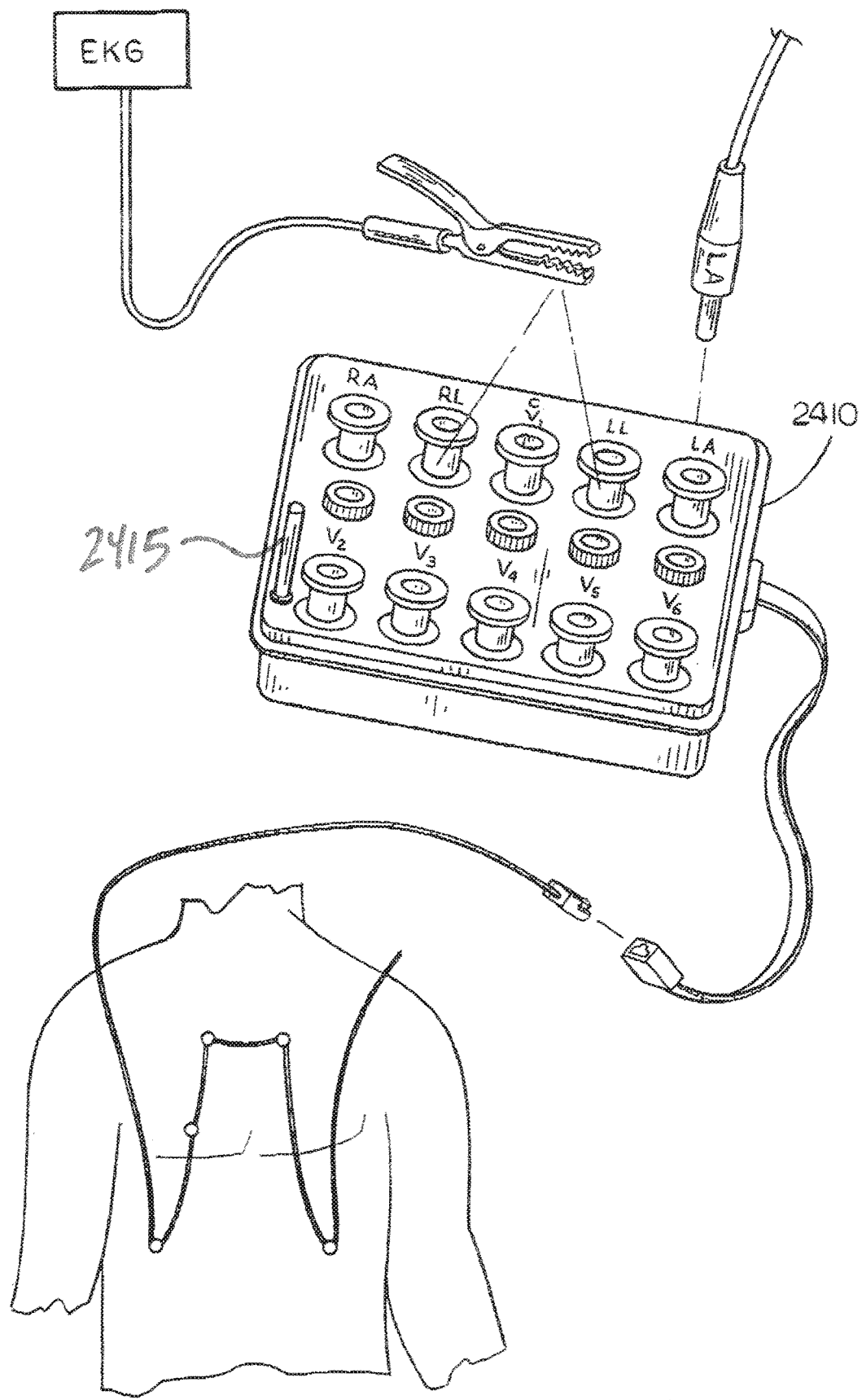
FIG. 24 depicts an exploded view of a connector device in accordance with another embodiment of the present disclosure.

Referring to FIG. 24, an exploded view of a connector device 2410 in accordance with another embodiment of the present disclosure is shown. Connector device 2410 may be configured to be coupled with various types of connectors associated with a set of leads from an EKG machine or medical monitoring device, including plugs, alligator clips and the like. While not shown, connector device 2410 may further include male plugs configured to be coupled with a set of female snap receptacles associated with a set of leads for an EKG machine or medical monitoring device. Connector device may also include one or more posts 2415 which may be more suitable for connecting with alligator clips associated with a set of leads.

In another embodiment of the disclosure, connector device 2410 may include a wireless transceiver. Wireless transceiver may transmit and receive electrical signals measured by mating devices associated with a cable coupled to connector device 2410. It is contemplated that medical monitoring devices such as EKG devices may also include wireless receivers whereby the electrical signals measured by mating devices of cable may be transmitted by a wireless transceiver associated with connector device 2410 to another wireless transceiver associated with a medical monitoring device. In one embodiment of the disclosure, wireless transceiver may be a BLUETOOTH wireless transceiver.

Advantageously, with various ways to connect with any type or style of a set of leads associated with any type or style of a medical monitoring device, connector device 2410 may operate as a universal connector device. As such, connector device 2410 may be operable with a variety of types of EKG machines and medical monitoring devices which utilize different types of connectors for the set of leads.

Figure 25:
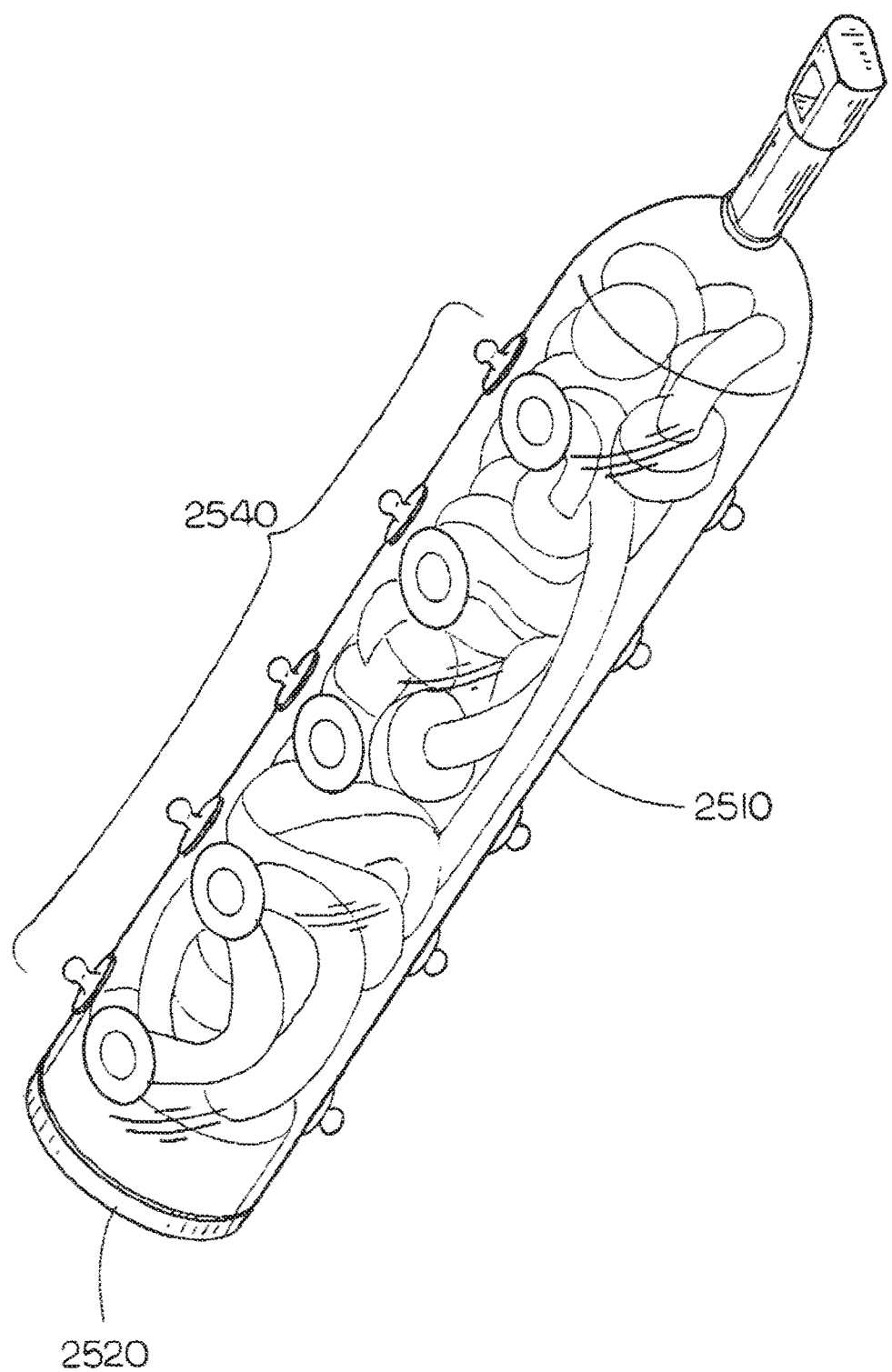
FIG. 25 depicts a cable apparatus and connector device included within a self-contained package in accordance with an embodiment of the present disclosure.
Figure 26:
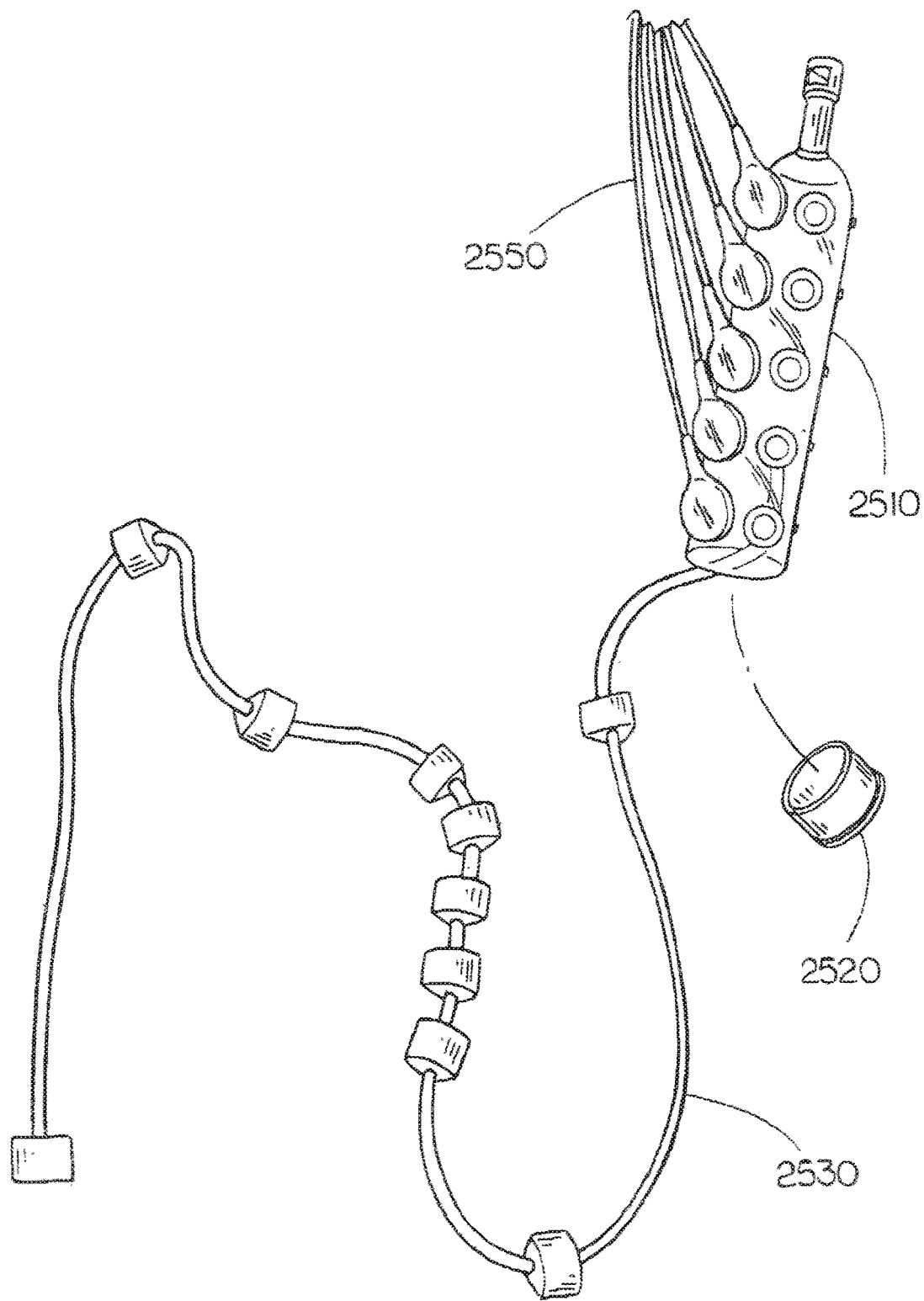
FIG. 26 depicts a cable apparatus and connector device included within a self-contained package with the cable apparatus extended out of the package in accordance with an embodiment of the present disclosure.

Referring to FIG. 25, a cable apparatus and connector device included within a self-contained package in accordance with an embodiment of the present disclosure is shown. FIG. 26 depicts a cable apparatus and connector device included within a self-contained package with the cable extended out of the package. Package 2510 may include a removable cover 2520 which may be removed and allow access to cable 2530. Package 2510 may further include a set of connectors 2540, for example, a set of male plugs suitable for connecting with a set of female snap receptacles 2550 from a set of leads connected to a medical monitoring device. Connector device 2560 may allow additional connection to a monitoring device.

Figure 27A:
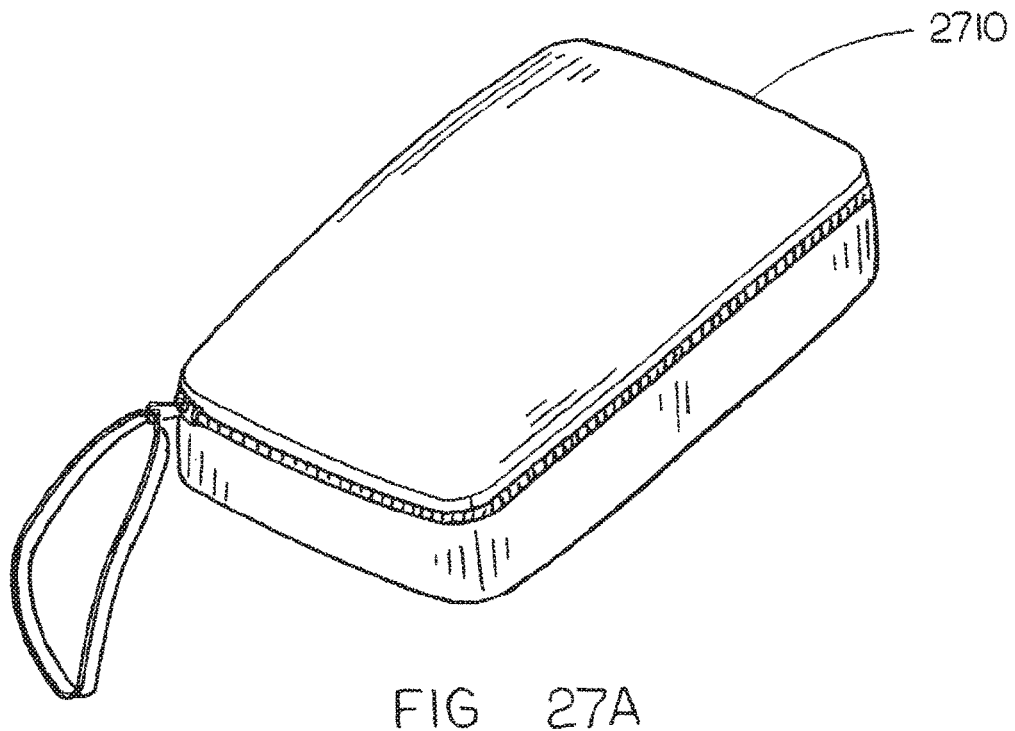
FIGS. 27A and 27B depict a cable apparatus and connector device included within a self-contained package in accordance with another embodiment of the present disclosure.
Figure 27B:
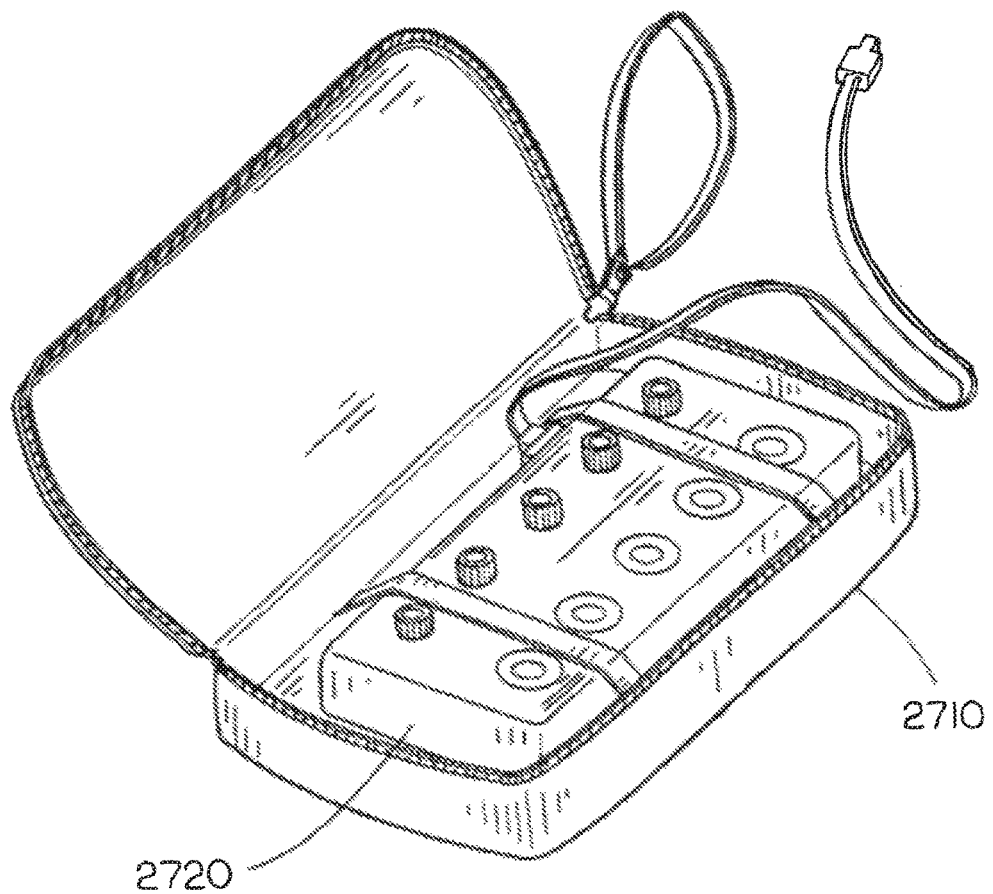

Referring to FIGS. 27A and 27B depict a cable apparatus and connector device included within a self-contained package in accordance with another embodiment of the present disclosure. Package 2710 may include a re-fastenable cover, such as a zipper, which may allow access to a connector device 2720. Package 2710 may allow easier transport and more organized use of the cable apparatus of the present disclosure. It is further contemplated that package 2710 may include removable attachment device configured to attach the package to the bed or gurney of a patient to provide better organization in an ambulance or emergency room environment.

Figure 28:
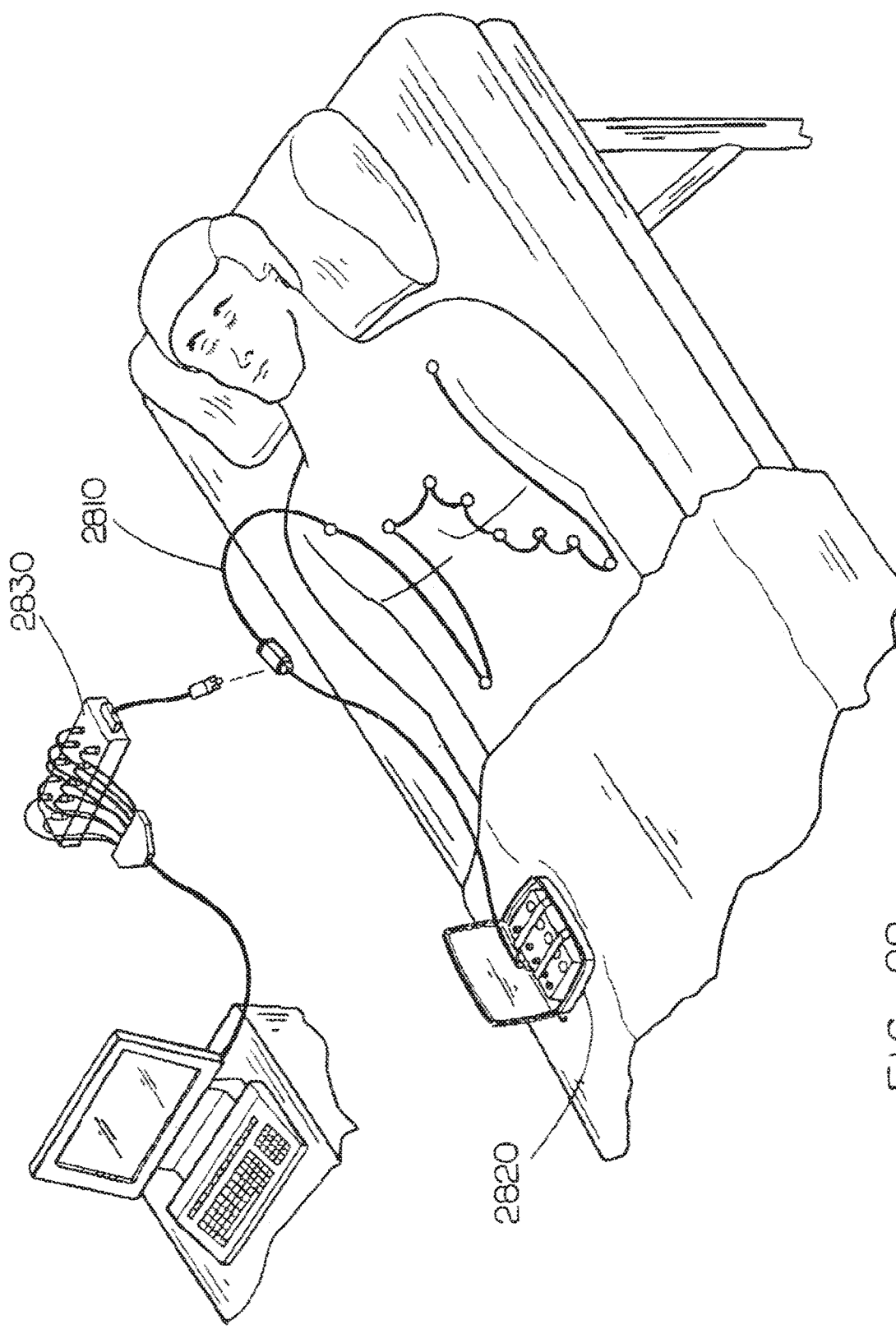
FIG. 28 depicts multiple connector devices suitable for operation with a utilized cable in accordance with another embodiment of the present disclosure.
Figure 29:
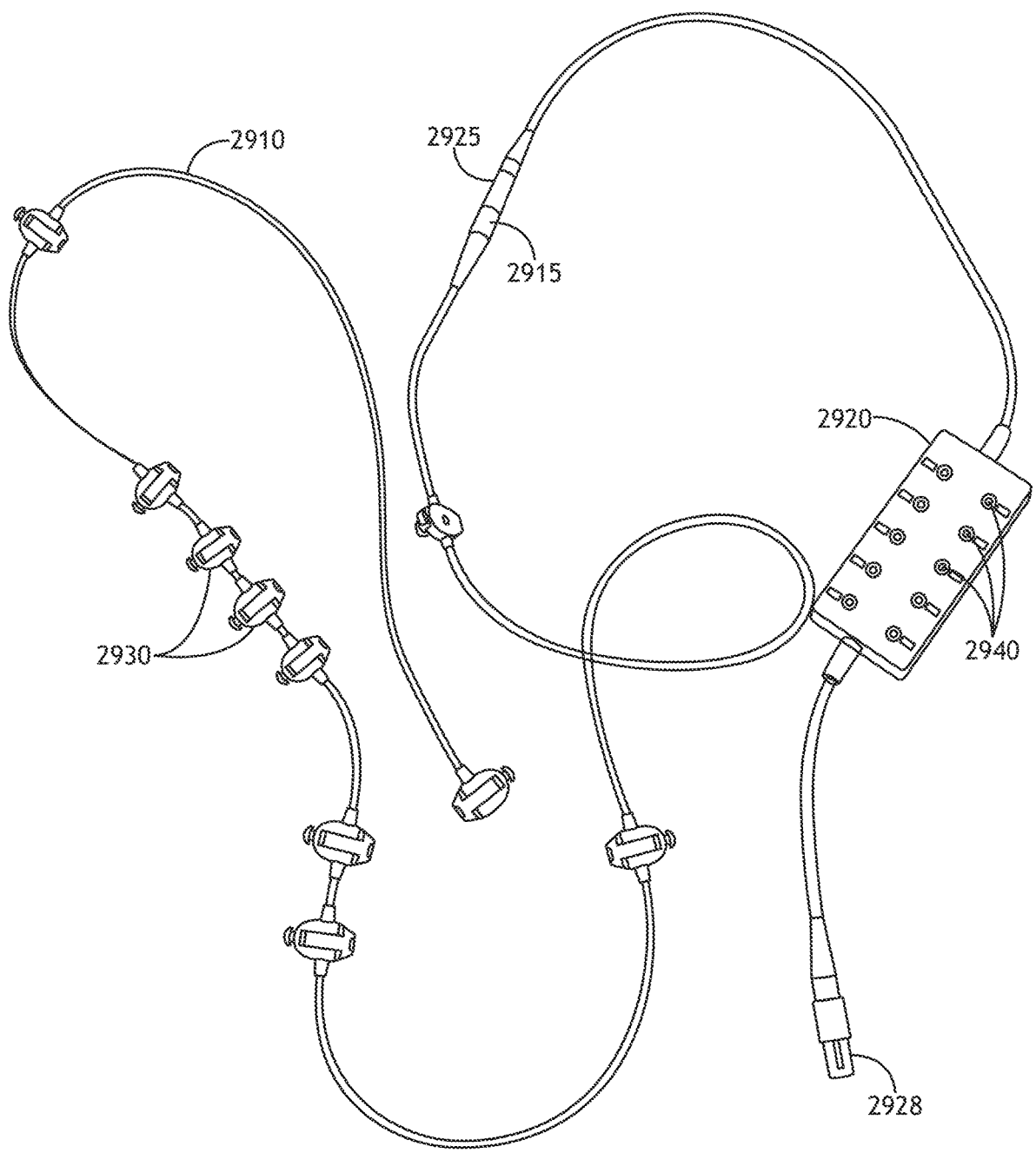
FIG. 29 depicts a cable apparatus including one or more mating devices along with a connector device in accordance with another embodiment of the present disclosure.

Referring to FIG. 28, multiple connector devices suitable for operation with a utilized cable in accordance with another embodiment of the present disclosure is shown. It is contemplated that in many emergency situations, medical personnel associated with an ambulance service, such as paramedics or EMTs, may have medical monitoring equipment and thus may place a cable 2810 with a plurality of mating devices upon the torso of a patient as previously described. A first connector device 2820 may be coupled to cable 2810 to couple with a medical monitoring device, such as a portable device located within the ambulance. Upon arrival at an emergency room, cable 2810 may remain on the patient and cable 2810 may be disconnected from first connector device 2820 and then connected to a second connector device 2830. It is contemplated that second connector device 2830 may be coupled with a medical monitoring device, such as an EKG machine associated with the emergency room. First connector device 2820 may be removed and may be returned to the ambulance by the medical personnel associated with the ambulance while the cable 2810 is left with the patient. Cable 2810 may also connect to monitor 2840 via a plurality of conventional set of leads 2850 via a connector device 2860. Advantageously, medical personnel with the emergency room may quickly obtain patient information without a requirement of spending time applying each lead of a set of leads in the conventional setting as depicted in FIG. 1.

Figure 30:
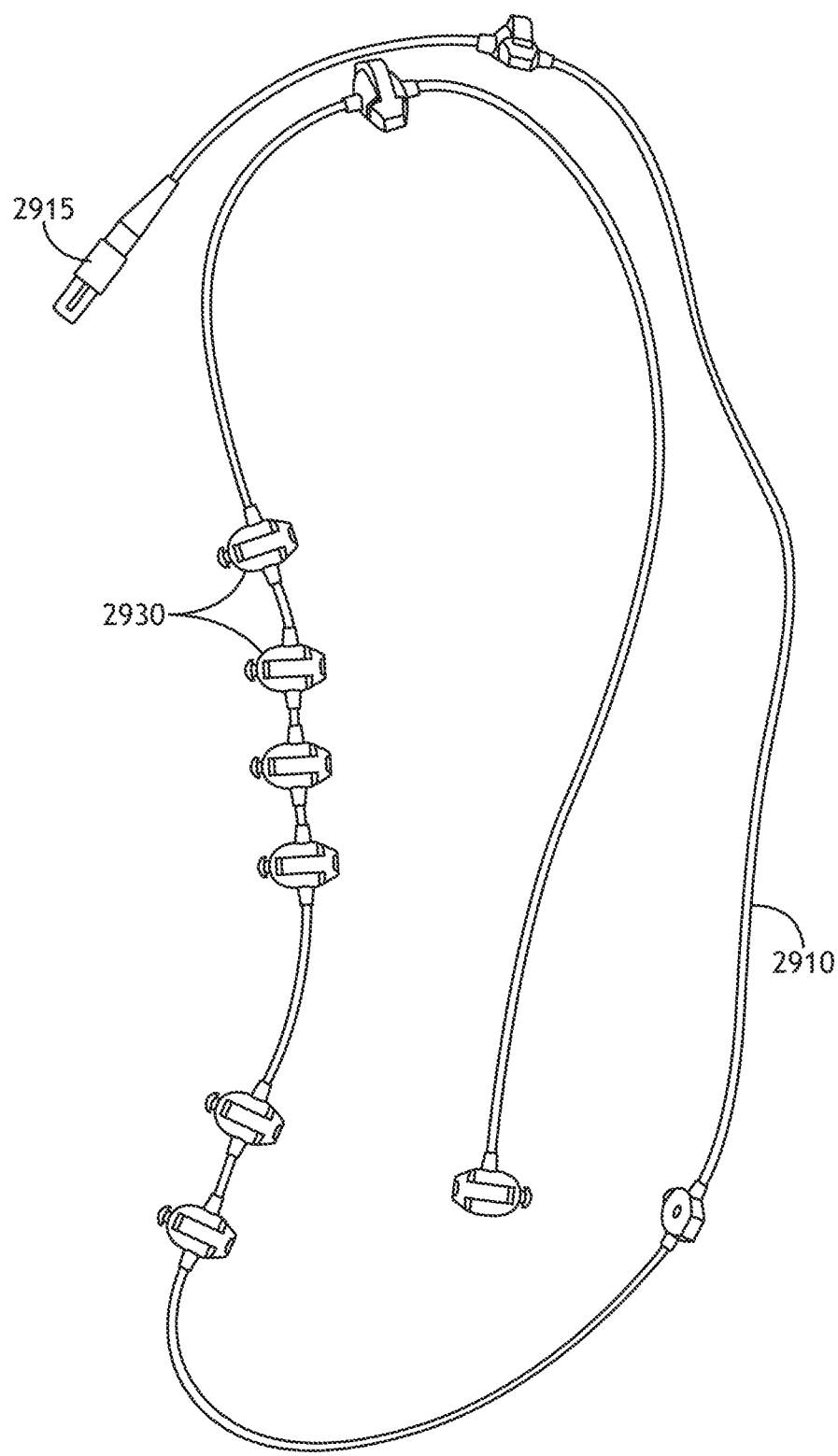
FIG. 30 depicts a cable apparatus including mating devices in accordance with another embodiment of the present disclosure.

Referring to FIGS. 29 through 39, a cable apparatus 2910 and a connector device 2920 including one or mating devices 2930 is shown in accordance with one or more additional alternative embodiments of the present disclosure is shown. Referring to FIGS. 36A and 36B, an exploded view of the connector device 2920 is shown. FIG. 30 depicts the cable apparatus 2910 while FIGS. 33A-35E depict exploded views of the mating device 2930 associated with the cable apparatus 2910.

Figure 36A:
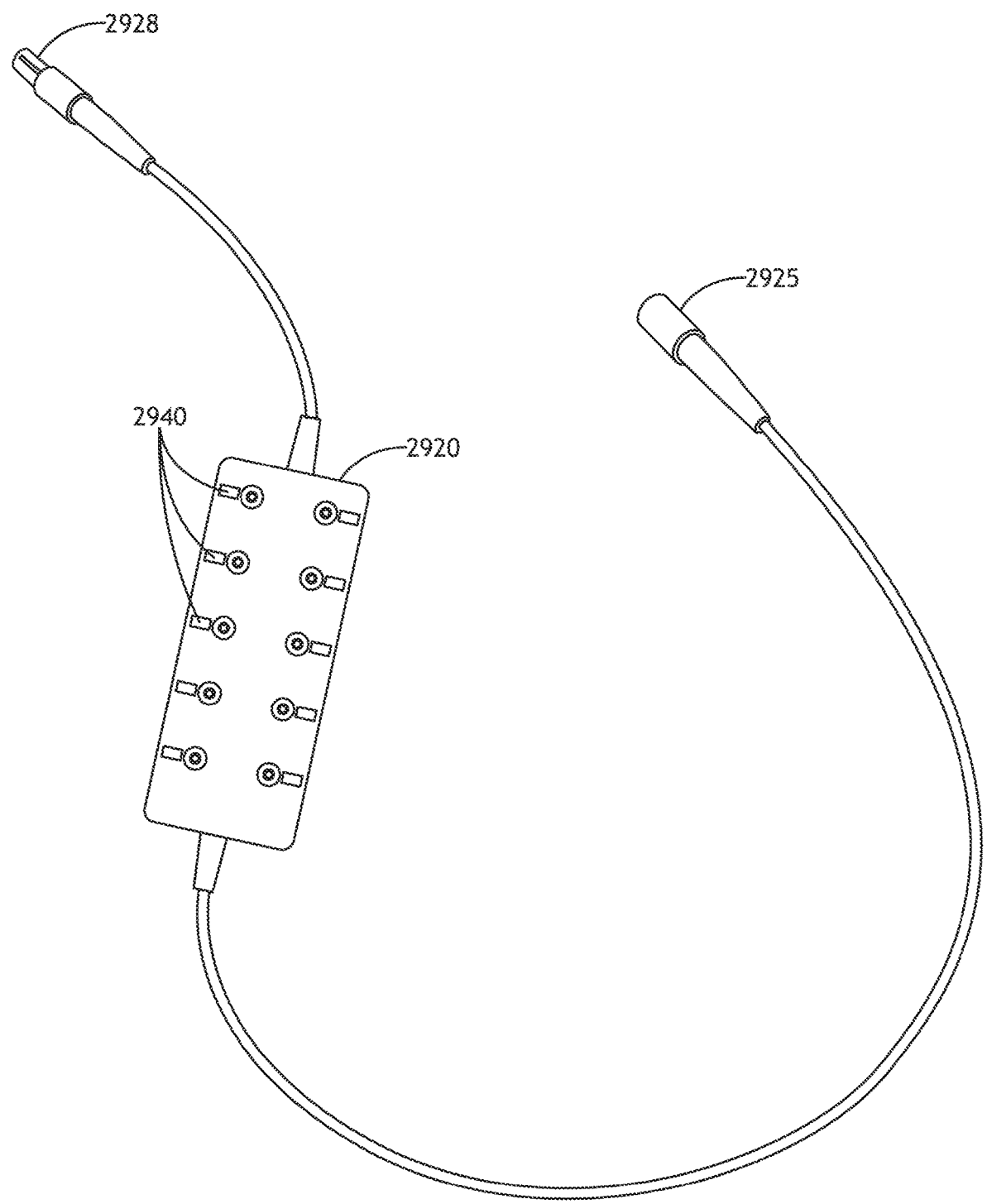
FIGS. 36A and 36B depict a connector device in accordance with another embodiment of the present disclosure.
Figure 36B:
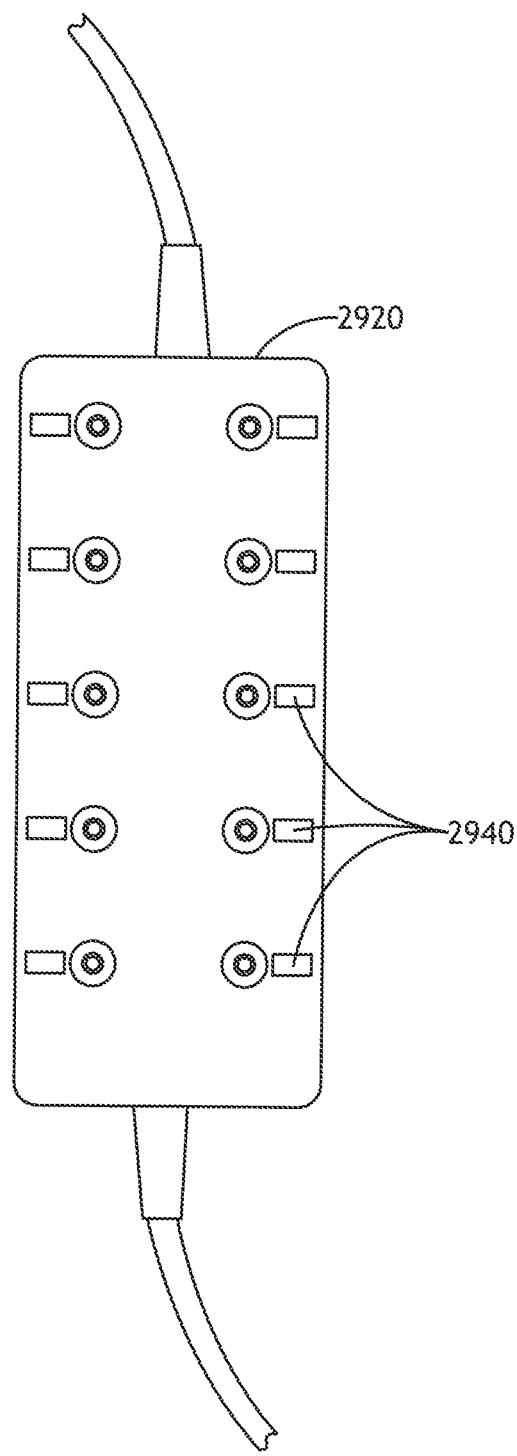
Figure 37:
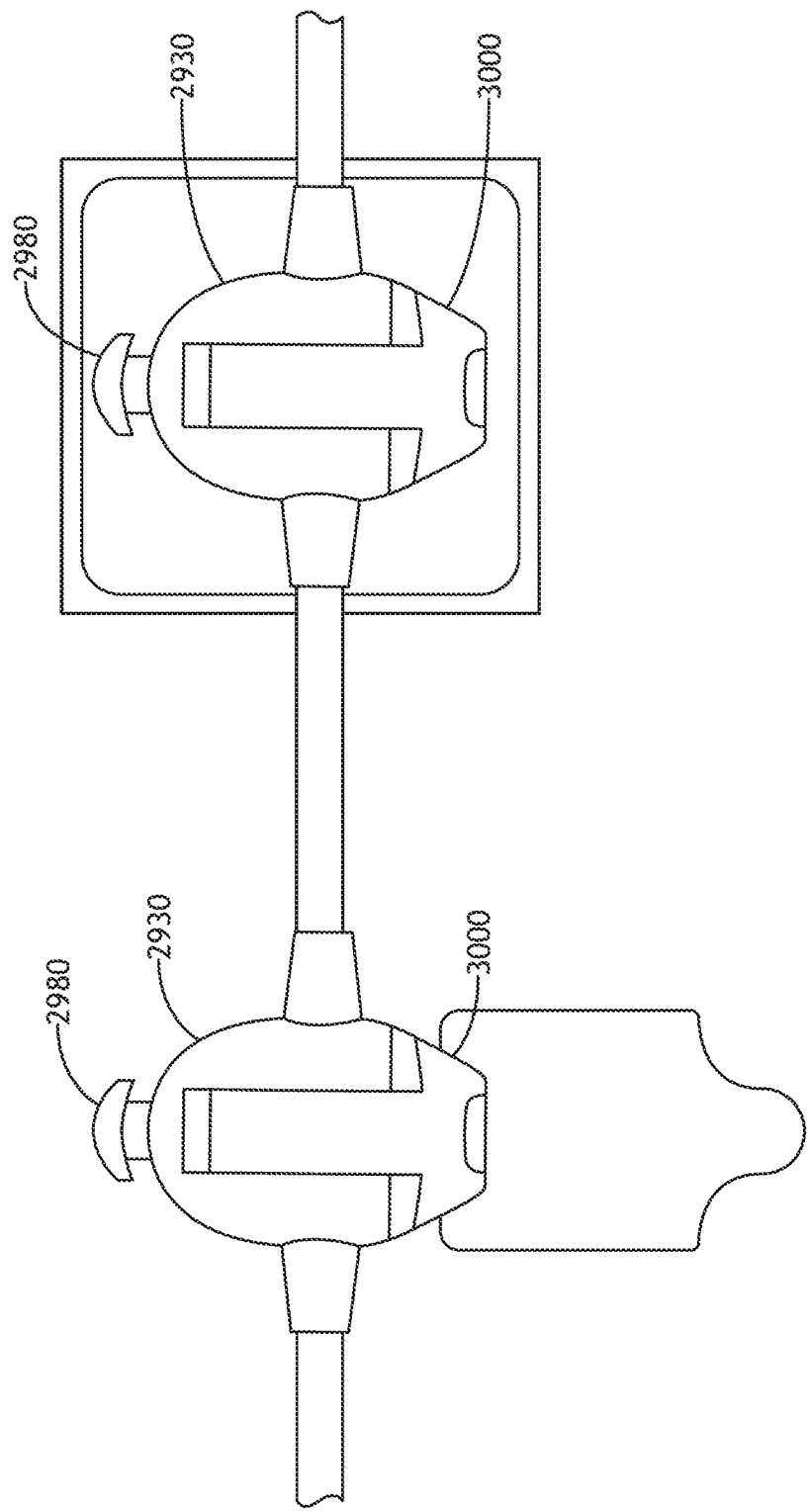
FIG. 37 depicts a cable apparatus include mating devices connected to different types of electrodes in accordance with another embodiment of the present disclosure.
Figure 38A:
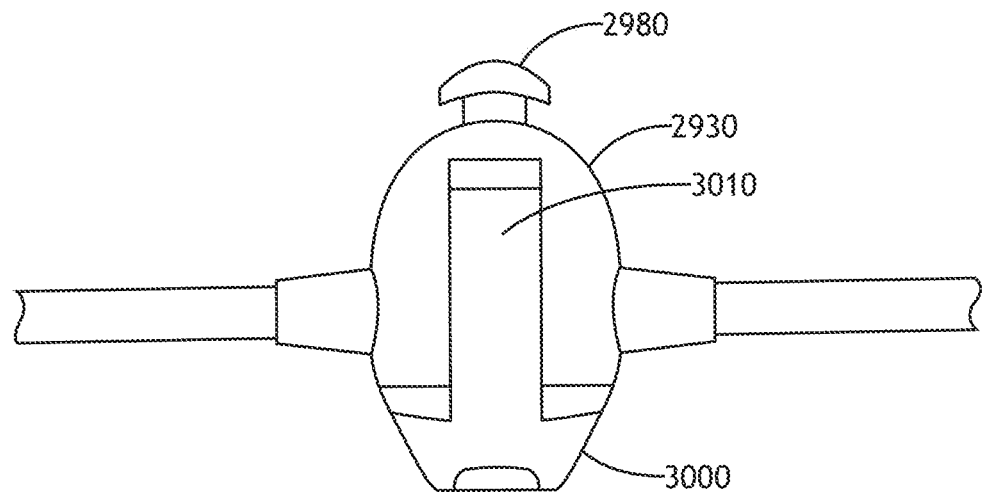
FIG. 38A depicts a top down view of a mating device in accordance with another embodiment of the present disclosure.
Figure 38B:
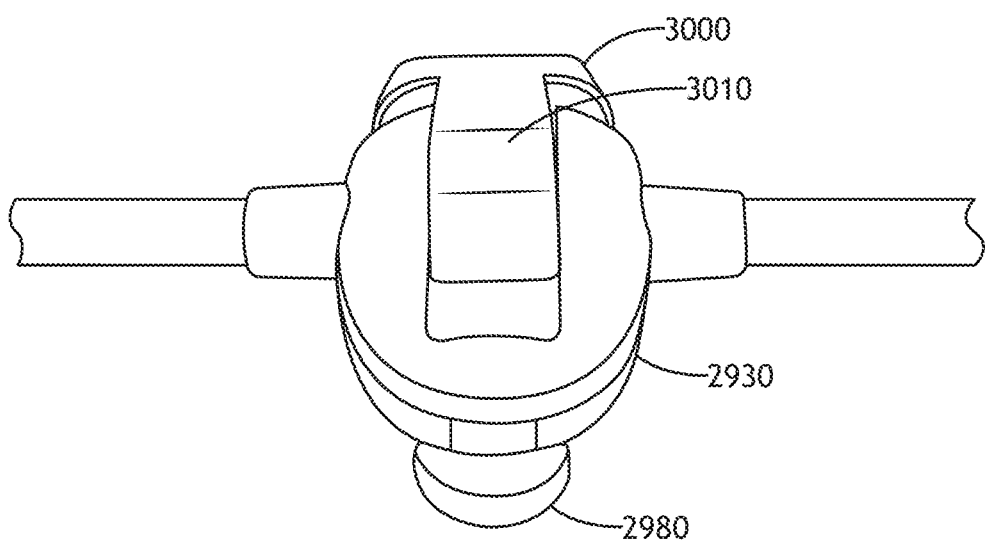
FIG. 38B depicts a rear view of a mating device in accordance with another embodiment of the present disclosure.
Figure 38C:
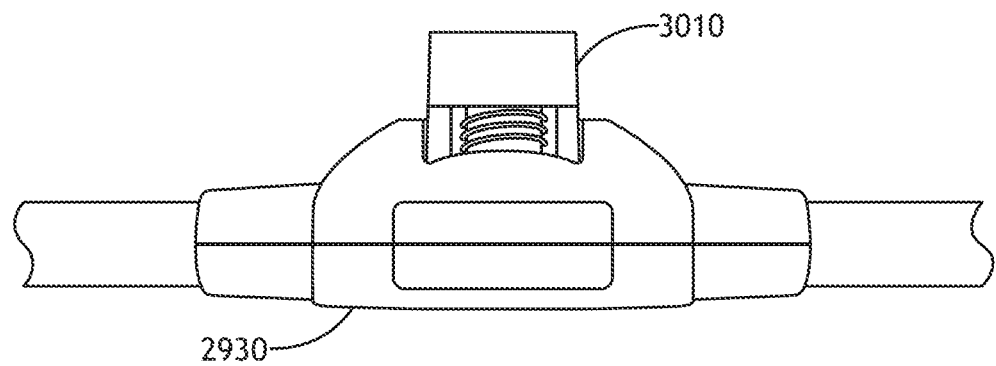
FIG. 38C depicts a top-rear view of the mating device in accordance with another embodiment of the present disclosure.
Figure 38D:
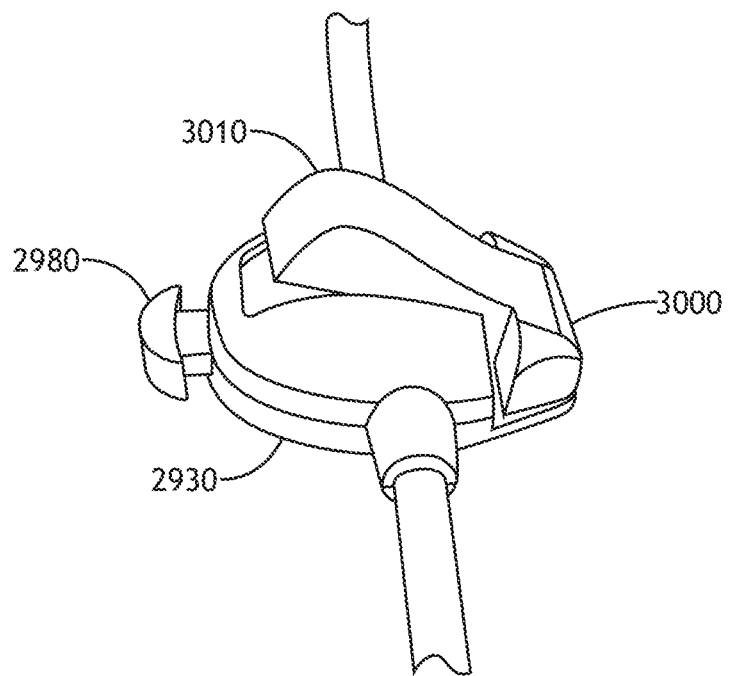
FIG. 38D depicts a side view of the mating device in accordance with another embodiment of the present disclosure.

Referring to FIG. 36A and FIG. 36B, a connector device 2920 is shown. The connector device 2920 may be employed with various types of monitors and EKG machines. The connector device includes at least three connectors 2940 configured to connect with 3 leads. However, the connector device 2920 may include more than three connectors 2940, and may include ten connectors 2940 to connect with 10 leads depending on the make and model of the single capturing device whether or not it is real time monitor, defibrillator monitor, or a 12 lead EKG machine. It should be understood that a 12 lead EKG is bit of a misnomer, rather a 12 lead EKG does not have 12 leads but has 10 leads, the EKG machine will monitor 12 parts of the heart capturing signals. A minimum of three leads may be employed to capture a single cycle of cardiac rhythm. In this situation, the three leads may be connected to a Right arm, a Left arm and a Left leg to be able to capture the cardiac cycle. For improved diagnostic purposes, 10 leads may be employed with 4 leads to the limbs and 6 leads to the chest.

The connector device 2920 may include a first port 2925, the first port 2925 configured to connect with a corresponding port 2915 that is connected to one end of the cable apparatus 2910. The connector device 2920 may include a second port 2928, the second port 2928 configured to connect with another corresponding port of an additional connector device. It is contemplated that the another corresponding port may be the first port 2925 of an additional connector device 2920 which allows the connector devices to be connected in series and allows multiple machines to operate simultaneously with the cable apparatus 2910. This is described further in FIG. 39 and FIG. 40.

Figure 31A:
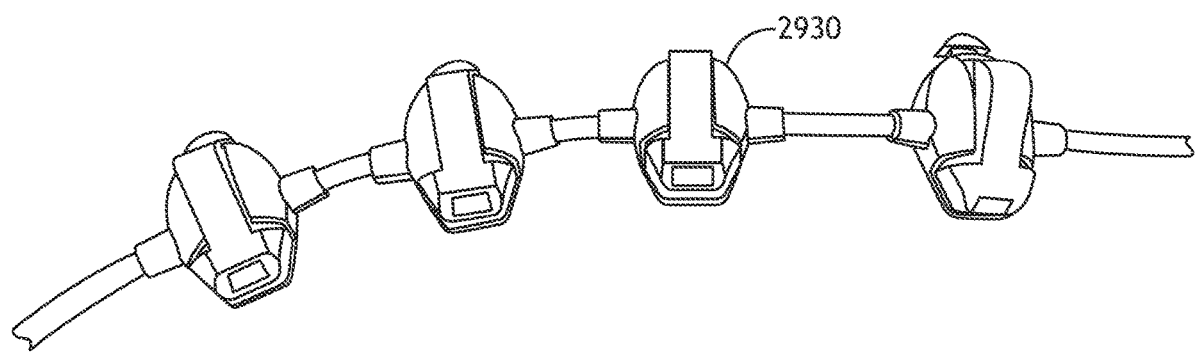
FIGS. 31A and 31B depict detailed views of one or more mating devices in accordance with another embodiment of the present disclosure.
Figure 31B:
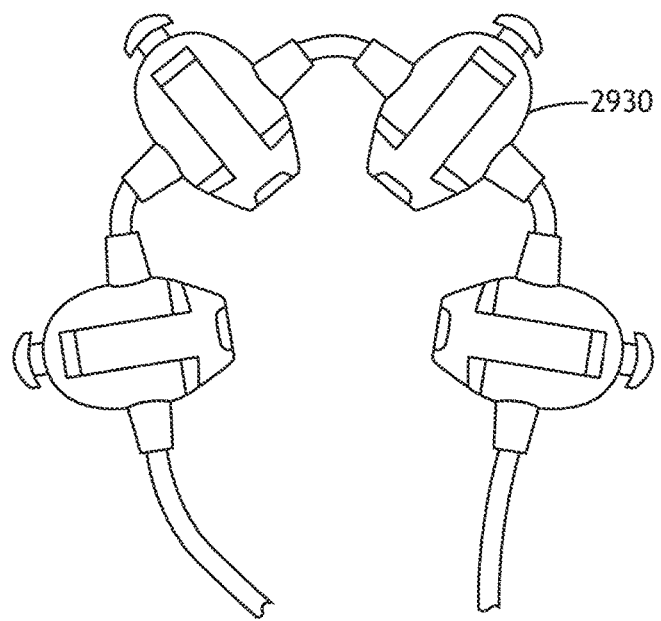
Figure 32:
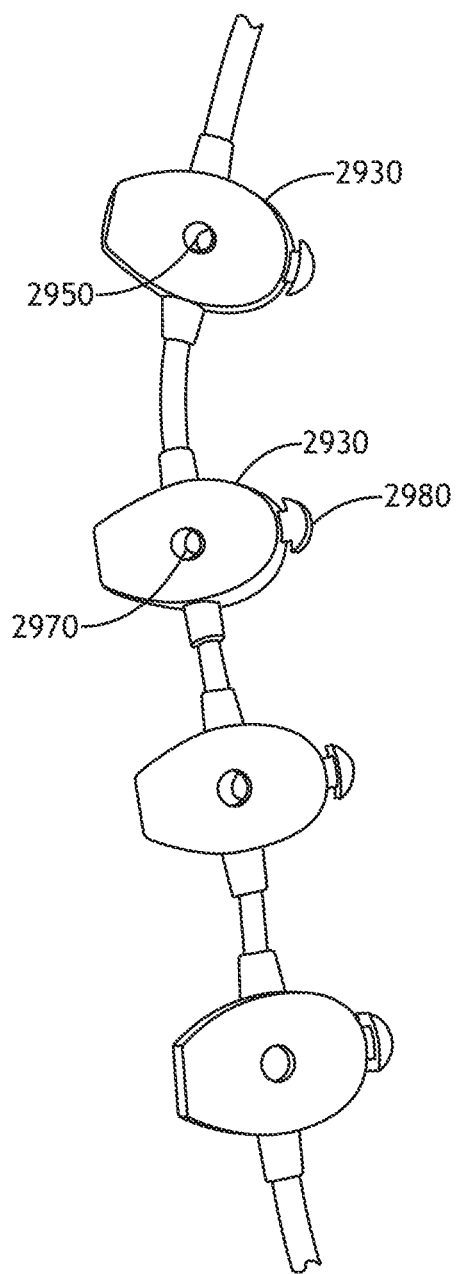
FIG. 32 depicts a bottom view of one or more mating devices in accordance with another embodiment of the present disclosure.
Figure 33A:
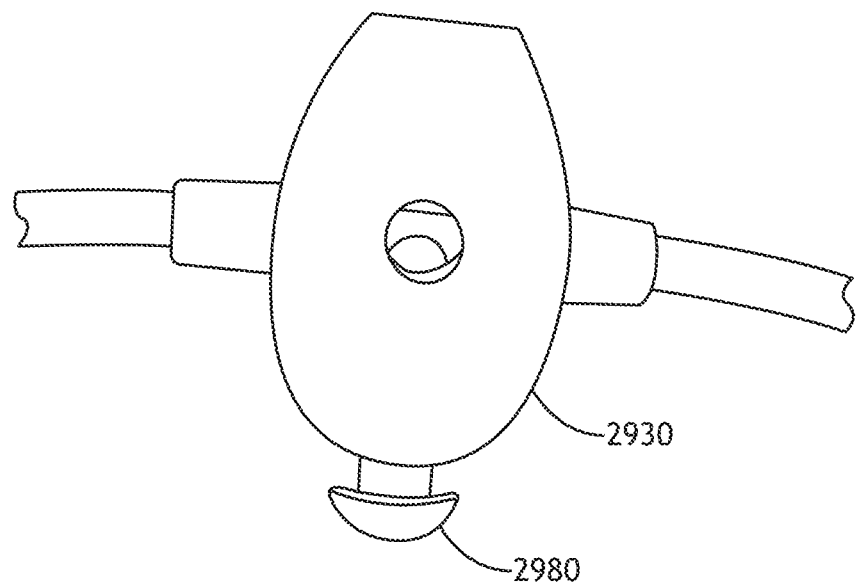
FIG. 33A depicts a detailed view of a mating device with a female receptacle in a closed position in accordance with another embodiment of the present disclosure.
Figure 33B:
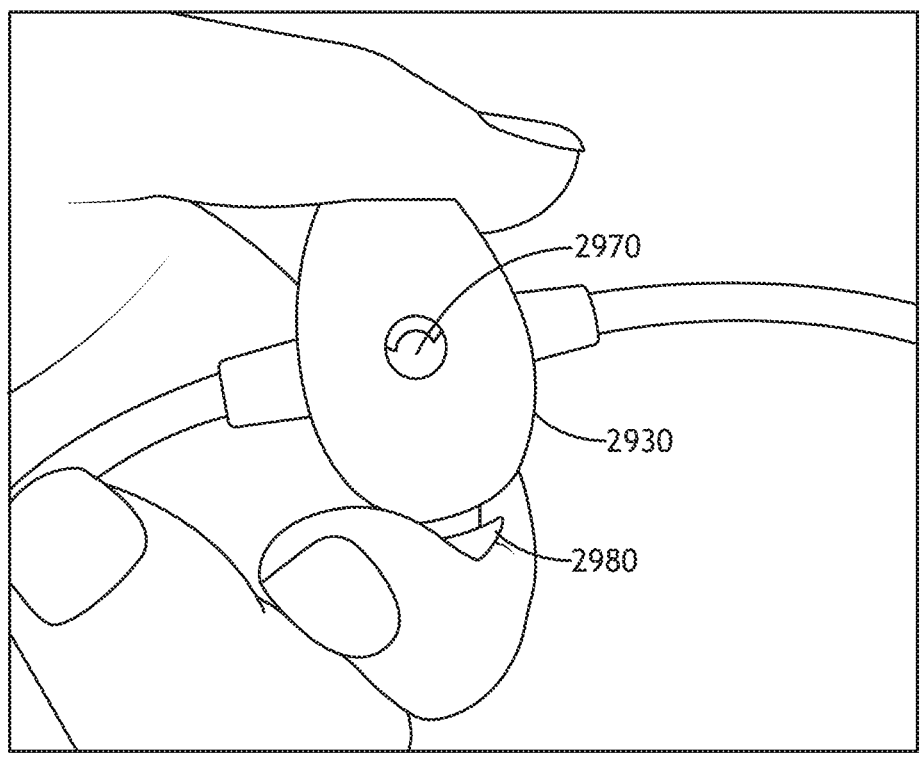
FIG. 33B depicts a detailed view of a mating device with a female receptacle in an open position in accordance with another embodiment of the present disclosure.
Figure 34A:
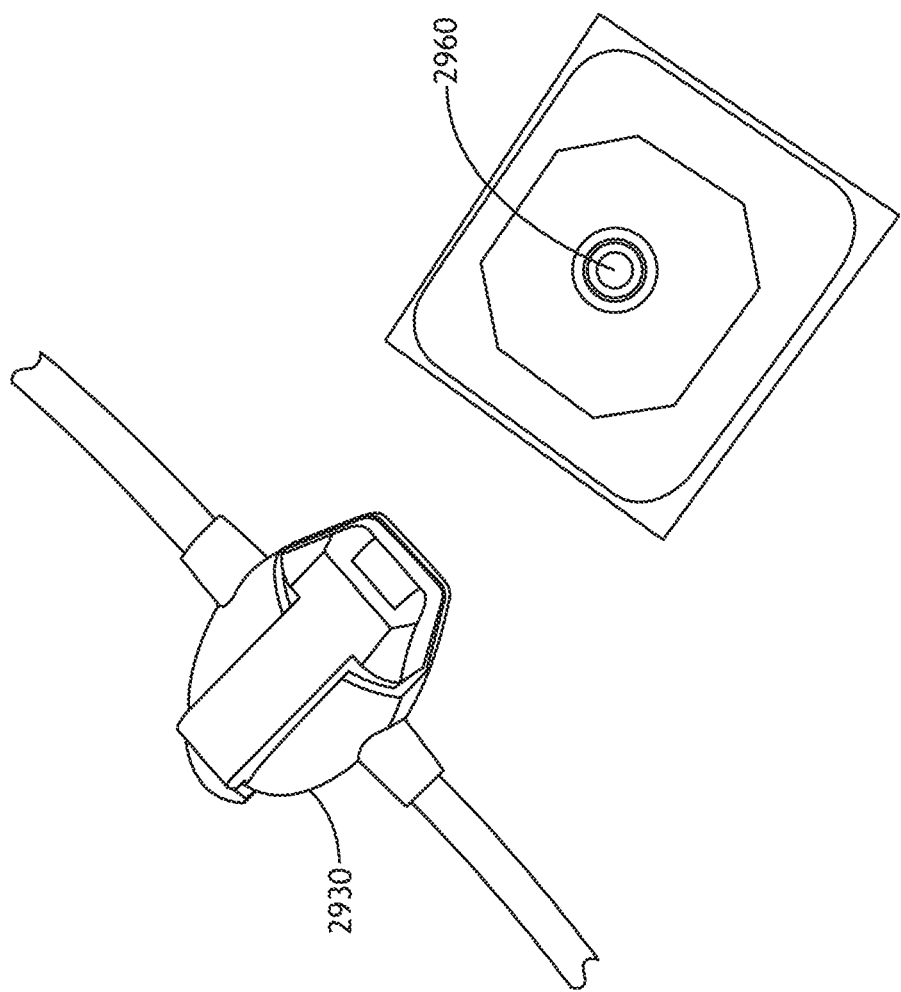
FIG. 34A through 34E depicts a mating device and an electrode in accordance with another embodiment of the present disclosure.
Figure 34B:
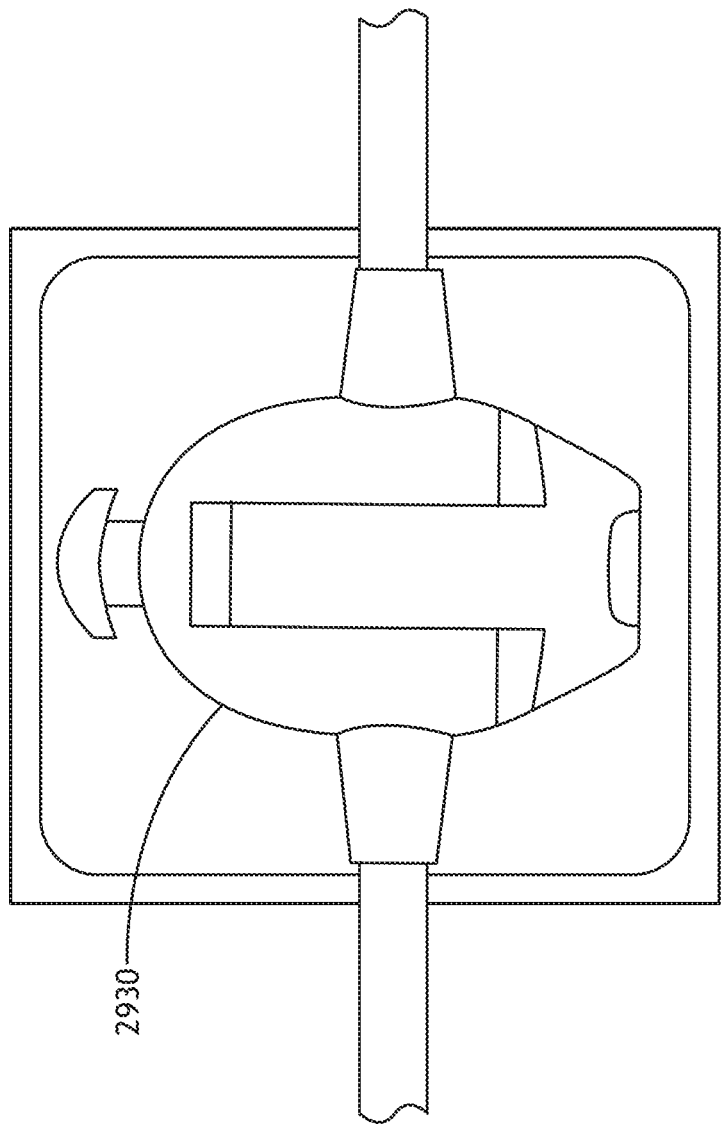
Figure 34C:
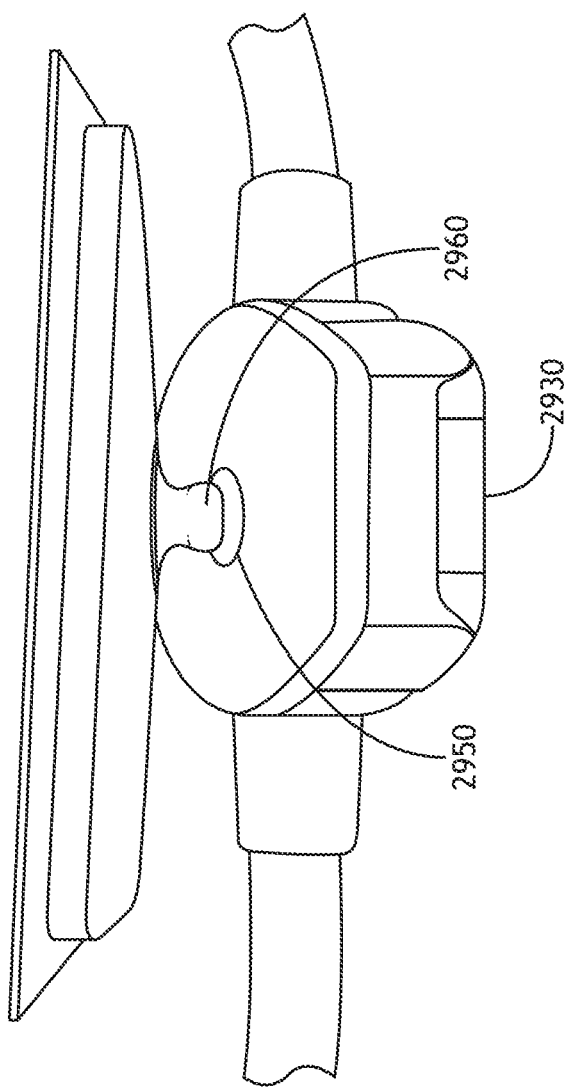
Figure 34D:
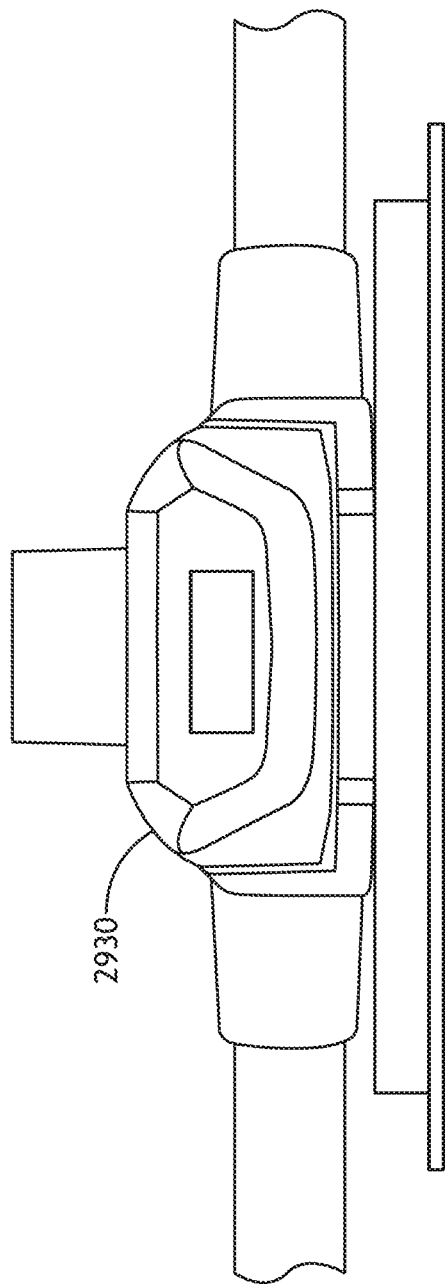
Figure 34E:
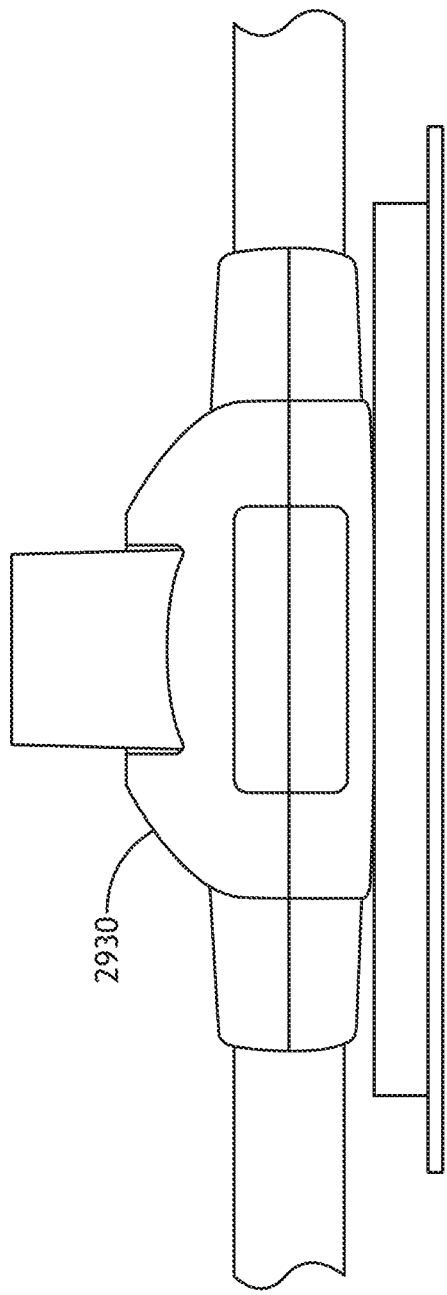

Referring to FIGS. 31A and 31B, the placement of the mating devices 2930 is selected in a manner that the mating devices 2930 may be used for a variety of people while allowing proper placement of the mating devices for each individual, e.g. individuals with varying heights and/or chest sizes. For example, the cable apparatus 2910 including the one or more mating devices may be adaptable for a chest size between 30 inches to 60 inches and a torso size between 15 inches to 30 inches. For instance, as shown in FIG. 31A, the cable apparatus 2910 may be adaptable for a user with a chest size of 60 inches and/or or a torso size of 30 inches such that the connecting cable between the one or more mating devices is not in a bent position. In another instance, as shown in FIG. 31B, the cable apparatus 2910 may be adaptable for a user with a chest size less than 60 inches and/or a torso size of less than 30 inches such that the connecting cable between the one or more mating devices is in at least a semi-bent position.

FIGS. 32 through 34E depict the one or more mating devices 2930 in accordance with one or more additional embodiments of the present disclosure. The cable apparatus 2910 may include a plurality of mating devices 2930. Each mating device 2930 may include a female receptacle 2950 of a snap connector with a zero insertion force mechanism to enhance patient comfort when applying the mating devices. The zero insertion force mechanism allows a user to easily secure the apparatus to the patient without causing unnecessary pain during application or removal, particularly during placement in a soft tissue area of the patient. Female receptacle 2950 may be configured to connect with a corresponding male groove 2960 coupled with an electrode pad. It is contemplated that a size of female receptacle 2950 may be similar as a size of female receptacles for an existing set of leads for an electrocardiograph whereby it will be operable with existing male groove portions of snap connector coupled to an electrode pad. The size of the aperture 2970 may be increased by depressing the tab 2980 on the mating device 2930 toward an interior of the mating device 2930 as shown in FIG. 33B. In such a fashion, there is not such a tension fit to connect the mating device 2930 to the corresponding male groove 2960 of the electrode pad.

Mating devices 2930 of the cable apparatus 2910 may further include an alligator dip 3000 which also has a zero insertion force mechanism, suitable for coupling with an electrode pad. An alligator clip 3000, also known as a spring clip or crocodile clip, may refer to an electrical connector. An alligator clip 3000 may include two jaws which may be mechanically forced together, when not separated by an opposing force, causing an electrical connection with an object coupled between the two jaws. Alligator clip 3000 may include binding clips, clamps and the like. This is shown in an exemplary fashion in FIG. 35B.

Figure 35A:
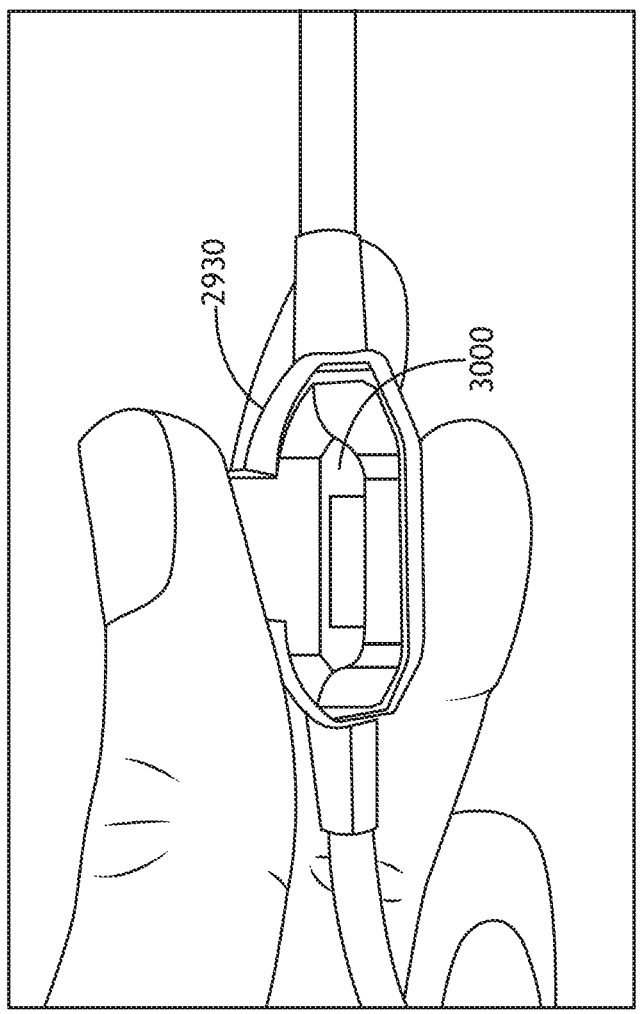
FIG. 35A through 35E depicts a mating device and an electrode in accordance with another embodiment of the present disclosure.
Figure 35B:
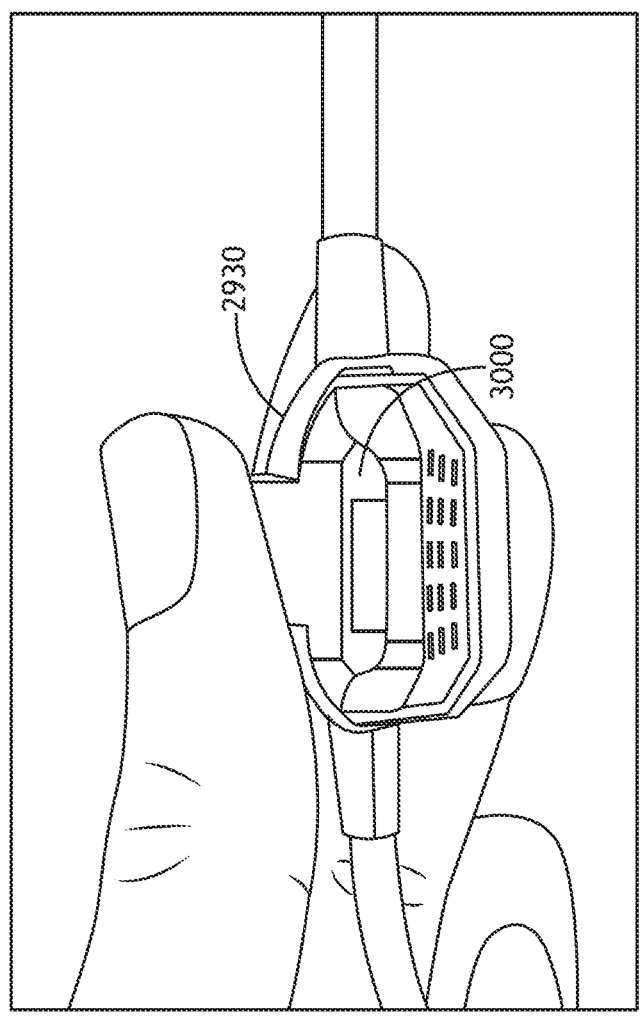
Figure 35C:
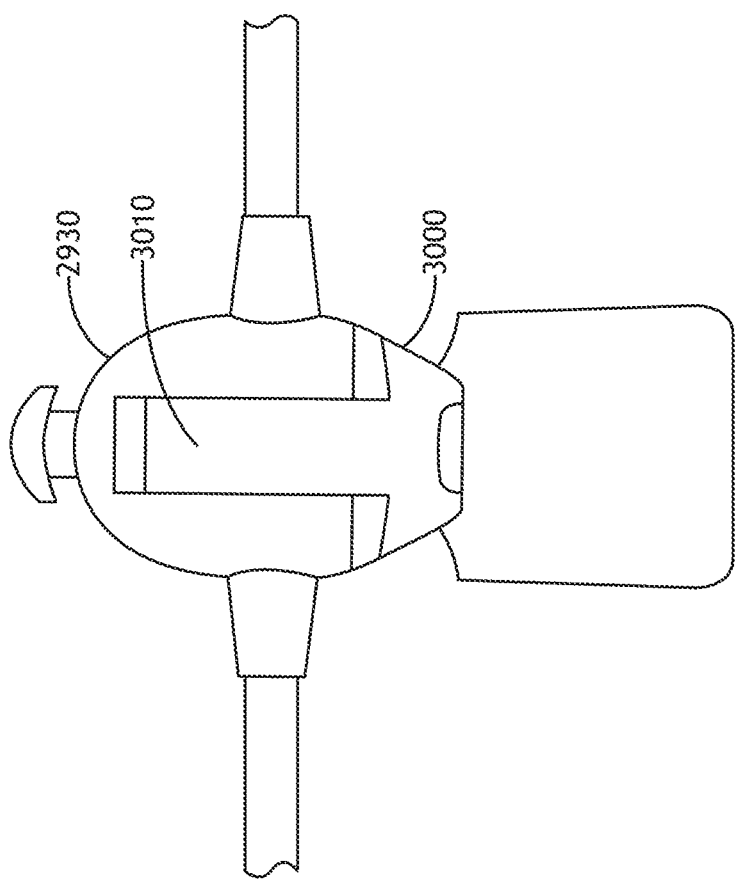
Figure 35D:
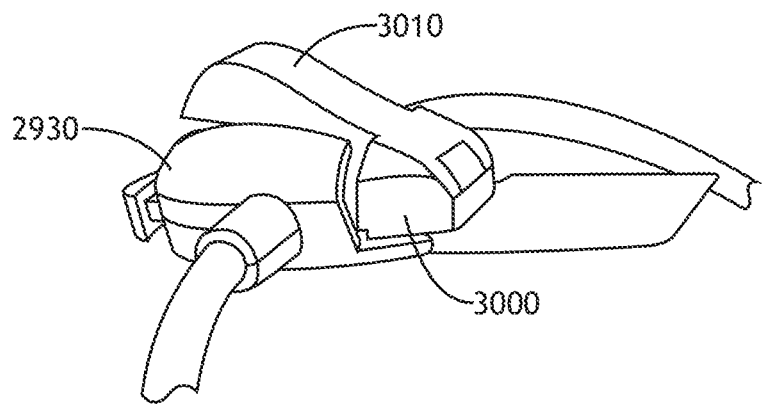
Figure 35E:
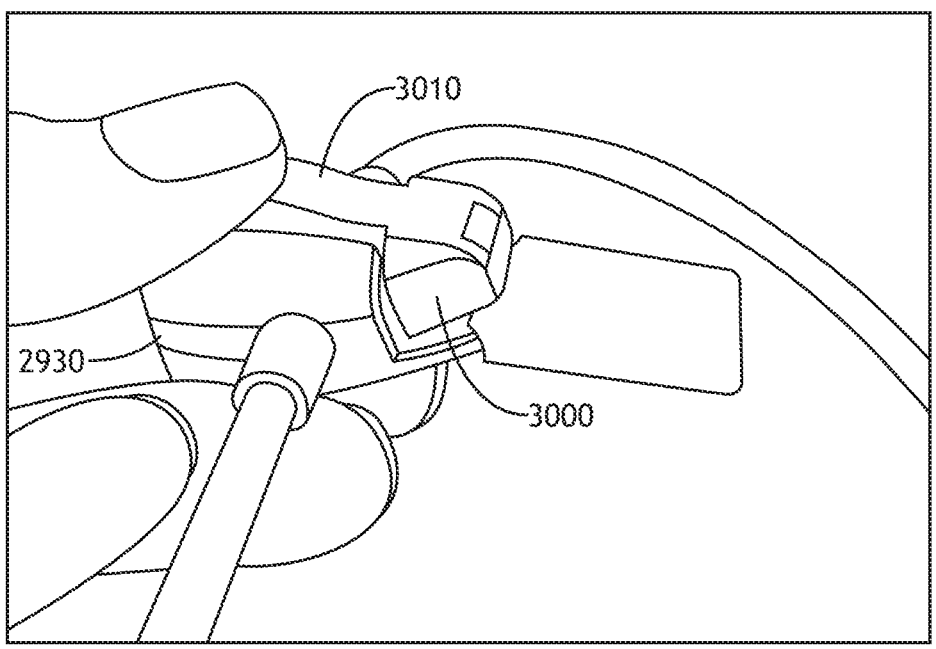

FIG. 35A through 35E depicts an exploded view of the alligator clip 3000. As shown in FIG. 35B, a user may press down on a lever 3010 of the alligator clip 3000 toward an interior of the mating device 2930 to open the jaws of the alligator clip 3000. When in an open position, the alligator clip 3000 is configured to receive a portion of an electrode pad. When in a closed position, as shown in FIGS. 35C and 35D, the alligator clip 3000 is configured to grasp a portion of the electrode pad. The interior of the alligator clip 3000 may include teeth to prevent the one or more leads from slipping out of the alligator clip 3000

The mating device 2930 including a snap and clip in the same mating device is unique and allows universal connection to various types of electrode pads. The combination of snap and clip combo mounted on single line and of course the ability of this system (the cable apparatus 2910 and the connector device 2920) to be able to connect in series connecting all signal capture devices is highly advantageous, regardless of the make or model of the EKG machine or monitoring machine. The lever 3010 of the alligator clip 3000 is located in the same area as the tab 2980 for the snap connector in order to allow medical personnel to quickly connect the mating device to any kind of electrode. The alligator clip 3000 may be engaged by a lever 3010 at the top, rear portion of the mating device 2930 while the tab 2980 for the snap connector is at the rear portion of the mating device 2930. As can be seen, the mating device 2980, whether connected via the snap or alligator clip, is allowed to lay flat on the patient. This is advantageous as it may improve patient comfort while retaining a solid connection to the corresponding electrode pad.

Referring once again to FIGS. 29 through 38D, the cable apparatus 2910 and a connector device 2920 including one or more mating devices as shown provides a number of advantages that are not available in conventional sets of leads and other products. The cable apparatus 2910 and connector device 2920 may stay on the patient throughout the hospitalization eliminating cross contamination and thus reducing spread of infection, and yet may connect to a variety of machines, regardless of the model or type of the machine.

The cable apparatus 2910 may be formed as a single cable; encasing multi-channel conductors and capable of performing 3-5-10 leads cardiac tracing, without unplugging from the patient. The cable apparatus 2910 may be applied directly to patients, and then multiple devices may quickly connect to the cable apparatus 2910 through the connector device 2920. The cable apparatus 2910 and connector device 2920 may eliminate expensive EKG machines and monitors and their bulky leadwires to come in contact with patients directly, as otherwise making them difficult to be adequately disinfected. The mating device 2930 includes a unique clip and snap combo design along a single multi-conductor cable will connect to both tab and pad electrodes. The zero insertion force design of the snap section of the clip and snap combo design prevents unnecessary pain to a patient during application.

The connector device 2920 includes connectors 2940 which are configured to connect with all cardiac signal capturing devices/machines. The connector device 2920 may include a variety of connectors and may be configured to connect with the set of leads from any type of device, regardless of their make or model. The set of leads may include connectors such as snap, pinch clip, banana, plug 1 mm-4 mm, and alligator clips which can connect to connectors 2940 of the connector device 2920. The cable apparatus 2910 may be applicable to chest sizes from 30"-60" and torso 15"-30" considering human factors. The cable apparatus 2910 may include Bluetooth connecting capabilities between the patient cable and the connector device 2920, Bluetooth connecting capabilities to smart phones, pads, or tablets. Additionally, cable apparatus 2910 may include hardwire connecting capabilities to smart phones, pads, or tablets. The cable apparatus 2910 may be manufactured in single-use materials or recyclable materials.

Figure 39:
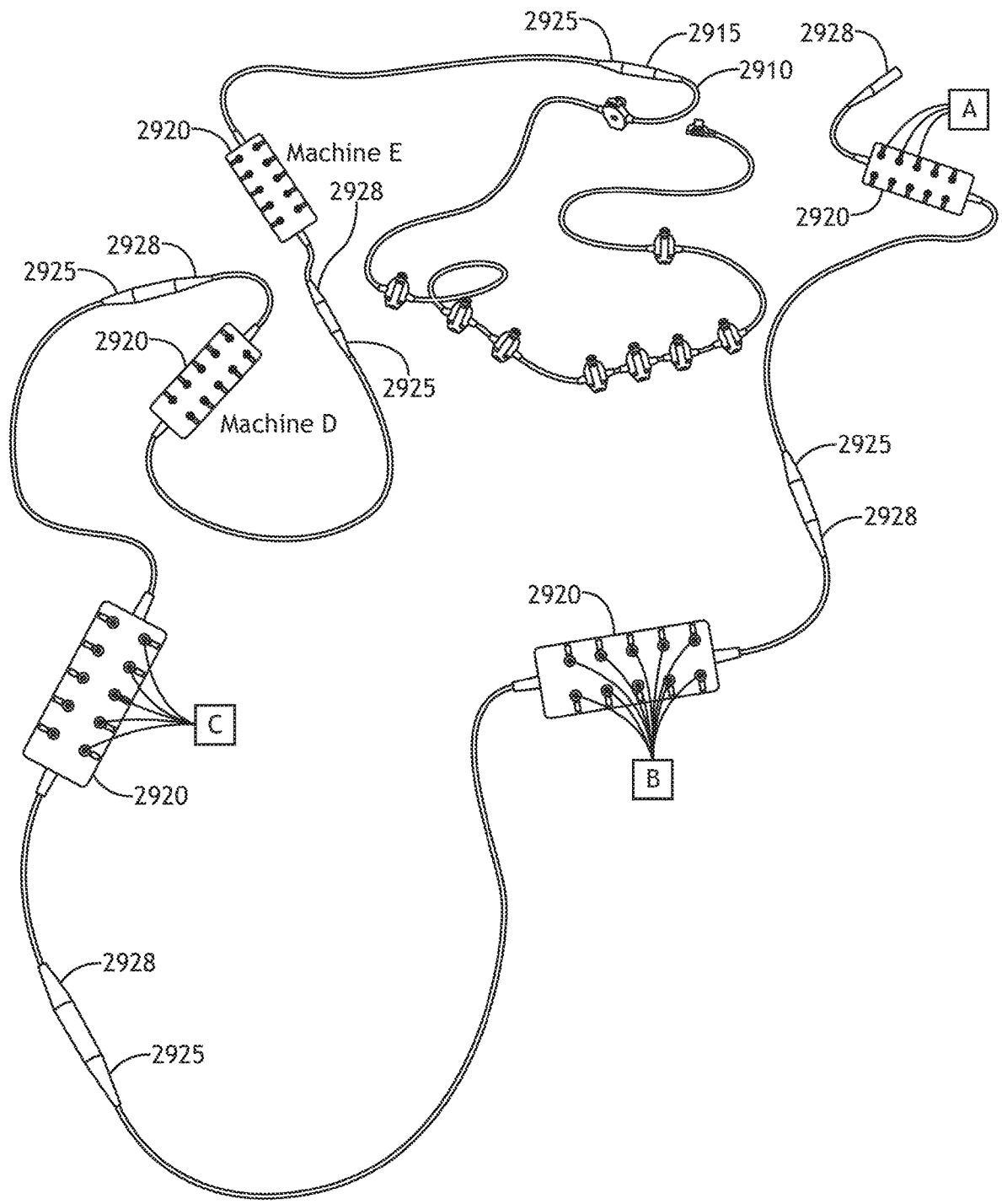
FIG. 39 depicts a plurality of connector devices which are connected in series where one of the connector devices is connected to a cable in accordance with another embodiment of the present disclosure.

Referring to FIG. 39, it is contemplated that a plurality of connector devices 2920 may be connected in series, where one of the connector devices 2920 is connected to a cable apparatus 2910 of the present disclosure. This may allow multiple types and varieties of machines to be connected to the cable apparatus 2910 easily and quickly, in order for all of them to conduct tests or monitor a patient's condition, separately or simultaneously at the same time. The connector devices 2920 and cable apparatus 2910 have been tested and researched such that multiple connector devices 2920 may be connected in series receiving a cardiac signal from the cable will not cause any change, introduce error, or create interference. Also, testing has shown that a 12 lead EKG with diagnostic interpretation capabilities has exact interpretation even when multiple connector devices 2920 are connected in series with other connector devices. For example, testing showed that any rhythm that is appearing on the real time monitor will show the exact rhythm, and a defibrillator monitor as well as the 12 lead EKG that has diagnostic interpretation capabilities.

Figure 40:
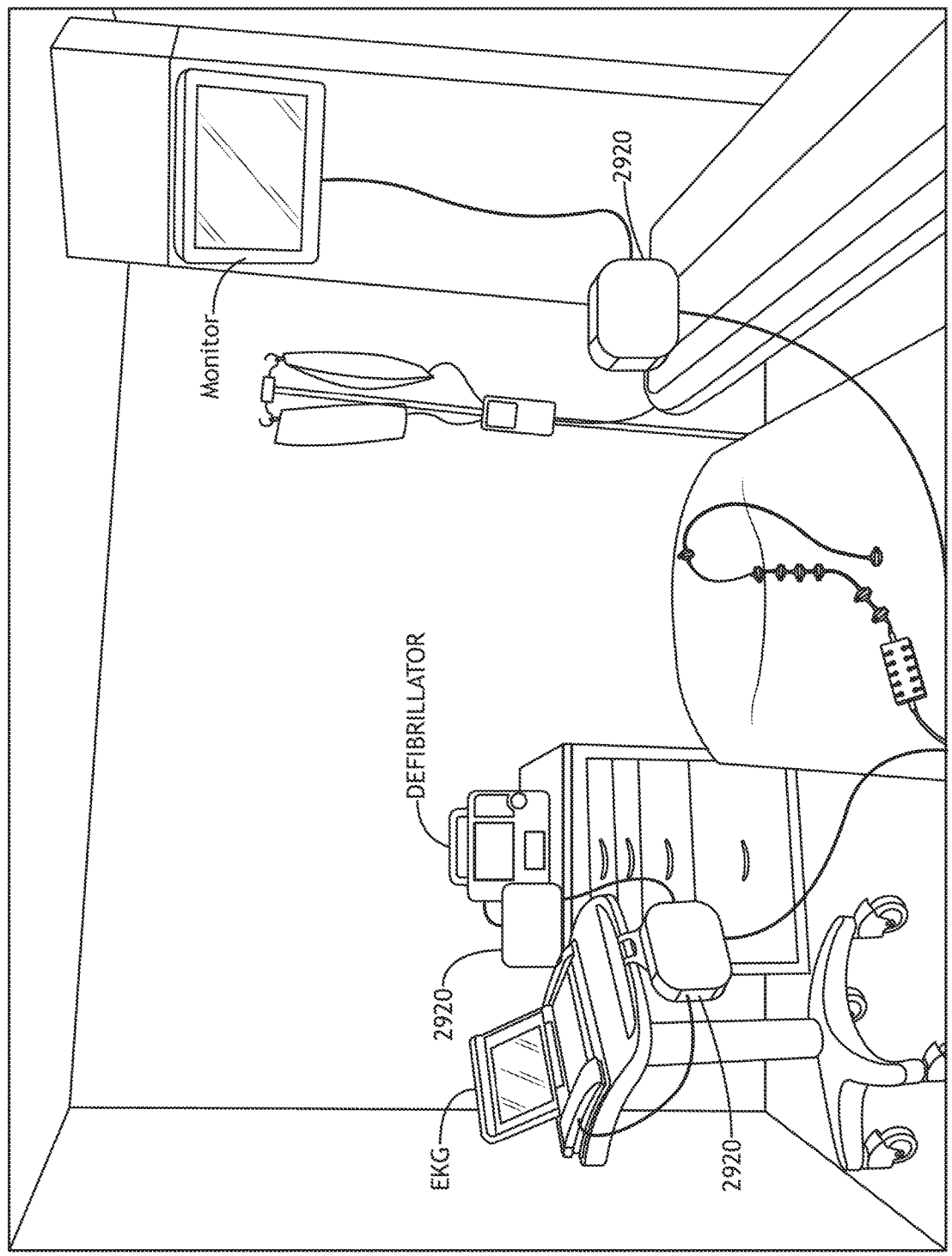
FIG. 40 depicts an exemplary usage of connector devices connected in series whereby one connector device is connected to a cable while allowing a simultaneous connection to four machines, including an EKG machine in accordance with another embodiment of the present disclosure.

Referring to FIG. 40, an exemplary usage of connector devices 2920 connected in series whereby one connector device 2920 is connected to a cable apparatus 2910 while allowing a connection to multiple machines, including an EKG machine, defibrillator, or monitor is shown. Additionally, as shown in FIG. 40, a wireless connection device, such as a Bluetooth connection device, may be coupled to the cable and the connector devices. This may provide for wireless monitoring and wireless data transmission which may be sent to a mobile device of a health provider.

In operation, a patient who has an emergency condition may be connected with a cable apparatus 2910 and a connector device 2920. When the patient is transferred to an emergency room by the ambulance, the cable apparatus 2910 and connector device 2920 may remain on or with the patient. As shown in FIG. 40, an EKG machine or defibrillator may be quickly and easily connected to the cable apparatus 2910, regardless of model or type of the machine, by connecting through connector device 2920. As shown in FIG. 40, organization may be improved through a carrying bag that stores the connector device 2920 and the existing set of leads from the associated device, such as the EKG machine, defibrillator, or monitor. Additionally, the EKG machine, defibrillator, and the monitor may be simultaneously connected to the cable apparatus 2910 through the series connection of the connector devices 2920.

The cable apparatus 2910 and connector device 2920 may provide a number of advantages to improve patient care, improve operating conditions for staff, and reduce medical costs. These are listed below.

Improving Patient Quality of Care
- Lead reversal is eliminated, thus eliminating misinterpretation that may lead to misdiagnosis.
- Consistency in lead placements by all staff.
- Easily and quickly obtain serial 12 EKGs which are needed during Acute MI's as well as during Code or even chest pain rule outs.
- Lowering the risk of cross-contamination of equipment that are difficult to clean thus reducing risk of spread of infection, one cable per patient.
- Zero insertion force, (ZIF) connectors, prevents damage to the fragile skin and or pain upon application of the cable to the patient.
- Seldom you need to awaken, uncover, or expose the patient during repeated acquisition of 12 lead EKG.

Staff Friendly
- Simply Plug and Play
- A simple device that does so much
- Universal adapter design of the connector device interfaces with all EKG signal capturing devices including all telemetries and multi-channel Holter monitors regardless of their make or model
- It is used by paramedics, hospital staff, and outpatient clinic staff alike.
- Converts all scattered 3 to 15 conventional EKG wires to one single cable
- Mistake proof one-line cable design
- It is easily and quickly applied.
- Lead reversal is eliminated.
- Flexible and light weight yet tough design.
- One-line cable design remains on the patient much more securely than conventional cables where they continue to torque and fall off the patient due to their inherent heavy and bulky nature.
- Unique combination Snap and Clip design allows the staff to utilize Tab and or Pad electrodes
- Easier to clean and disinfect one cable rather than 35 cables or even more depending on what other signal capturing devices we are connecting together. For example: paramedic defibrillator monitor, hospital real time monitor, hospital defibrillator monitor, 12 lead EKG monitor.
- No need to search and identify each lead before applying of up to 15 heavy, bulky, and scattered leads of conventional lead wires.
- Repeated applications of bulky EKG wires by conventional lead wires and methods are quite cumbersome and frustrating for the staff.

Saving Money
- Costly wound infections by spread through conventional leads.
- Costly misinterpretation and misdiagnosis from lead reversal
- Costly repeating EKGs due to lead reversal, calling patients to come back in for repeat EKG
- Costly wasting of tabs and add electrodes for serial EKG.
- Costly wasting of tabs when they are pulled off the patient by heavy and bulky wires thus will not stick again so staff will use new tabs that may also follow the same fate.

It is believed that the apparatus of the present disclosure and many of its attendant advantages will be understood by the forgoing description. It is also believed that it will be apparent that various changes may be made in form, construction, and arrangement of the components thereof without departing from the scope and spirit of the invention or without sacrificing all of its material advantages. The form herein before described being merely an explanatory embodiment thereof.

The invention claimed is:

1. An apparatus, comprising:
a cable, said cable including a plurality of conductors enclosed within an exterior covering that covers a length of the cable;
a plurality of mating devices, said plurality of mating devices located along various positions along the length of said cable from a first end of said cable to a second end of said cable, each mating device coupled to one corresponding conductor of said plurality of conductors of said cable, each mating device including a top side, a bottom side, a front side, and a rear side, each mating device of said plurality of mating devices includes a female receptacle of a snap connector located on the bottom side of each mating device configured to connect with a corresponding male groove portion of the snap connector connected with a first type of an electrode pad and an alligator clip configured for coupling with a second type of electrode pad; and
a connector device, said connector device coupled to one end of said cable, said connector device configured to couple with a set of leads from a device;
wherein said snap connector includes a tab on the rear side of the mating device, said tab is configured to be depressed toward an interior of the mating device in order to increase a size of an aperture of the female receptacle of the snap connector located on the bottom side of the mating device, wherein said alligator clip includes the alligator clip includes two jaws located on the front side of the mating device and a lever located on the top side of the mating device, said lever configured to be depressed toward an interior of the mating device in order to open the two jaws of the alligator clip, wherein the tab of the snap connector and the lever of the alligator clip are separate, distinct structures.

2. The apparatus as claimed in claim 1, wherein said exterior covering covers said plurality of conductors from said first end of said cable to said second end of said cable.

3. The apparatus as claimed in claim 1, wherein said connector device includes a first port, the first port configured to connect with a corresponding port that is connected to one end of the cable.

4. The apparatus as claimed in claim 3, wherein said connector device includes a second port, the second port configured to connect with another corresponding port of an additional connector device.

5. The apparatus as claimed in claim 1, wherein each mating device further includes a first side and a second side.

6. The apparatus as claimed in claim 5, wherein the mating device is coupled to one corresponding conductor of said plurality of conductors of said cable, the cable connects to the first side of the mating device and the second side of the mating device.

7. An apparatus, comprising:
a cable, said cable including a plurality of conductors enclosed within an exterior covering that covers a length of the cable;

a plurality of mating devices, said plurality of mating devices located along various positions of the length of said cable beginning in proximity with a first end of said cable throughout the length of the cable and to a second end of said cable, each mating device coupled to one corresponding conductor of said plurality of conductors of said cable, each mating device including a top side, a bottom side, a front side, and a rear side, each mating device of said plurality of mating devices includes a female receptacle of a snap connector located on the bottom side of the mating device configured to connect with a corresponding male groove portion of the snap connector connected with a first type of an electrode pad and an alligator clip configured for coupling with a second type of electrode pad, the alligator clip includes two jaws located on the front side of the mating device which are mechanically forced together when not separated by an opposing force to allow placement of the second type of electrode pad between the two jaws and cause an electrical connection without the opposing force; and a connector device, said connector device coupled to one end of said cable, said connector device configured to couple with a set of leads from a device;

wherein said snap connector includes a tab on the rear side of the mating device, said tab is configured to be depressed toward an interior of the mating device in order to increase a size of an aperture of the female receptacle of the snap connector located on the bottom side of the mating device, wherein said alligator clip includes a lever located on the top side of the mating device, said lever configured to be depressed toward an interior of the mating device in order to open the two jaws of the alligator clip, wherein the tab of the snap connector and the lever of the alligator clip are separate, distinct structures.

8. The apparatus as claimed in claim 7, wherein said exterior covering covers said plurality of conductors from said first end of said cable to said second end of said cable.

9. The apparatus as claimed in claim 7, wherein said connector device includes a first port, the first port configured to connect with a corresponding port that is connected to one end of the cable.

10. The apparatus as claimed in claim 9, wherein said connector device includes a second port, the second port configured to connect with another corresponding port of an additional connector device.

11. The apparatus as claimed in claim 9, wherein the connector device includes at least ten connectors configured to couple with the set of leads from the device.

12. The apparatus as claimed in claim 11, wherein the at least ten connectors are male plugs configured to be coupled with a set of female snap receptacles associated with the set of leads from the device.

13. The apparatus as claimed in claim 7, wherein each mating device further includes a first side and a second side.

14. The apparatus as claimed in claim 13, wherein each mating device is coupled to one corresponding conductor of said plurality of conductors of said cable, the cable connects to the first side of the mating device and the second side of the mating device.

* * * * *

UNITED STATES PATENT AND TRADEMARK OFFICE
CERTIFICATE OF CORRECTION

PATENT NO. : 11,817,660 B1
APPLICATION NO. : 17/013197
DATED : November 14, 2023
INVENTOR(S) : Dariush Ghaffari et al.

Page 1 of 1

It is certified that error appears in the above-identified patent and that said Letters Patent is hereby corrected as shown below:

On the Title Page

Item (12) delete "Ghaffari" and insert --Ghaffari et al.--.

Item (72) Inventor insert: --Joshua A. Ghaffari, Omaha, NE (US)--.

Signed and Sealed this
Third Day of December, 2024

Katherine Kelly Vidal
*Director of the United States Patent and Trademark Office*